(12) United States Patent
Mazin

(10) Patent No.: US 10,442,817 B2
(45) Date of Patent: Oct. 15, 2019

(54) INHIBITORS OF RAD52 RECOMBINATION PROTEIN AND METHODS USING SAME

(71) Applicant: Alexander V. Mazin, Philadelphia, PA (US)

(72) Inventor: Alexander V. Mazin, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/578,558

(22) PCT Filed: Jun. 3, 2016

(86) PCT No.: PCT/US2016/035750
§ 371 (c)(1),
(2) Date: Nov. 30, 2017

(87) PCT Pub. No.: WO2016/196955
PCT Pub. Date: Dec. 8, 2016

(65) Prior Publication Data
US 2018/0134727 A1    May 17, 2018

Related U.S. Application Data

(60) Provisional application No. 62/170,985, filed on Jun. 4, 2015.

(51) Int. Cl.
| | |
|---|---|
| *C07D 215/38* | (2006.01) |
| *C07D 405/12* | (2006.01) |
| *C07D 239/95* | (2006.01) |
| *C07D 471/04* | (2006.01) |
| *C07D 495/04* | (2006.01) |
| *A61K 31/517* | (2006.01) |
| *A61K 31/496* | (2006.01) |
| *A61K 31/55* | (2006.01) |
| *A61K 31/47* | (2006.01) |
| *A61K 45/06* | (2006.01) |
| *A61P 35/00* | (2006.01) |
| *C07D 491/048* | (2006.01) |
| *A61K 31/4525* | (2006.01) |
| *A61K 31/4741* | (2006.01) |
| *A61K 31/5377* | (2006.01) |

(Continued)

(52) U.S. Cl.
CPC ........ *C07D 495/04* (2013.01); *A61K 31/4188* (2013.01); *A61K 31/4525* (2013.01); *A61K 31/47* (2013.01); *A61K 31/4741* (2013.01); *A61K 31/496* (2013.01); *A61K 31/517* (2013.01); *A61K 31/5377* (2013.01); *A61K 31/55* (2013.01); *A61K 45/06* (2013.01); *A61P 35/00* (2018.01); *C07D 215/38* (2013.01); *C07D 239/95* (2013.01); *C07D 307/82* (2013.01); *C07D 405/12* (2013.01); *C07D 471/04* (2013.01); *C07D 491/048* (2013.01); *C07D 491/056* (2013.01)

(58) Field of Classification Search
CPC .. C07D 215/38; C07D 405/12; C07D 239/95; C07D 471/04; C07D 495/04; C07D 307/82; A61K 31/517; A61K 31/496; A61K 31/55; A61K 31/47; A61K 45/06; A61P 35/00
See application file for complete search history.

(56) References Cited

U.S. PATENT DOCUMENTS

| | | | |
|---|---|---|---|
| 6,737,547 B1 | 5/2004 | Nachman et al. | |
| 7,084,156 B2 * | 8/2006 | DeVita | C07D 215/227 514/312 |

(Continued)

OTHER PUBLICATIONS

Cancer-prevention, 2018, https://www.mayoclinic.org/healthy-lifestyle/adult-health/in-depth/cancer-prevention/art-20044816.*

(Continued)

*Primary Examiner* — Sun Jae Yoo
(74) *Attorney, Agent, or Firm* — Saul Ewing Arnstein & Lehr LLP; Kathryn Doyle; Domingos J. Silva

(57) ABSTRACT

The present invention includes novel RAD52 inhibitors for preventing or treating cancers in a subject in need thereof. The present invention further includes a method of preventing or treating cancers in a subject in need thereof, the method comprising administering to the subject an effective amount of a compound of the invention. In certain embodiments, the subject is further administered at least one additional therapeutic agent.

10 Claims, 24 Drawing Sheets
Specification includes a Sequence Listing.

(I)

(IX)

(51) Int. Cl.
    *C07D 307/82*     (2006.01)
    *C07D 491/056*     (2006.01)
    *A61K 31/4188*     (2006.01)

(56) References Cited

U.S. PATENT DOCUMENTS

| | | | |
|---|---|---|---|
| 7,666,873 B2 * | 2/2010 | Taniguchi | C07D 213/75 |
| | | | 514/253.06 |
| 2005/0026984 A1 | 2/2005 | Bigot et al. | |
| 2014/0235634 A1 | 8/2014 | Ong et al. | |
| 2016/0160205 A1 * | 6/2016 | Johnston | A61K 31/4196 |
| | | | 514/259.3 |

OTHER PUBLICATIONS

Huang et al., Nucleic Acids Research, 2016, 44(9), 4189-4199.*
Sullivan-Reed-et-al., Cell Rep., 2018, 23(11), 3127-3136.*
Sullivan et al., 2019, http://www.bloodjournal.org/content/126/23/4434?sso-checked=true.*
Mazin et al., 2019, https://drexel.edu/coulter/projects/overview/inhibitors-of-RAD52-as-a-therapy-against-BRCA-deficient-breast-cancer-and-ovarian-cancer/.*
International Search Report and Written Opinion for PCT International Application No. PCT/US2016/035750 dated Oct. 14, 2016.

* cited by examiner

INHIBITORS OF RAD52 RECOMBINATION PROTEIN AND METHODS USING SAME

CROSS-REFERENCE TO RELATED APPLICATIONS

The present application is a 35 U.S.C. § 371 national phase application from, and claims priority to, International Application No. PCT/US2016/035750, filed Jun. 3, 2016, and published under PCT Article 21(2) in English, which claims priority under 35 U.S.C. § 119(e) to U.S. Provisional Application No. 62/170,985, filed Jun. 4, 2015, all of which applications are incorporated herein by reference in their entireties.

STATEMENT REGARDING FEDERALLY SPONSORED RESEARCH OR DEVELOPMENT

This invention was made with government support under grant numbers MH097512-01, CA100839 and CA188347 awarded by National Institutes of Health. The government has certain rights in the invention.

BACKGROUND OF THE INVENTION

DNA repair is essential for maintenance of genome integrity in all organisms. Numerous DNA repair systems evolved to eliminate a broad variety of DNA lesions caused by exogenous agents or genotoxic products of metabolism. In normal cells, the specificities of different DNA repair mechanisms overlap to assure efficient genome protection. However, cancer cells often lose some DNA repair pathways due to intrinsic genome instability. In this case, cancer cell viability depends on the remaining alternative DNA repair mechanisms. Poly (ADP-ribose) polymerase 1 (PARP1), a protein involved in DNA damage signaling and repair of DNA single-stranded breaks (SSB), is essential for viability of cancer cells that are deficient in the homologous recombination (HR) pathway. Furthermore, hereditary breast cancer and ovarian cancer cells, which often carry mutations in HR proteins BRCA1 or BRCA2, can be eliminated using PARP1 inhibitors with a minimal harm to normal cells with at least one copy of functional BRCA1/2 genes.

BRCA1/2-deficient cancer cells are not viable when RAD52 protein is inactivated. In addition, RAD52 knockdown also causes lethality to human cells deficient in PALB2 (partner and localizer of BRCA2) and five RAD51 paralogs, including RAD51C. Mutations in PALB2 and RAD51C also contribute to hereditary breast and ovarian cancer. Previously, inviability of double mutations in RAD52 and RAD51C genes was reported in chicken DT-40 cells. Inactivation of PARP1 and RAD52 causes lethality of BRCA1/2-deficient and PALB2-deficient cells through different mechanisms. Inactivation of PARP1 causes disruption of repair of DNA SSBs. During DNA replication, unrepaired SSBs may cause formation of DNA double-stranded breaks (DSBs) or stalled replication forks, which are repaired by the HR pathway. BRCA1/2/PALB2 constitute the major sub-pathway of HR; mutations in these proteins incapacitates HR making hereditary breast and ovarian cancer cells vulnerable to PARP1 inhibitors. However, recent data have demonstrated that, in addition to the BRCA1/2/PALB2 sub-pathway, the secondary HR sub-pathway operates in mammalian cell that depends on RAD52 protein. In normal mammalian cells, this pathway plays a minor role, as RAD52−/− mice are viable and fertile and do not display DNA damage sensitivity, abnormalities, or significant cancer predisposition. However, this sub-pathway becomes essential for viability in cells that lack the BRCA1/2/PALB2 sub-pathway.

There is a need in the art for novel compositions and methods that are useful for the treatment of cancers through inhibition of RAD52 in a mammal. The present invention addresses this unmet need.

BRIEF SUMMARY OF THE INVENTION

The invention provides certain compounds that are RAD52 inhibitors. The invention further provides a pharmaceutical composition comprising at least one compound of the invention and at least one pharmaceutically acceptable carrier. The invention further provides a method of preventing or treating a RAD52 related disease or disorder in a subject in need thereof. The invention further provides a method of preventing or treating a cancer in a subject in need thereof.

In certain embodiments, the compound is a compound of formula (I):

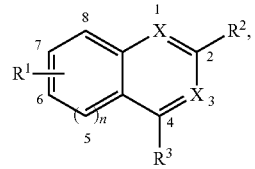

wherein in (I): $R^1$ is selected from the group consisting of:

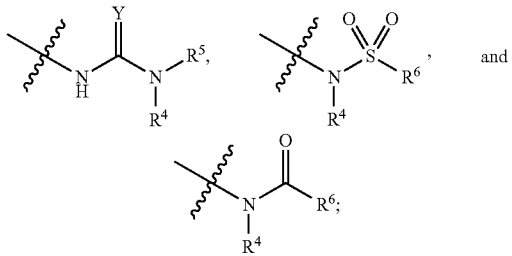

$R^2$ is $-NR^4R^5$; $R^3$ is selected from the group consisting of hydrogen, $-(C_1-C_6)$alkyl, $-(C_1-C_6)$haloalkyl, $-(C_1-C_6)$heteroalkyl, $-F$, $-Cl$, $-Br$, $-I$, $-CN$, $-NO_2$, $-OR^7$, $-SR^7$, $-S(=O)R^7$, $-S(=O)_2R^7$, $-C(=O)R^7$, $-OC(=O)R^7$, and $-CO_2R^7$; each occurrence of $R^4$ and $R^5$ is independently selected from the group consisting of hydrogen, $-(C_1-C_6)$alkyl, $-(C_1-C_6)$haloalkyl, $-(C_1-C_6)$heteroalkyl, aryl, and heteroaryl, wherein the aryl or heteroaryl group is optionally substituted; or $R^4$ and $R^5$; together with the nitrogen to which $R^4$ and $R^5$ are connected, form a $-(C_3-C_{10})$heterocyclyl; each occurrence of $R^6$ is independently selected from the group consisting of $-(C_1-C_6)$alkyl, $-(C_1-C_6)$heteroalkyl, $-OR^7$, $-(C_3-C_{10})$heterocyclyl, aryl, and heteroaryl, wherein the $-(C_3-C_{10})$heterocyclyl, aryl or heteroaryl group is optionally substituted; each occurrence of $R^7$ is independently selected from the group consisting of H, $-(C_1-C_6)$heteroalkyl, $-(C_3-C_6)$cycloalkyl, $-(C_4-C_{10})$heterocyclyl, aryl, and $-(C_5-C_{10})$heteroaryl, wherein the alkyl, heteroalkyl, cycloalkyl, heterocyclyl, aryl, or heteroaryl group is optionally substituted; each occurrence of X is independently CH or N; Y is O or S; n is 0 or 1; when n is 1, $R^1$ is connected to the aryl ring at 5, 6, 7, or 8 position; alternatively, when n is 0, $R^1$ is connected to the aryl ring at that 6, 7, or 8 position; a salt, solvate, tautomer, enantiomer, diastereoisomer, or N-oxide thereof, and any combinations thereof; provided that the compound is not selected from the group consisting of 1-(3-(diethylamino)propyl)-3-(3-(dimethylamino)propy)-1-((6-oxo-5,6-dihydro-[1,3]dioxolo[4,5-g]quinolin-7-yl)methyl)thiourea, 1-(2-((2-aminoethyl)(methyl)amino)-4-methylquinolin-6-yl)-3-(3-(4-ethylpiperazin-1-yl)propyl)thiourea; 1-(3-(butyl(ethyl)amino)propyl)-3-(4-methyl-2-(4-methylpiperazin-1-yl)quinolin-6-yl)thiourea; 1-(3-(dipropylamino)propyl)-3-(4-methyl-2-(4-methylpiperazin-1-yl)quinolin-6-yl)thiourea; 3-((2-((2,5-dimethoxyphenyl)amino)quinazolin-4-yl)amino)propan-1-ol; 1-(4-methyl-2-(4-methylpiperazin-1-yl)quinolin-6-yl)-3-(3-(4-methylpiperazin-1-yl)propyl)thiourea, 1-(2-(diethylamino)ethyl)-3-(4-methyl-2-(4-methylpiperazin-1-yl)quinolin-6-yl)thiourea; 2-((2-((2,5-dimethoxyphenyl)amino) quinazolin-4-yl)amino)ethan-1-01; and 3-((2-((2-methoxyphenyl)amino)quinazolin-4-yl)amino)propan-1-ol.

In certain embodiments, in (I) $R^1$ is

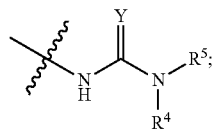

$R^2$ is

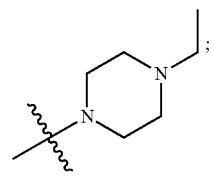 [SMILES: *N1CCN(CC)CC1]

Y is O or S; and each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl.

In certain embodiments, in (I) $R^1$ is

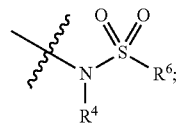

$R^2$ is

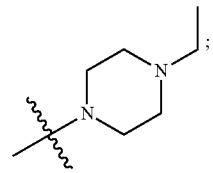 [SMILES: *N1CCN(CC)CC1]

Y is O or S, each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_1$-$C_{10}$)heterocyclyl; and $R^6$ is selected from the group consisting of —($C_1$-$C_6$)alkyl; —($C_1$-$C_6$)heteroalkyl, —$OR^7$, —($C_3$-$C_{10}$)heterocyclyl, aryl, and heteroaryl, wherein the —($C_3$-$C_{10}$)heterocyclyl, aryl or heteroaryl group is optionally substituted.

In certain embodiments, in (I) $R^1$ is

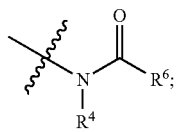

$R^2$ is

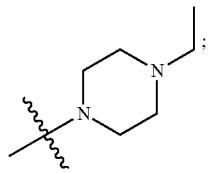 [SMILES: *N1CCN(CC)CC1]

Y is O or S; each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl; aryl, and heteroaryl, wherein the acyl or heteroaryl group is optionally substituted; or, $R^4$ and $R^5$, together with the nitrogen to which $R^4$ and $R^5$ are connected, form a —($C_3$-$C_{10}$)heterocyclyl; and $R^6$ is selected from the group consisting of —($C_1$-$C_6$)alkyl, —($C_1$-$C_6$)heteroalkyl, —$OR^7$, —($C_3$-$C_{10}$)heterocyclyl, aryl, and heteroaryl, wherein the —($C_3$-$C_{10}$)heterocyclyl, aryl or heteroaryl group is optionally substituted.

In certain embodiments, in (I) $R^1$ is

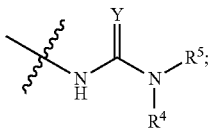

$R^2$ is

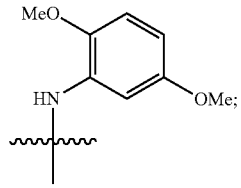 [SMILES: *Nc1cc(OC)ccc1OC]

Y is O or S; and each occurrence of 124 and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl.

In certain embodiments, in (I) $R^1$ is

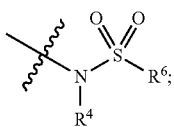

$R^2$ is

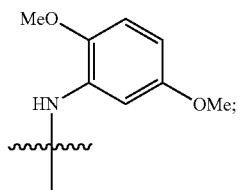 [SMILES: *Nc1cc(OC)ccc1OC]

Y is O or S; each occurrence of $R^4$ and $R^5$ is independently selected from the group consisting of hydrogen, —($C_1$-$C_6$) alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl; $R^6$ is selected from the group consisting of —($C_1$-$C_6$)alkyl, —($C_1$-$C_6$)heteroalkyl; —$OR^7$, —($C_3$-$C_{10}$)heterocyclyl, aryl, and heteroaryl, wherein the —($C_3$-$C_{10}$) heterocyclyl, aryl or heteroaryl group is optionally substituted.

In certain embodiments, in (I) $R^1$ is

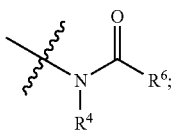

$R^2$ is

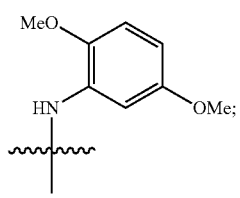 [SMILES: *Nc1cc(OC)ccc1OC]

Y is O or S; each occurrence of $R^4$ and $R^5$ is independently selected from the group consisting of hydrogen, —($C_1$-$C_6$) alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl; $R^6$ is selected from the group consisting of —($C_1$-$C_6$)alkyl, —($C_1$-$C_6$)heteroalkyl; —$OR^7$, —($C_3$-$C_{10}$)heterocyclyl, aryl, and heteroaryl, wherein the —($C_3$-$C_{10}$) heterocyclyl, aryl or heteroaryl group is optionally substituted.

In certain embodiments, the compound is a compound of formula (IX):

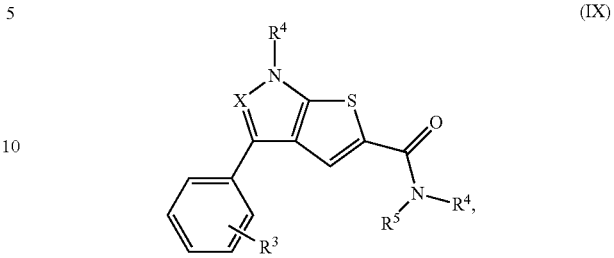

wherein in formula (IX): $R^3$ is selected from the group consisting of hydrogen, —($C_1$-$C_6$)alkyl, —($C_1$-$C_6$)haloalkyl, —($C_1$-$C_6$)heteroalkyl, —F, —Cl, —Br, —I, —CN, —$NO_2$, —$OR^7$, —$SR^7$, —S(=O)$R^7$, —S(=O)$_2R^7$, —C(=O)$R^7$, —OC(=O)$R^7$, and —$CO_2R^7$; each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl; X is N or CH; a salt, solvate, tautomer, enantiomer, diastereoisomer, or N-oxide thereof, and any combinations thereof, provided that the compound is not selected from the group consisting of 3-(4-chlorophenyl)-1-methyl-N-(3-(pyrrolidin-1-yl)propyl)-1H-thieno[2,3-c]pyrazole-5-carboxamide; N-(3-(azepan-1-yl)propyl)-3-(4-chlorophenyl)-1-methyl-1H-thieno [2,3-c]pyrazole-5-carboxamide; N-(2-(butyl(ethyl)amino) ethyl)-3-(4-chlorophenyl)-1-methyl-1H-thieno[2,3-c] pyrazole-5-carboxamide; and 3-(4-chlorophenyl)-1-methyl-N-(3-(4-methylpiperazin-1-yl)propyl)-1H-thieno[2,3-c] pyrazole-5-carboxamide.

In certain embodiments, the compound is selected from the group consisting of: 1-(3-(diethylamino)propyl)-3-(3-(dimethylamino)propyl)-1-((6-oxo-5,6-dihydro-[1,3]dioxolo[4,5-g]quinolin-7-yl)methyl)thiourea; 1-(3,4-dimethoxyphenyl)-N-(3-morpholinopropyl)-9H-pyrido[3,4-b] indole-3-carboxamide; 7-chloro-3-methyl-N-(4-(N-methyl-N-(1-methylpiperidin-4-yl)sulfamoyl)phenyl) benzofuran-2-carboxamide; N-(5-chloro-2-(4-methylbenzoyl) benzofuran-3-yl)-2-(4-methylpiperazin-1-yl)acetamide; N-(3-morpholinopropyl)-1-(p-tolyl)-9H-pyrido[3,4-b]indole-3-carboxamide; 1-(2-((2-aminoethyl) (methyl)amino)-4-methylquinolin-6-yl)-3-(3-(4-ethylpiperazin-1-yl)propyl) thiourea; 1-(3-(butyl(ethyl)amino)propyl)-3-(4-methyl-2-(4-methylpiperazin-1-yl)quinolin-6-yl)thiourea; 1-(3-(dipropylamino)propyl)-3-(4-methyl-2-(4-methylpiperazin-1-yl)quinolin-6-yl)thiourea; 3-((2-((2,5-dimethoxyphenyl) amino) quinazolin-4-yl)amino)propan-1-ol; 1-(4-methyl-2-(4-methylpiperazin-1-yl)quinolin-6-yl)-3-(3-(4-methylpiperazin-1-yl)propyl)thiourea; 1-(2-(diethylamino) ethyl)-3-(4-methyl-2-(4-methylpiperazin-1-yl)quinolin-6-yl)thiourea; 2-((2-((2,5-dimethoxyphenyl)amino) quinazolin-4-yl)amino)ethan-1-ol; 3-(4-chlorophenyl)-1-methyl-N-(3-(4-methylpiperazin-1-yl)propyl)-1H-thieno[2, 3-c]pyrazole-5-carboxamide; N-(2-(butyl(ethyl)amino) ethyl)-3-(4-chlorophenyl)-1-methyl-1H-thieno[2,3-c] pyrazole-5-carboxamide; N-(3-(azepan-1-yl)propyl)-3-(4-chlorophenyl)-1-methyl-1H-thieno[2,3-c]pyrazole-5-carboxamide; 3-(4-chlorophenyl)-1-methyl-N-(3-(pyrrolidin-1-yl)propyl)-1H-thieno[2,3-c]pyrazole-5- carboxamide; 3-((2-((2-methoxyphenyl)amino)quinazolin-4-yl)amino)propan-1-ol; a salt, solvate, tautomer, enantiomer, diastereoisomer, or N-oxide thereof, and any combinations thereof.

In certain embodiments, the method comprises administering to the subject a therapeutically effective amount of at least one compound of the invention. In other embodiments, the method comprises administering to the subject a therapeutically effective amount of at least one compound of formula (I) or (IX).

In certain embodiments, the method further comprises administering to the subject at least one additional therapeutic agent that treats or prevents cancer. In other embodiments, the compound and the at least one additional therapeutic agent are co-administered to the subject. In yet other embodiments, the compound and the at least one additional therapeutic agent are coformulated.

In certain embodiments, the subject is a human.

In certain embodiments, the RAD52 related disease or disorder comprises cancer. In other embodiments, the cancer is selected from the group consisting of squamous cell cancer, lung cancer including small-cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer. In other embodiments, the cancer is ovarian cancer or breast cancer. In other embodiments, the human subject has mutations in BRCA1 and/or BRCA2.

BRIEF DESCRIPTION OF THE DRAWINGS

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIG. 1A illustrates the experimental scheme of fluorescence-quenching assay for the RAD52 ssDNA annealing activity. FLU stands for fluorescein; BHQ 1 stands for black hole quencher 1. DNA substrates contain a mismatch to block spontaneous reaction. FIG. 1B illustrates the kinetics of ssDNA annealing measured on a FluoroMax3 fluorimeter. Shown is the representative result; the reactions were repeated at least three times. FIG. 1C illustrates TAD52 annealing activity in the presence of D-I03 over a range of concentrations, as measured on a FluoroMax3 fluorimeter. FIG. 1D illustrates the scheme of the D-loop assay. RAD52 forms a complex with ssDNA and promotes its homologous pairing with pUC19 plasmid DNA. Asterisk denotes $^{32}$P label on ssDNA. FIG. 1E illustrates the test results of compounds (30 µM) on inhibition of the RAD52 DNA pairing activity. Error bars indicate standard deviation (SD) of the mean.

FIG. 2A illustrates the products of DNA pairing (D-loops) analyzed by electrophoresis in 1% agarose gels. FIG. 2B is a graph illustrating the analyzed data from FIG. 2A. FIG. 2C illustrates the $IC_{50}$ values for certain tested compounds.

FIGS. 7A-7C illustrate the observation that D-I03 inhibits single-strand annealing (SSA), but not homology dependent recombination (HDR)(gene conversion) in U1OS cells. FIG. 7A illustrates the scheme of the SSA-GFP and HDR-GFP reporter systems. The SSA-GFP reporter contains a 5' fragment of the GFP (5'-GFP) gene, and a 3' fragment of the GPF (3'-GFP) with an I-Scel site. The HDR-GFP reporter system contains the GFP gene interrupted by a Sce-I site, and a fragment of the GFP with truncated 3'- and 5'-terminus. FIG. 7B is a graph illustrating the effect of D-I03 on the repair of the 1-SceI-induced DSBs in U2OS cells carrying the chromosomally located SSA-GFP (in red) as well as the effect of D-I03 on formation GFP+ cells after transfection of U2OS cells with pMX-GFP plasmid expressing GFP protein (in green). FIG. 7C is a graph illustrating the effect of D-I03 on the repair of the I-SceI-induced DSBs in U2OS cells carrying the chromosomally located HDR-GFP (in red) as well as the effect of D-I03 on formation GFP+ cells after transfection of U2OS cells with pMX-GFP plasmid expressing GFP protein (in green).

DETAILED DESCRIPTION OF THE INVENTION

Figure 1A:
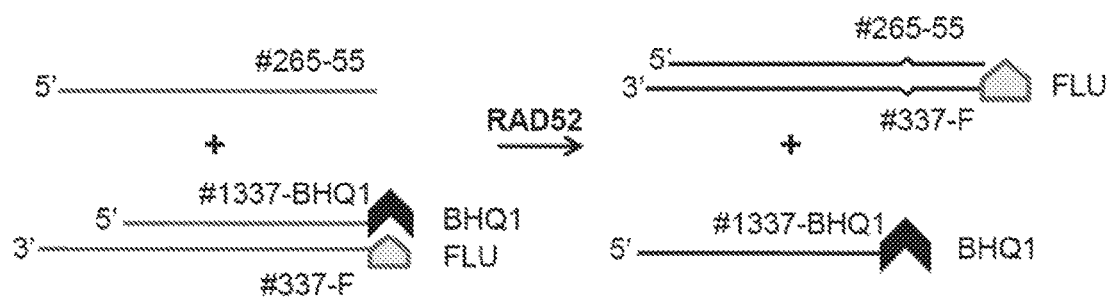
FIGS. 1A-1E illustrate identification and characterization of RAD52 small molecule inhibitors.

The present invention relates to the unexpected discovery of novel compounds that treat or prevent a cancer through inhibition of RAD52 in a mammal. In certain embodiments, the cancer comprises ovarian and/or breast cancer. The present invention also relates to a method for treating or preventing a cancer by administering to a mammal a therapeutically effective amount of a RAD52 inhibitor.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, specific methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in certain embodiments ±5%, in other embodiments ±1%, and in yet other embodiments ±0.1% from the specified value, as such variations are appropriate to perform the disclosed methods.

The term "abnormal," when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics that are normal or expected for one cell or tissue type might be abnormal for a different cell or tissue type.

A disease or disorder is "alleviated" if the severity of a symptom of the disease or disorder, the frequency with which such a symptom is experienced by a patient, or both, is reduced.

The terms "cancer" refers to the physiological condition in a subject typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, as well as head and neck cancer.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "efficacy" refers to the maximal effect ($E_{max}$) achieved within an assay.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the language "pharmaceutically acceptable salt" refers to a salt of the administered compounds prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-toluenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate, powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide, surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "potency" refers to the dose needed to produce half the maximal response ($ED_{50}$).

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a symptom of a condition contemplated herein or the potential to develop a condition contemplated herein, with the purpose to cure, heal, alleviate, relieve, alter, remedy, ameliorate, improve or affect a condition contemplated herein, the symptoms of a condition contemplated herein or the potential to develop a condition contemplated herein. Such treatments may be specifically tailored or modified, based on knowledge obtained from the field of pharmacogenomics.

A "therapeutic" treatment is a treatment administered to a subject who exhibits signs of pathology, for the purpose of diminishing or eliminating those signs.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_1$-$C_6$)alkyl, particularly ethyl, methyl, isopropyl, isobutyl, n-pentyl, n-hexyl and cyclopropylmethyl.

As used herein, the term "substituted alkyl" means alkyl as defined above, substituted by one, two or three substituents selected from the group consisting of halogen, —OH, alkoxy, —$NH_2$, —$N(CH_3)_2$, —C(=O)OH, trifluoromethyl, —C≡N, —C(=O)O($C_1$-$C_4$)alkyl, —C(=O)$NH_2$, —$SO_2NH_2$, —C(=NH)$NH_2$, and —$NO_2$, preferably containing one or two substituents selected from halogen, —OH, alkoxy, —$NH_2$, trifluoromethyl, —$N(CH_3)_2$, and —C(=O)OH, more preferably selected from halogen, alkoxy and —OH. Examples of substituted alkyls include, but are not limited to, 2,2-difluoropropyl, 2-carboxycyclopentyl and 3-chloropropyl.

As used herein, the term "haloalkyl" means alkyl as defined above, substituted by one, two or three substituents selected from the group consisting of F, Cl, Br, and I.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized or substituted. The heteroatom(s) may be placed at any position of the heteroalkyl group, including between the rest of the heteroalkyl group and the fragment to which it is attached, as well as attached to the most distal carbon atom in the heteroalkyl group. Examples include: —O—$CH_2$—$CH_2$—$CH_3$, —$CH_2$—$CH_2$—$CH_2$—OH, —$CH_2$—$CH_2$—NH—$CH_3$, —$CH_2$—S—$CH_2$—$CH_3$, —NH—$(CH_2)_m$—OH (m=1-6). —$N(CH_3)$—$(CH_2)_m$—OH (m=1-6), —NH—$(CH_2)_m$—$OCH_3$ (m=1-6), and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers. Preferred are (C$_1$-C$_3$) alkoxy, particularly ethoxy and methoxy.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e. skeletal atoms) is a carbon atom. In certain embodiments, the cycloalkyl group is saturated or partially unsaturated. In other embodiments, the cycloalkyl group is fused with an aromatic ring. Cycloalkyl groups include groups having from 3 to 10 ring atoms. Illustrative examples of cycloalkyl groups include, but are not limited to, the following moieties:

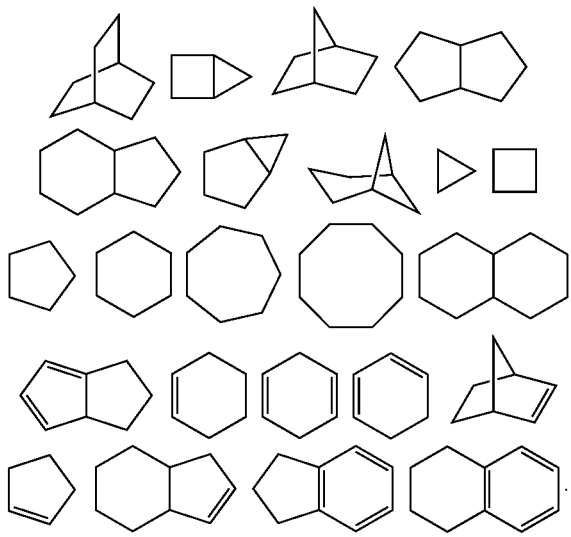

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heterocycloalkyl" or "heterocyclyl" refers to a heteroalicyclic group containing one to four ring heteroatoms each selected from O, S and N. In certain embodiments, each heterocycloalkyl group has from 4 to 10 atoms in its ring system, with the proviso that the ring of said group does not contain two adjacent O or S atoms. In other embodiments, the heterocycloalkyl group is fused with an aromatic ring. In certain embodiments, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

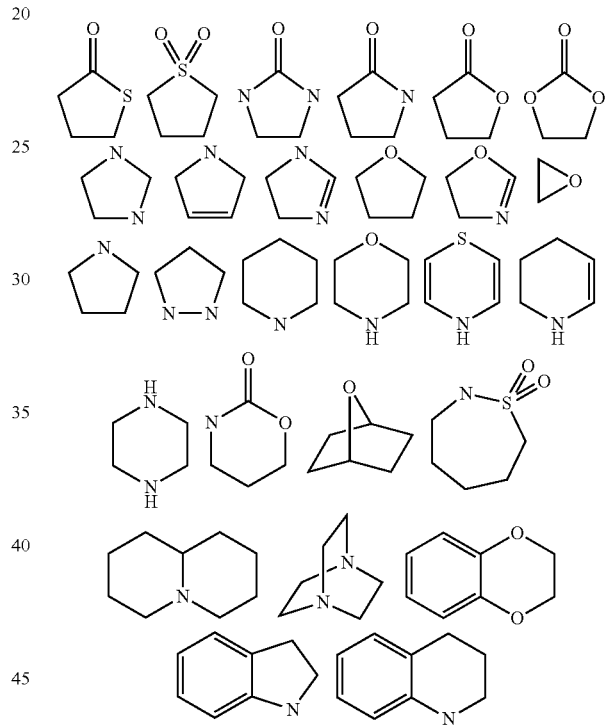

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Preferred is substituted aryl($CH_2$)—. Similarly, the term "heteroaryl-($C_1$-$C_3$)alkyl" means a functional group wherein a one to three carbon alkylene chain is attached to a heteroaryl group, e.g., —$CH_2CH_2$-pyridyl. Preferred is heteroaryl-($CH_2$)—. The term "substituted heteroaryl-($C_1$-$C_3$) alkyl" means a heteroaryl-($C_1$-$C_3$)alkyl functional group in which the heteroaryl group is substituted. Preferred is substituted heteroaryl-($CH_2$)—.

As used herein, the term "heteroaryl" or "heteroaromatic" refers to a heterocycle having aromatic character. A polycyclic heteroaryl may include one or more rings that are partially saturated. Examples include the following moieties:

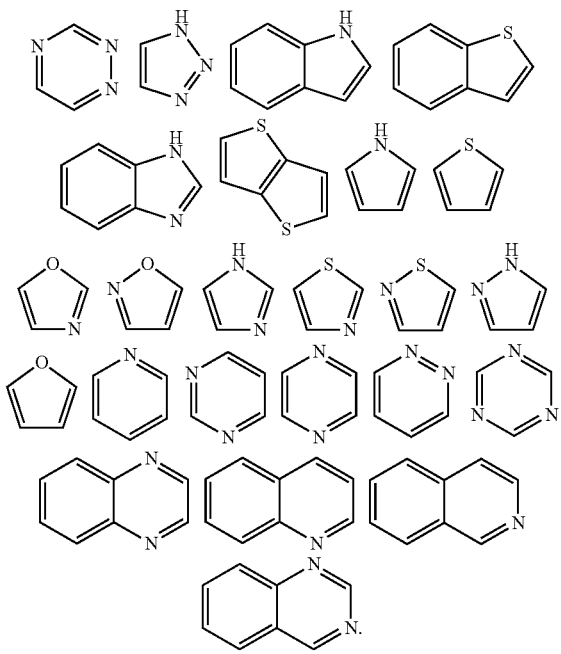

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet other embodiments, the substituents vary in number between one and two.

As used herein, the term "optionally substituted" means that the referenced group may be substituted or unsubstituted. In certain embodiments, the referenced group is optionally substituted with zero substituents, i.e., the referenced group is unsubstituted. In other embodiments, the referenced group is optionally substituted with one or more additional group(s) individually and independently selected from groups described herein.

In certain embodiments, the substituents are independently selected from the group consisting of oxo, halogen, —CN, —$NH_2$, —OH, —$NH(CH_3)$, —$N(CH_3)_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl. $S(=O)_2$alkyl, —$C(=O)NH$[substituted or unsubstituted alkyl, or substituted or unsubstituted phenyl], —$C(=O)N[H$ or alkyl$]_2$, —$OC(=O)N$[substituted or unsubstituted alkyl$]_2$, —$NHC(=O)NH$ [substituted or unsubstituted alkyl, or substituted or unsubstituted phenyl], —$NHC(=O)$alkyl, —$N$[substituted or unsubstituted alkyl]$C(=O)$[substituted or unsubstituted alkyl], —$NHC(=O)$[substituted or unsubstituted alkyl], —$C(OH)$[substituted or unsubstituted alkyl]2, and —$C(NH_2)$[substituted or unsubstituted alkyl]$_2$. In other embodiments, by way of example, an optional substituent is selected from oxo, fluorine, chlorine, bromine, iodine, —CN, —$NH_2$, —OH, —$NH(CH_3)$, —$N(CH_3)_2$, —$CH_3$, —$CH_2CH_3$, —$CH(CH_3)_2$, —$CF_3$, —$CH_2CF_3$, —$OCH_3$, —$OCH_2CH_3$, —$OCH(CH_3)_2$, —$OCF_3$, —$OCH_2CF_3$, —$S(=O)_2$—$CH_3$, —$C(=O)NH_2$, —$C(=O)$—$NHCH_3$, —$NHC(=O)NHCH_3$, —$C(=O)CH_3$, and —$C(=O)OH$. In yet one embodiment, the substituents are independently selected from the group consisting of $C_{1-6}$ alkyl, —OH, $C_{1-6}$ alkoxy, halo, amino, acetamido, oxo and nitro. In yet other embodiments, the substituents are independently selected from the group consisting of $C_1$ alkyl, $C_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula (I), a salt, solvate, tautomer, enantiomer, diastereoisomer, or N-oxide thereof:

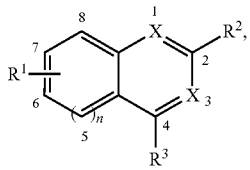

(I)

$R^1$ is selected from the group consisting of:

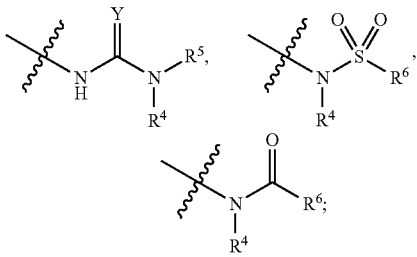

and $R^2$ is $-NR^4R^5$;

$R^3$ is selected from the group consisting of hydrogen, $-(C_1-C_6)$alkyl, $-(C_1-C)$haloalkyl, $-(C_1-C_6)$heteroalkyl. -F. -Cl, -Br, -I, -CN. -NO_2, -OR^7, -SR^7, -S(=O)R^7$. $-S(=O)_2R^7$, $-C(=O)R^7$, $-OC(=O)R^7$, and $-CO_2R^7$;

each occurrence of $R^4$ and $R^5$ is independently selected from the group consisting of hydrogen, $-(C_1-C_6)$alkyl, $-(C_1-C_6)$haloalkyl, $-(C_1-C_6)$heteroalkyl, aryl, and heteroaryl, wherein the aryl or heteroaryl group is optionally substituted; or $R^4$ and $R^5$, together with the nitrogen to which $R^4$ and $R^5$ are connected, form a $-(C_3-C_{10})$heterocyclyl;

each occurrence of $R^6$ is independently selected from the group consisting of $-(C_1-C_6)$alkyl, $-(C_1-C_6)$heteroalkyl, $-OR^7$, $-(C_3-C_{10})$heterocyclyl, aryl, and heteroaryl, wherein the $-(C_3-C_{10})$heterocyclyl, aryl or heteroaryl group is optionally substituted; each occurrence of $R^7$ is independently selected from the group consisting of H, $-(C_1-C_6)$alkyl. $-(C_1-C_6)$heteroalkyl, $-(C_3-C_6)$cycloalkyl, $-(C_3-C_{10})$heterocyclyl, aryl, and $-(C_5-C_{10})$heteroaryl, wherein the alkyl, heteroalkyl, cycloalkyl, heterocyclyl, aryl, or heteroaryl group is optionally substituted;

each occurrence of X is independently CH or N;

Y is O or S;

n is 0 or 1; when n is 1, $R^1$ is connected to the aryl ring at 5, 6, 7, or 8 position; alternatively, when n is 0, $R^1$ is connected to the aryl ring at that 6, 7, or 8 position; provided that the compound is not selected from the group consisting of 1-(3-(diethylamino)propyl)-3-(3-(dimethylamino)propyl)-1-((6-oxo-5,6-dihydro-[1,3]dioxolo[4,5-g]quinolin-7-yl)methyl)thiourea; 1-(2-((2-aminoethyl)(methyl)amino)-4-methylquinolin-6-yl)-3-(3-(4-ethylpiperazin-1-yl)propyl) thiourea 1-(3-(butyl(ethyl)amino)propyl)-3-(4-methyl-2-(4-methylpiperazin-1-yl)quinolin-6-yl)thiourea; 1-(3-(dipropylamino)propyl)-3-(4-methyl-2-(4-methylpiperazin-1-yl)quinolin-6-yl)thiourea; 3-((2-((2,5-dimethoxyphenyl)amino)quinazolin-4-yl)amino)propan-1-ol; 1-(4-methyl-2-(4-methylpiperazin-1-yl)quinolin-6-yl)-3-(3-(4-methylpiperazin-1-yl)propyl)thiourea; 1-(2-(diethylamino)ethyl)-3-(4-methyl-2-(4-methylpiperazin-1-yl)quinolin-6-yl)thiourea; 2-((2-((2,5-dimethoxyphenyl)amino)quinazolin-4-yl)amino)ethan-1-ol; and 3-((2-((2-methoxyphenyl)amino)quinazolin-4-yl)amino)propan-1-ol.

In certain embodiments, the compound of the invention is a compound of formula (I), wherein $R^1$ is

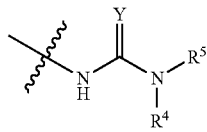

and $R^2$ is

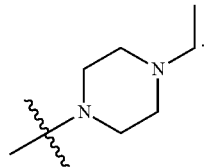 [SMILES: *N1CCN(CC)CC1]

In other embodiments, the compound of the invention is a compound of formula (I), wherein $R^1$ is

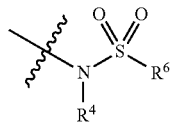

and $R^2$ is

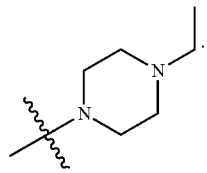 [SMILES: *N1CCN(CC)CC1]

In yet other embodiments, the compound of the invention is a compound of formula (I), wherein $R^1$ is

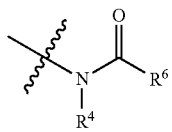

and $R^2$ is

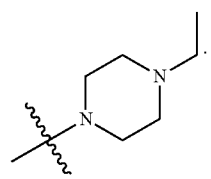

In yet other embodiments, the compound of the invention is a compound of formula (I), wherein $R^1$ is

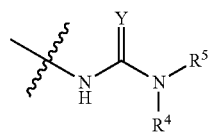

$R^2$ is

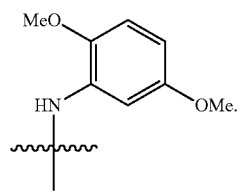 [SMILES: *Nc1cc(OC)ccc1OC]

In yet other embodiments, the compound of the invention is a compound of formula (I), wherein $R^1$ is

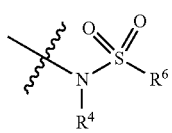

and $R^2$ is

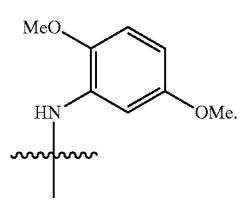 [SMILES: *Nc1cc(OC)ccc1OC]

In yet other embodiments, the compound of the invention is a compound of formula (I), wherein $R^1$ is

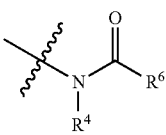

and $R^2$ is

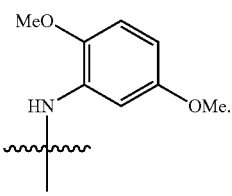 [SMILES: *Nc1cc(OC)ccc1OC]

Exemplary embodiments of compound of the invention include formulas (II)-(VIII), wherein in formula (VII), k is 0, 1, 2, or 3.

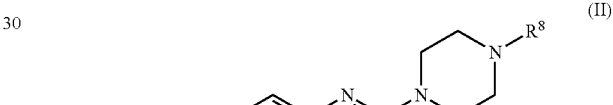

(II)

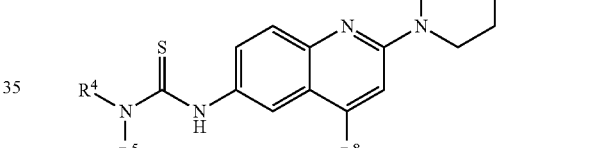

(III)

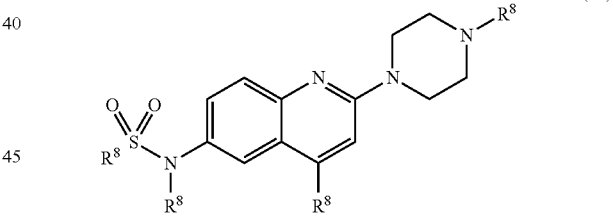

(IV)

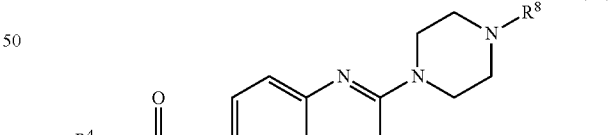

(V)

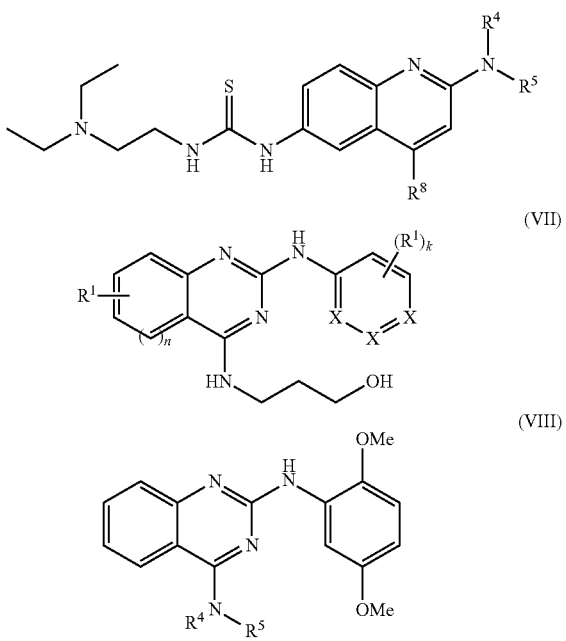

In another aspect, the compound of the invention is a compound of formula (IX), or a salt, solvate, or N-oxide thereof:

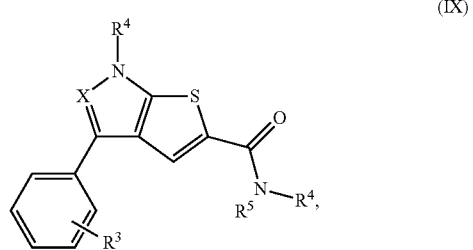

wherein the $R^3$, $R^4$, $R^5$, and X are as defined above; provided the compound is not selected from the group consisting of 3-(4-chlorophenyl)-1-methyl-N-(3-(pyrrolidin-1-yl)propyl)-1H-thieno[2,3-c]pyrazole-5-carboxamide; N-(3-(azepan-1-yl)propyl)-3-(4-chlorophenyl)-1-methyl-1H-thieno[2,3-c]pyrazole-5-carboxamide; N-(2-(butyl(ethyl)amino)ethyl)-3-(4-chlorophenyl)-1-methyl-1H-thieno[2,3-c]pyrazole-5-carboxamide; and 3-(4-chlorophenyl)-1-methyl-N-(3-(4-methylpiperazin-1-yl)propyl)-1H-thieno[2,3-c]pyrazole-5-carboxamide.

The invention further includes a pharmaceutical composition comprising at least one compound of the invention and at least one pharmaceutically acceptable carrier.

Compounds of formulas (I) to (IX) may be prepared by the general schemes described herein, using the synthetic method known by those skilled in the art. The compounds of the invention may possess one or more stereocenters, and each stereocenter may exist independently in either the (R) or (S) configuration. In certain embodiments, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention may exist as tautomers. All tautomers are included within the scope of the compounds presented herein.

In certain embodiments, compounds described herein are prepared as prodrugs. A "prodrug" refers to an agent that is converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with position emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In certain embodiments, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In other embodiments, each protective group is removable by a different means. Protective groups that are cleaved under totally disparate reaction conditions fulfill the requirement of differential removal.

In certain embodiments, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In certain embodiments, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while coexisting amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

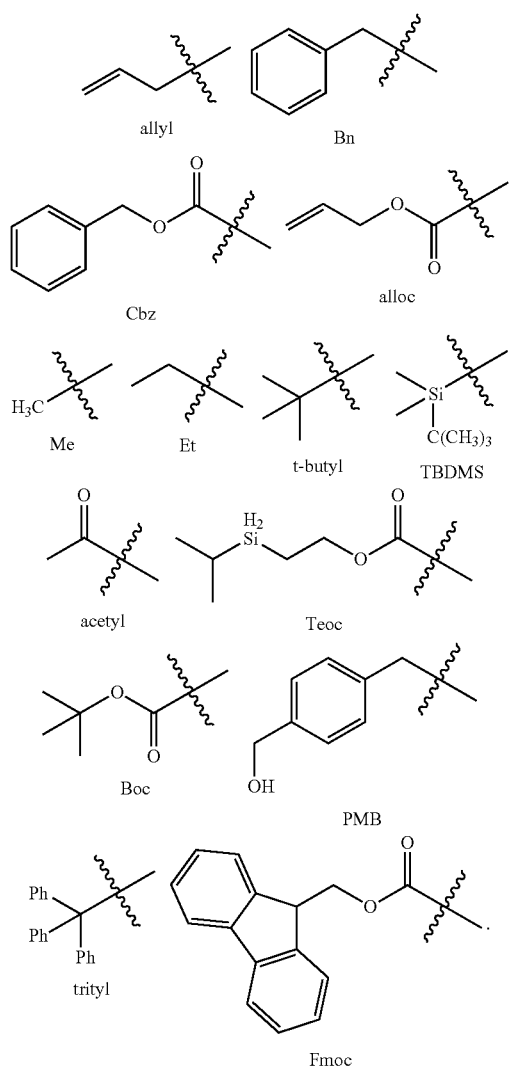

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Compositions

The invention includes a pharmaceutical composition comprising at least one compound selected from the group consisting of a compound of formula (I):

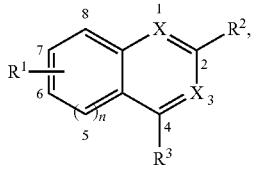
(I)

wherein in formula (I):

R¹ is selected from the group consisting of:

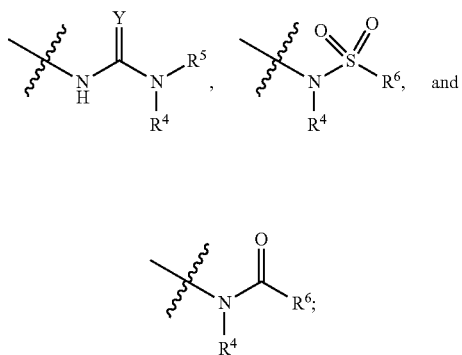

$R^2$ is —$NR^4R^5$;

$R^3$ is selected from the group consisting of hydrogen, —($C_1$-$C_6$)alkyl, —($C_1$-$C_6$)haloalkyl, —($C_1$-$C_6$)heteroalkyl, —F, —Cl, —Br, —I, —CN, —$NO_2$, —$OR^7$, —$SR^7$, —S(=O)$R^7$, —S(=O)$_2R^7$, —C(=O)$R^7$, —OC(=O)$R^7$, and —$CO_2R^7$;

each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl:

each occurrence of $R^6$ is independently selected from the group consisting of —($C_1$-$C_6$)alkyl, —($C_1$-$C_6$)heteroalkyl, —$OR^7$, —($C_3$-$C_{10}$)heterocyclyl, aryl, and heteroaryl, wherein the —($C_3$-$C_{10}$)heterocyclyl, aryl or heteroaryl group is optionally substituted;

each occurrence of $R^7$ is independently selected from the group consisting of H, —($C_1$-$C_6$)alkyl, —($C_1$-$C_6$)heteroalkyl, —($C_3$-$C_6$)cycloalkyl, —($C_3$-$C_{10}$)heterocyclyl, aryl, and —($C_5$-$C_{10}$)heteroaryl, wherein the alkyl, heteroalkyl, cycloalkyl, heterocyclyl, aryl, or heteroaryl group is optionally substituted;

each occurrence of X is independently CH or N;

Y is O or S;

n is 0 or 1; when n is 1, $R^1$ is connected to the aryl ring at 5, 6, 7, or 8 position; alternatively, when n is 0, $R^1$ is connected to the aryl ring at that 6, 7, or 8 position:

a salt, solvate, or N-oxide thereof, and any combinations thereof.

The invention also includes a pharmaceutical composition comprising at least one compound of formula (IX):

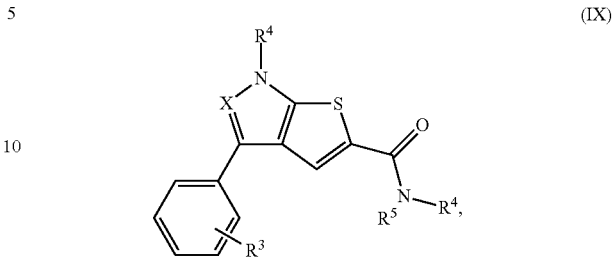
(IX)

wherein in formula (IX):

$R^3$ is selected from the group consisting of hydrogen, —($C_1$-$C_6$)alkyl, —($C_1$-$C_6$)haloalkyl, —($C_1$-$C_6$)heteroalkyl, —F, —Cl, —Br, —I, —CN, —$NO_2$, —$OR^7$, —$SR^7$, —S(=O)$R^7$, —S(=O)$_2R^7$, —C(=O)$R^7$, —OC(=O)$R^7$, and —$CO_2R^7$;

each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted; or $R^4$ and $R^5$, together with the nitrogen to which $R^4$ and $R^5$ are connected, form a —($C_3$-$C_{10}$)heterocyclyl:

X is N or CH, a salt, solvate, or N-oxide thereof, and any combinations thereof.

Methods

The invention includes a method of treating or preventing a cancer by inhibiting RAD52 in a subject in need thereof. Examples of cancers that can be treated or prevented by the present invention include but are not limited to: squamous cell cancer, lung cancer including small-cell lung cancer, non-small cell lung cancer, vulval cancer, thyroid cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer. In certain embodiments, the cancer comprises ovarian or breast cancer.

The method comprises administering to the subject a therapeutically effective amount of a compound of the invention, which is optionally in a pharmaceutical composition. In certain embodiments, the method further comprises administering to the subject an additional therapeutic agent that treats or prevents cancer.

In certain embodiments, administering the compound of the invention to the subject allows for treatment of a subject having mutations in BRCA1 and/or BRCA2. The Examples described herein demonstrate that inhibition of RAD52 caused the death of BRCA-1 and/or BRCA-2 deficient cells.

In certain embodiments, administering the compound of the invention to the subject allows for administering a lower dose of the additional therapeutic agent compared to the dose of the additional therapeutic agent alone that is required to achieve similar results in treating or preventing a cancer in the subject. For example, in certain embodiments, the compound of the invention enhances the anti-cancer activity of the additional therapeutic compound, thereby allowing for a lower dose of the additional therapeutic compound to provide the same effect.

In certain embodiments, the compound of the invention and the therapeutic agent are co-administered to the subject. In other embodiments, the compound of the invention and the therapeutic agent are coformulated and co-administered to the subject.

In certain embodiments, the subject is a mammal. In other embodiments, the mammal is a human.

Combination Therapies

The compounds useful within the methods of the invention may be used in combination with one or more additional therapeutic agents useful for treating a cancer. These additional therapeutic agents may comprise compounds that are commercially available or synthetically accessible to those skilled in the art. These additional therapeutic agents are known to treat, prevent, or reduce the symptoms of a cancer.

In non-limiting examples, the compounds useful within the invention may be used in combination with one or more of the following therapeutic agents: Erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine,dichloroplatinum(II), CAS No. 15663-27-1), carboplatin (CAS No. 41575-94-4), paclitaxel (TAXOL®, Bristol-Myers Squibb Oncology, Princeton, N.J.), pemetrexed (ALIMTA®, Eli Lilly), trastuzumab (HERCEPTIN®, Genentech), temozolomide (4-methyl-5-oxo-2,3,4,6,8-pentazabicyclo[4.3.0]nona-2,79-triene-9-carboxamide, CAS No. 85622-93-1, TEMODAR®, TEMODAL®, Schering Plough), tamoxifen ((Z)-2-[4-(1,2-diphenylbut-1-enyl) phenoxy]-N,N-dimethylethanamine, NOLVADEX®, ISTUBAL®, VALODEX®), and doxorubicin (ADRIAMYCIN®), Akti-1/2, HPPD, rapamycin, oxaliplatin (ELOXATIN®, Sanofi), bortezomib (VELCADE®, Millennium Pharm.), sutent (SUNITINIB®, SU 11248, Pfizer), letrozole (FEMARA®. Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336. Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifamib (ZARNESTRA™, Johnson & Johnson), ABRAXANE™ (Cremophor-free), albumin-engineered nanoparticle formulations of paclitaxel (American Pharmaceutical Partners, Schaumberg, Ill.), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®).

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either prior to or after the onset of a cancer. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a cancer in the patient. An effective amount of the therapeutic compound necessary to achieve a therapeutic effect may vary according to factors such as the state of the disease or disorder in the patient; the age, sex, and weight of the patient; and the ability of the therapeutic compound to treat a cancer in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated, each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a cancer in a patient.

In certain embodiments, the compositions of the invention are formulated using one or more pharmaceutically acceptable excipients or carriers. In certain embodiments, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5.000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the invention is from about 1 mg and about 2,500 mg. In some embodiments, a dose of a compound of the invention used in compositions described herein is less than about 10,000 mg, or less than about 8.000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a cancer in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents. e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery, Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present invention depends on the age, sex and weight of the patient, the current medical condition of the patient and the progression of a cancer in the patient being treated. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously, alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the viral load, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50%/o of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Methods and Materials
Biochemical Assays

The effect of inhibitors was tested during HTS using DNA fluorescent substrates. The compounds were re-tested using radioactively labeled substrates, and the IC50s are shown in Table 1.

The selectivity test was run against RAD51 that is structurally unrelated to RAD52, but displaying similar activities. The test was run at compound concentrations=10× of IC50. The selectivity data was shown in Table 1. Compounds that showed more than 50% inhibition were discarded.

Cellular Assays

Cell Lines:
1. BRCA1 deficient/proficient cell line: UWB1.298/ UWB1.298 (BRCA1+).

2. BRCA2 deficient/proficient cell line:
Protocol:

BxPC3 cells were kept in RPMI 1640 (ATCC) media supplemented with 10% FBS (Gibco). Capan-1/BxPC3 Capan-1 cells were kept in IMDM (ATCC) media containing 20% FBS (GIBCO). UWB1.298 and UWB1.298 (BRCA1+) cells were kept in 48.5% RPMI1640 (ATCC), 48.5% MEGM (Clonetics/Lonza, MEGM kit, CC-3150) and 3% FBS (GIBCO) respectively. Cells in log-phase were harvested and 100 μl cell suspensions were replated in a 96-well plate with a final density of 4000 cells/well. After overnight growth, cells were treated with indicated concentrations of compounds. Media containing the invariant concentration of compounds were refreshed every 3 days until cells were finally lysed by 30 μl/well of Promega CellTiter-Glo reagents and read on a Promega GloMax 96 reader on day 10 (9 days exposure).

Promega CellTiter-Glo protocol is available on the web: www dot promega dot com/resources/protocols/technical-bulletins/0/celltiter-gloluminescent-cell-viability-assay-protocol/.

Chemicals, Proteins, and DNA

Cisplatin was purchased from Sigma-Aldrich. Human RAD52 and RAD51 were purified as described (Bugreev et al., 2005, Mol. Cell. Biol. 33, 387-395). The oligonuclotides (Table 2) were purchased from IDT, Inc and further purified by electrophoresis (Rossi et al., 2010, Methods 51, 336-346). Supercoiled pUC19 plasmid DNA was purified using Qiagen kits. All DNA concentrations are expressed as moles of nucleotide.

Compound Libraries, and Compounds

A Broad's diversity-oriented synthesis (DOS) library having 93,672 compounds and a Molecular Libraries Probe Center Network (MPLCN) library having 279,231 compounds were used. All the compounds were dissolved in DMSO (Sigma. Cat #D8418). In the working solutions the DMSO concentration added with the stock of compounds was 2% (v/v), unless indicated otherwise. The compounds for confirmation analysis were purchased from Asinex Ltd., ChemBridge Co., ChemDiv Inc, Enamine, FCH Group, Frontier Scientific Services Inc., InterBioScreen Ltd., Life Chemicals Inc., Scientific Exchange Inc., Sigma-Aldrich Co., and Vitas-M Laboratory Ltd.

Fluorescence-Quenching Assay for RAD52 DNA Annealing

Tailed dsDNA substrate was prepared by thermal annealing of ssDNA oligonucleotides 337-F and 1337-BHQ1 (SEQ ID NO: 2) containing Fluorescein and Black Hole Quencher 1 residues at the 5' and 3' end, respectively. DNA annealing was initiated by adding RAD52 (20 nM) to the mixture of ssDNA oligonucleotide 265-55 (SEQ ID NO: 3) (5 nM, molecules) and tailed dsDNA 337-F/1337-BHQ1 (SEQ ID NO: 2) (5 nM, molecules) in buffer containing 25 mM Tris-acetate pH 7.5, 100 μg·ml−1 BSA and 1 mM DTT. The fluorescence intensity was measured in a 3-mm quartz cuvette (Stama Cells) using a FluoroMax-3 (HORIBA) fluorimeter with 492 nm excitation wavelength and 520 nm emission wavelength at 30° C. for at least 2000 s.

HIS for RAD52 Inhibitors

The fluorescence-quenching assay for RAD52-promoted DNA annealing was optimized to a 4 μl 1536 well protocol using 25 nM RAD52 and 8 nM (molecules) DNA in buffer containing 25 mM Tris-acetate pH 7.5, 100 μg·ml−1 BSA, 1 mM DTT, and 0.01% Pluronic F-68. Wells containing no RAD52 were used as a positive control to estimate the activity of fully inhibited protein; wells in which the compounds were replaced with only the vehicle (DMSO) were used as neutral control. The HTS was performed using the 8 channel BioRAPTR 1536 (Beckman) for reagent dispensing. The reactions were carried out for 30 minutes followed by measurement of an endpoint fluorescence (485 nm excitation, 535 nm emission) using an EnVision multimode plate reader (Perkin Elmer). Wells containing no RAD52 enzyme were used to as positive control, and data were analyzed using Genedata. The compounds with an inhibitory effect of 30% or greater were tested further by measuring the concentration dependence (in a range from 1 nM to 100 μM) of their inhibition of RAD51. The most potent inhibitory compounds were analyzed further using non-fluorescent assays. Detailed methods for RAD52 screening are in PubMed: pubchem dot ncbi dot nlm dot nih dot gov/assay/assay dot cgi?aid=651660.

D-Loop Formation by RAD52 or RAD51

To form RAD52 nucleoprotein complexes, RAD52 (0.45 μM) was incubated with a $^{32}$P-labeled ssDNA (oligo 90/SEQ ID NO: 4) (3 μM, nt) in buffer containing 25 mM Tris-Acetate, pH 7.5, 100 μg·ml−1 BSA, 0.3 mM magnesium acetate, and 2 mM DTT at 37° C. for 15 min. To form RAD51 nucleoprotein filament, RAD51 (1 μM) was incubated with $^{32}$P-labeled ssDNA (3 μM, nt) in buffer containing 25 mM Tris-Acetate, pH 7.5, 100 μg·ml−1 BSA, 1 mM calcium chloride, 1 mM ATP and 2 mM DTT for 15 min at 37° C. Then inhibitors were added to both reactions and incubation continued for 15 min at 37° C. D-Loop formation was initiated by addition of supercoiled pUC19 DNA (50 μM, nucleotides) and was carried out 15 min at 37° C. The reactions were stopped and deproteinized by the addition of 1.5% SDS and proteinase K (0.8 mg/ml) for 15 min at 37° C., mixed with a 0.10 volume of loading buffer (70% glycerol, 0.1% bromphenol blue), and analyzed by electrophoresis in 1% agarose gels in TAE buffer (40 mM Tris acetate, pH 8.3, and 1 mM EDTA) at 5 V/cm for 3 h. The gels were dried on DEAE-81 paper (Whatman) and the yield of D-loops quantified using a Storm 840 PhosphorImager and ImageQuant 5.2 (GE Healthcare). The D-loop yield was expressed as a percentage of plasmid DNA carrying D-loops relative to the total plasmid DNA.

Calculation of the $IC_{50}$ Value for RAD52 Inhibitors $IC_{50}$ values were calculated using GraphPad Prism V5.0 software. The data were obtained from three independent repeats of experiments.

Acridine Orange Displacement Assay for DNA Binding

The selected compounds were tested their abilities to bind DNA to rule out DNA binding as an undesired mechanism of action. The compounds in varied concentrations were added into 30 μl reaction mixtures containing 50 nM acridine orange and 6 μg/ml salmon sperm DNA, 10 mM HEPES, pH 7.5; 1 mM EDTA pH 7.5; 100 mM NaCl in 384-well plates, and the reactions were incubated at room temperature for 20 min followed by fluorescence polarization measurement using an EnVision (Perkin Elmer) equipped with a 480 nm excitation filter and 535 nm S and P emission filters with a D505 FP/D535 dichroic mirror. Mitoxantrone (10 μM) was used as a positive control. The S and P values are processed with the standard fluorescence polarization calculation formula ($mP=1000*(S-G*P)/(S+G*P)$) where G is the G-factor and is approximately 1.

Luminescent Cell Viability Assay

BxPC3 cells were kept in RPMI 1640 (ATCC) media supplemented with 10% FBS (Gibco); Capan-1 cells were kept in IMDM (ATCC) media containing 20% FBS (GIBCO); UWB1.298 and UWB1.298 (BRCA1+) cells were kept in 48.5% RPMI1640 (ATCC), 48.5% MEGM (Clonetics/Lonza, MEGM kit, CC-3150) and 3% FBS (GIBCO) respectively. Cells in log-phase were harvested and 100 μl cell suspensions were replated in a 96-well plate with a final density of 4000 cells/well. After overnight growth, cells were treated with indicated concentrations of compounds. Media containing the invariant concentration of compounds were refreshed every 3 days until cells were finally lysed by 30 μl/well of Promega CellTiter-Glo reagents and read on a Promega GloMax 96 reader on day 10 (9 days exposure). Promega CellTiter-Glo protocol is available on the web: www dot promega dot com/resources/protocols/technical-bulletins/0/celltiter-glo-luminescent-cell-viability-assay-protocol/

Clonogenic Survival Assay

MDA-MB-436 cells were cultured in RPMI+10% FBS. BRCA-proficient and BRCA-deficient cells were plated on day 0 in triplicate at 5,000 cells/well. On days 1 and 3, the cells were treated with 0, 2.5 uM, 5 uM, or 10 uM of D-I03 or 109. Cells were counted on day 4 on a hemocytometer, using Trypan Blue exclusion, and immediately were plated in a clonogenic assay at a density of 500 cells/well in a 6 well plate, in RPMI+10% FBS. After two weeks, the colonies were fixed/stained with 0.05% of 10 mg/ml ethidium bromide in 50% ethanol and visualized with Alphaimager gel imager (Alpha Innotech).

CML Viability Assay

Lin-CD34+ primary CML and normal cells were obtained by magnetic sorting using the EasySep negative selection human progenitor cell enrichment cocktail followed by treatment with human CD34 positive selection cocktail (StemCell Technologies), and were subsequently cultured in StemSpan H3000 media (StemCell Technologies) supplemented with a cocktail of growth factors (100 ng/ml stem cell factor, 20 ng/ml interleukin3 [IL-3], 100 ng/ml fins-related tyrosine kinase 3 ligand, 20 ng/ml granulocyte colony-stimulating factor, 20 ng/ml IL-6). For the viability assay, CD34+ CML (n=3) and normal (n=5) cells were plated at $1 \times 10^4$ cells/well in 96 well plates on day 0, and treated with 0 μM, 2 μM, 5 μM, or 10 μM D-I03 on days 0 and 2. Viable cells were counted on day 4 using Trypan Blue staining.

Measurement of Compound Binding to RAD52 by SPR

Experiments were performed using the ProteOn XPR36 SPR array system (Bio-Rad). ProteOn GLH sensor chips were preconditioned with two short pulses each (10 s) of 50 mM NaOH, 100 mM HCl, and 0.5% SDS. Then the system was equilibrated with PBS-T buffer (20 mM Na-phosphate, 150 mM NaCl, and 0.1% polysorbate 20, pH 7.4). Individual ligand flow channels were activated for 5 min at 25° C. with a mixture of 1-ethyl-3-[3-dimethylamino propyl carbodiimide hydrochloride) (0.2 M) and sulfo-N-hydroxy succinimide (0.05 M). Immediately after chip activation, either RAD52 (100 μg·ml−1 in 25 mM Tris-Acetate, 20 mM KCl, 0.3 mM magnesium acetate, pH 7.5) or the anti-HIV mAb 2F5 (100 μg·ml−1 in 10 mM sodium acetate, pH 5.0) was injected across ligand flow channels for 5 min at a flow rate of 30 μl·min$^{-1}$.

Excess active ester groups on the sensor surface were capped by a 5-min injection of 1 M ethanolamine HCl (pH 8.5). This resulted in the coupling of RAD52 and 2F5 at a density of 9,000 RUs (response unit, which is an arbitrary unit that corresponds to 1 pg/mm$^2$). The standard deviation in the immobilization level from the six spots within each channel was less than 4%. Compounds in indicated concentrations in 25 mM Tris-Acetate, 20 mM KCl, 0.3 mM magnesium acetate, pH 7.5, supplemented with 0.005% polysorbate 20 and 2% DMSO were injected over the control and RAD52 surfaces at a flow rate of 200 μl min-1, for either a 30 s (D-I09) or 1-min association phase (D-I03, D-G23), followed by a variable dissociation phase at 25° C. using the "one-shot" functionality of the ProteOn (Bravman et al., 2006, Anal Biochem 358, 281-288).

Specific regeneration of the surfaces between injections was not needed owing to the nature of the interaction. Data were analyzed using the ProteOn Manager Software version 3.0 (Bio-Rad). The responses of a buffer injection and responses from the reference flow cell were subtracted to account for nonspecific binding. Experimental data were fitted globally to a simple 1:1 binding model. The average kinetic parameters (association [ka] and dissociation [kd] rates) generated from three data sets were used to define the equilibrium dissociation constant (KD). Data that could not be adequately fit to a binding model were analyzed using equilibrium analysis, plotting the response at equilibrium versus concentration and fitting to a steady state model.

Measuring the Effect of Inhibitors on GFP-RAD52 and RAL51 Foci Formation

GFP-RAD52 foci formation was measured in BCR-ABL1-positive BRCA1-deficient 32Dcl3 murine hematopoietic cell line that expresses GFP-RAD52 (Cramer-Morales et al., 2013, Blood 122, 1293-1304). RAD51 foci formation was measured in parental 32Dcl3.

Both cell lines were cultured in IMDM plus 10% FBS. The cells were plated at 500,000 cells/ml and pretreated for 4 h with either D-G23 or D-I03 (2.5 μM) for GFP-RAD52 foci or with D-I03 (2.5 μM) for RAD51 foci (or no pretreatment for the control and cisplatin-treated cells). After 4 h of incubation, the cells were treated with 3 μg/mL cisplatin for 16 h. Following cisplatin treatment, cytospins were prepared using polylysine coated slides (Thermo Scientific). DNA was counterstained with DAPI. To detect RAD51 foci, cells were stained with an anti-RAD51 antibody (Thermo Scientific), followed by a secondary antibody conjugated with AlexaFluor 594. RAD51 and GFP-RAD52 foci were visualized with an inverted Olympus IX70 fluorescence microscope equipped with a Cooke Sensicam QE camera (The Cooke Co., Auburn Hills, Mich., USA). Images from 25-60 cells/group were processed using SlideBook 3.0 (Intelligent Imaging Innovation).

Measuring the Effect of D-I03 on Single-Strand Annealing (SSA) and Gene Conversion (HDR) in U2OS Cells U2OS cells with chromosomally integrated SSA (U2OSSSA) or gene conversion HDR(U20S-HDR)-reporter were cultured in DMEM (Sigma D-6429) containing 10% FBS (Gibco) supplemented with antibiotics (penicillin 100 U/ml, streptomycin 100 ] g/ml, and plasmocin (2.5 μg/ml). At 80% confluence, cells were trypsinized and plated in triplicate at a density of $2 \times 10^5$ cells/well in 6 well plates. After 22 h cells were washed with IX PBS and further incubated for 2 h in antibiotic-free DMEM-10% FBS. Cells were transfected with pCBASce (0.8 μg) expressing I-SceI endonuclease or, in controls, with pUC19 (0.8 pig) or pMXGFP (0.8 μg) plasmids using Lipofectamine 2000. After 3 h of transfection, cells were washed with antibiotic-free DMEM-10% FBS. Then, cells were incubated in DMEM-10% FBS supplemented with antibiotics and containing D-I03 at indicated concentrations followed by additional incubation for 48 h. In each well, cells were washed with 1×PBS, trypsinized and fixed with 3.3% formaldehyde. Fixed cells were kept on ice. The yield of GFP+ positive cells was measured by flow cytometry using Guava EasyCyte PRO (EMD Millipore).

Example 1: High Throughput Screening (HTS) for RAD52 Inhibitors

Figure 1B:
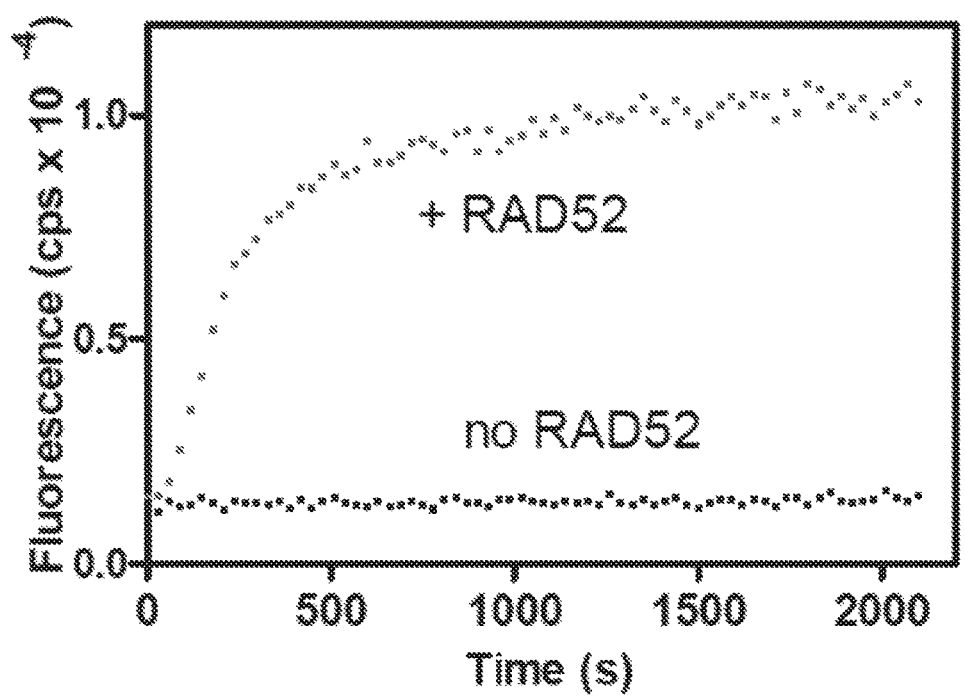
Figure 1C:
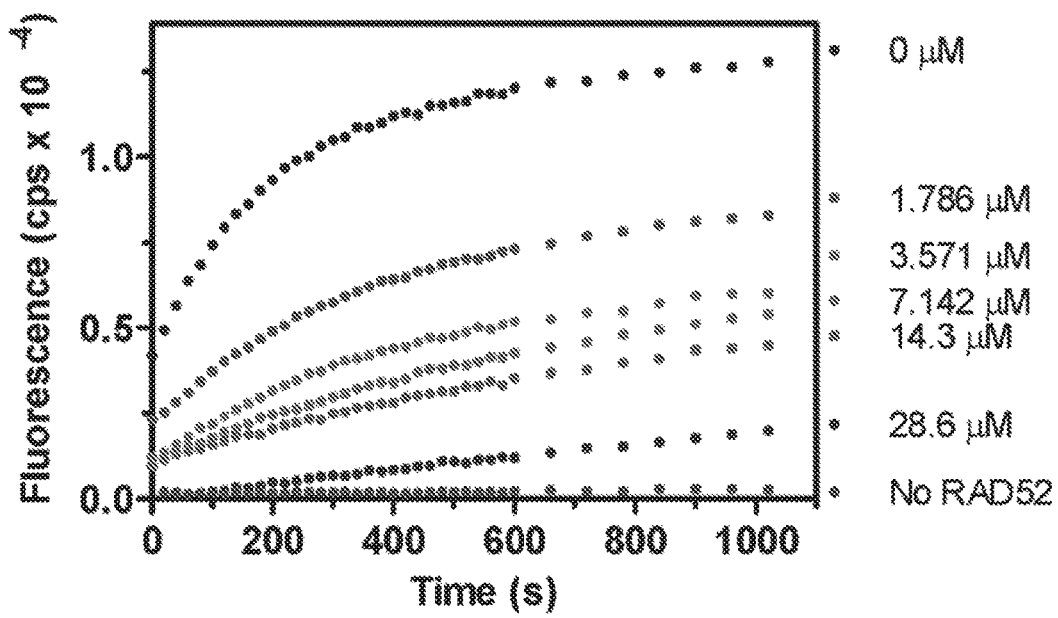
Figure 1D:
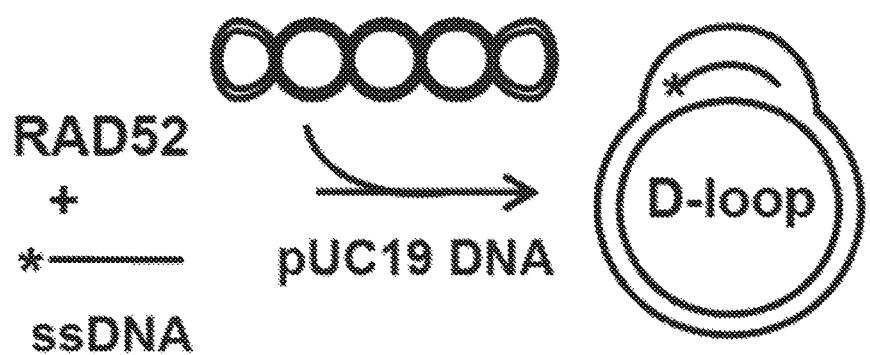

Small molecule inhibitors of RAD52 were discovered using high throughput screening (HTS) of compound libraries. In vitro, RAD52 carries out annealing of complementary ssDNA molecules and an invasion of ssDNA into homologous duplex DNA. A fluorescence-quenching assay was used to screen for inhibitors of RAD52 ssDNA annealing activity (FIGS. 1A-1E). In this assay, RAD52 promotes DNA annealing between homologous synthetic ssDNA (Oligo 265-55; 55 nt/SEQ ID NO: 3) and tailed dsDNA (tdsDNA) substrates. The tdsDNA was generated by thermal annealing of an ssDNA 60-mer (Oligo 337-FLU, SEQ ID NO: 1) carrying fluorescein (FLU), a fluorescence donor group, and an ssDNA 39-mer (1337-BHQ1/SEQ ID NO: 2) carrying black hole quencher 1 (BHQ1), a non-fluorescent acceptor group (FIG. 1A). Annealing promoted by RAD52 between ssDNA and tdsDNA led to displacement of the FLU-carrying DNA strand from the tdsDNA and in an increase in fluorescence due to secession of fluorescence quenching by the BHQ1 group (FIG. 1B).

The fluorescence-quenching assay was optimized for 1,536 well plates (Z' Avg=0.64). The primary HTS of the 372,903-compound library yielded 1,687 positive hits that caused more than 30% inhibition of the RAD52-dependent fluorescence increase (0.5% activities), including 628 hits in a 93,672-compound Broad's diversity-oriented synthesis (DOS) library (0.7% activities) and 1,115 hits in a 279,231-compound Molecular Libraries Probe Center Network (MPLCN) library (0.4% Activities). The hits were further analyzed for a concentration dependence in inhibiting of RAD52 and by testing their DNA binding affinity using the acridine orange assay. As a result, 187 compounds were identified that inhibited RAD52 with the $IC_{50}$ lower than 10 µM and displayed no DNA binding. These remaining compounds were assessed for their potential chemical tractability by removing compounds with highly reactive or unstable functional groups and focusing on chemotypes that were synthetically accessible and attractive. The selected compounds as well as some closely related new analogs of certain hits were next purchased as dry powders from commercial sources. After executing this selection process, 70 compounds were obtained for further analyses.

Figure 1E:
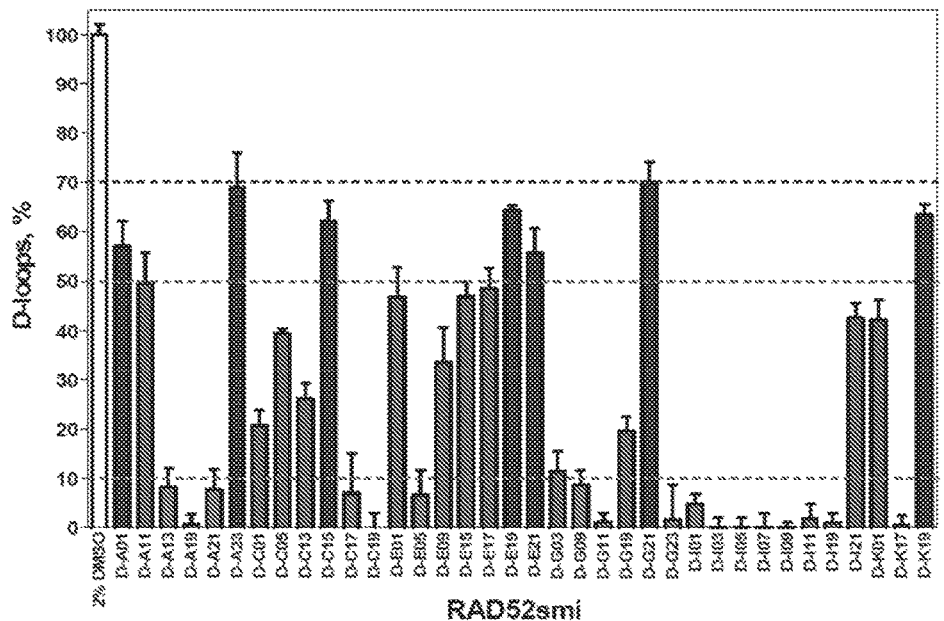
Figure 2A:
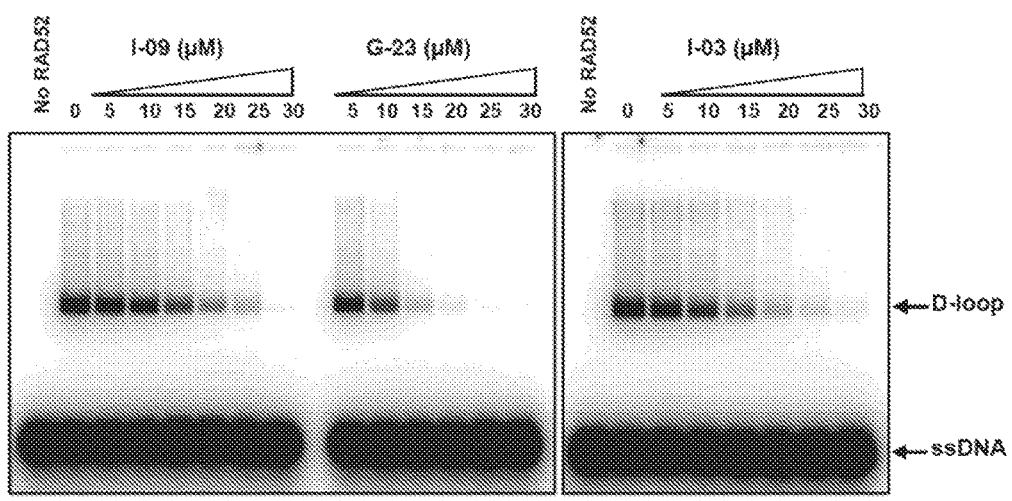
FIGS. 2A-2C illustrate the effect of inhibitors on DNA pairing activity of RAD52.
Figure 2B:
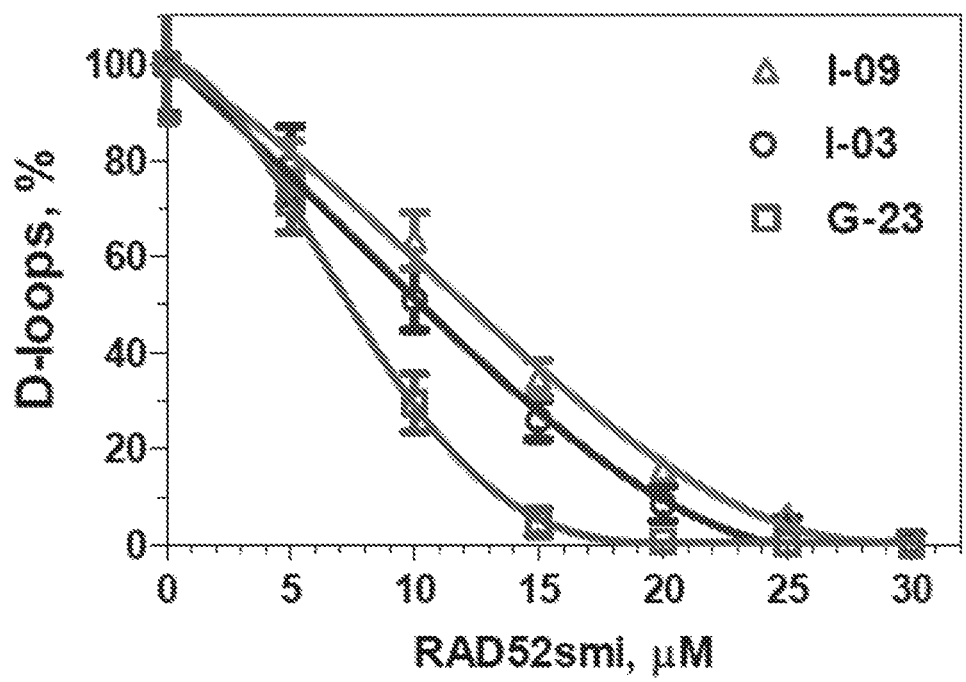
Figure 2C:
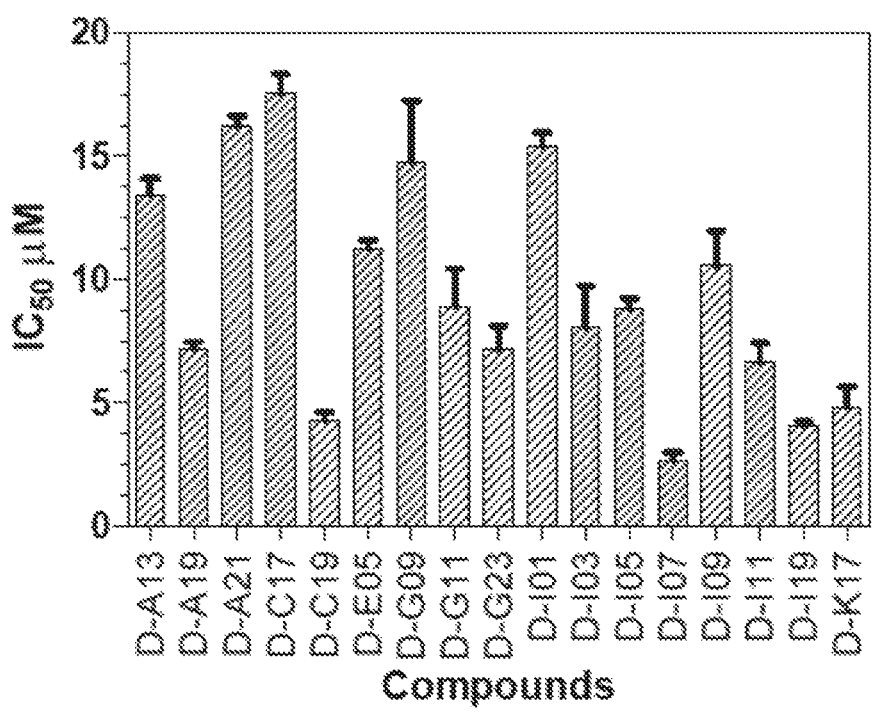

The inhibitory effect of the 70 selected compounds were tested using the D-loop assay, in which RAD52 promotes pairing between 32P-labeled ssDNA and homologous supercoiled plasmid pUC19 DNA (FIG. 1D); the product of the reaction, D-loops, were analyzed by electrophoresis in 1% agarose gels. First, by testing the effect of the selected compounds at fixed (30 µM) concentration, 17 compounds were identified to inhibit D-loop formation by more than 90% (FIG. 1E). Then, the effects of each of the 17 compounds on RAD52-dependent D-loop formation were measured in a concentration dependent manner. The $IC_{50}$ of these compounds varied in a range between 2.7 µM and 17.5 µM (FIG. 2A-2C; Tables 1 and 4). In the D-loop assay the $IC_{50}$ values were generally higher than in the fluorescence-quenching assay likely due to the higher RAD52 concentration employed by the former assay, 450 nM vs 25 nM.

Figure 2D:
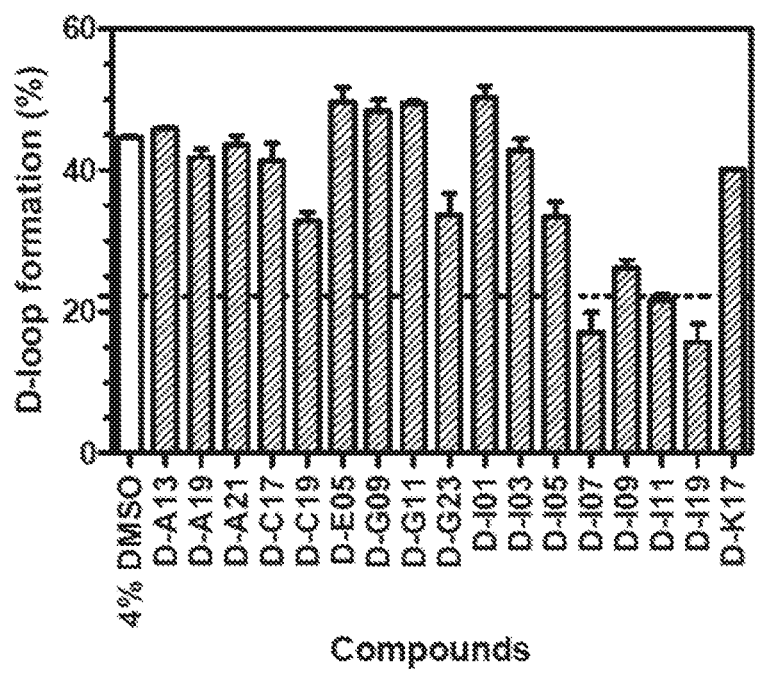
FIG. 2D illustrates the effects of the RAD52 inhibitors on DNA pairing activity of RAD51. The effects of inhibitors were measured using the D-loop assay at the inhibitors concentrations that correspond to their 10×$IC_{50}$ values for RAD52 pairing activity. Error bars indicate SD of the mean.
Figure 3A:
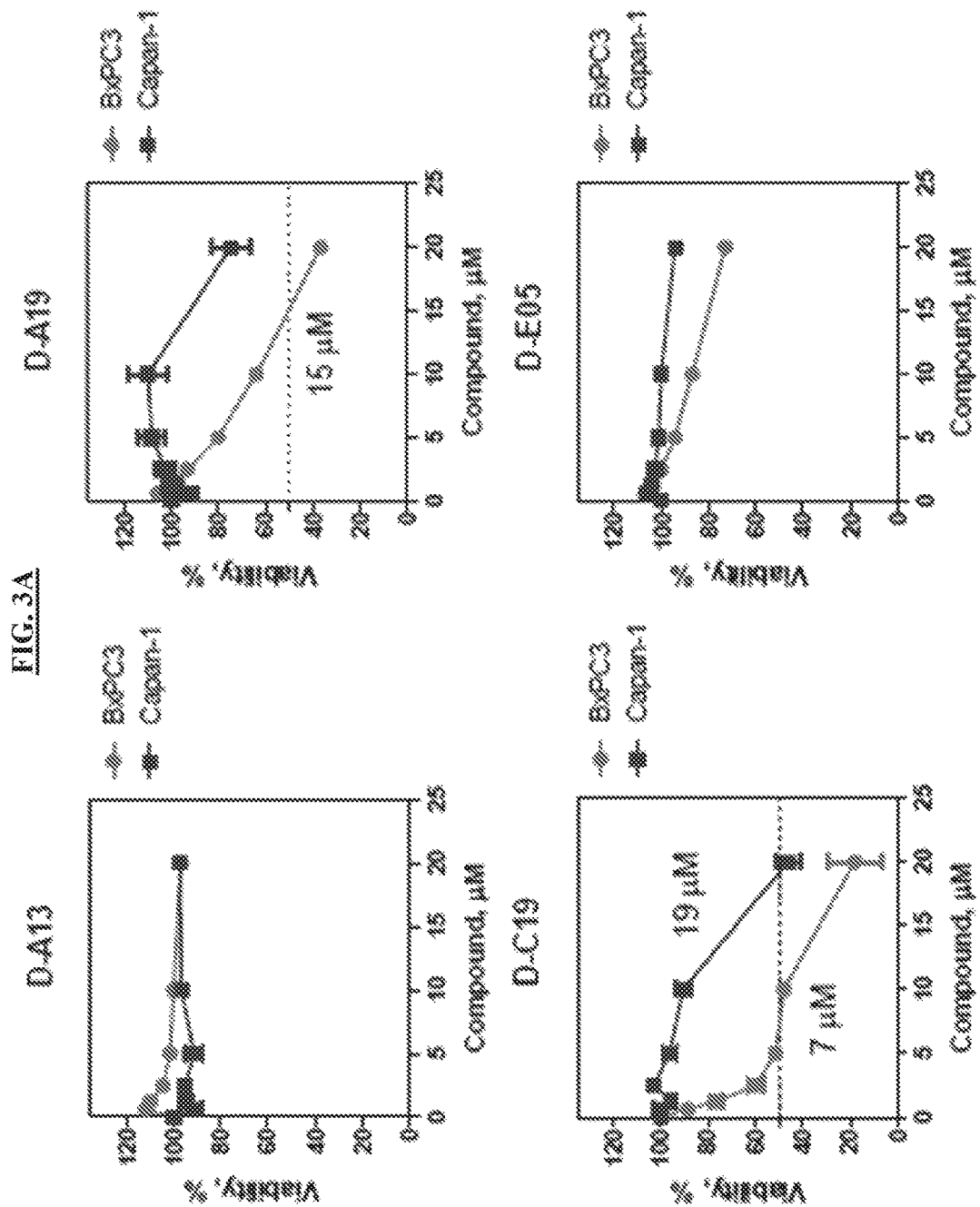
FIGS. 3A-3D illustrate the effects of the RAD52 inhibitors on survival of Capan-1 (BRCA2$^-$) and BxPC3 (BRCA2$^+$) cells. Capan-1 is denoted by the line of dots; BxPC3 is denoted by the line of squares. The experiments were repeated at least three times. Error bars indicate SD of the mean.
Figure 3B:
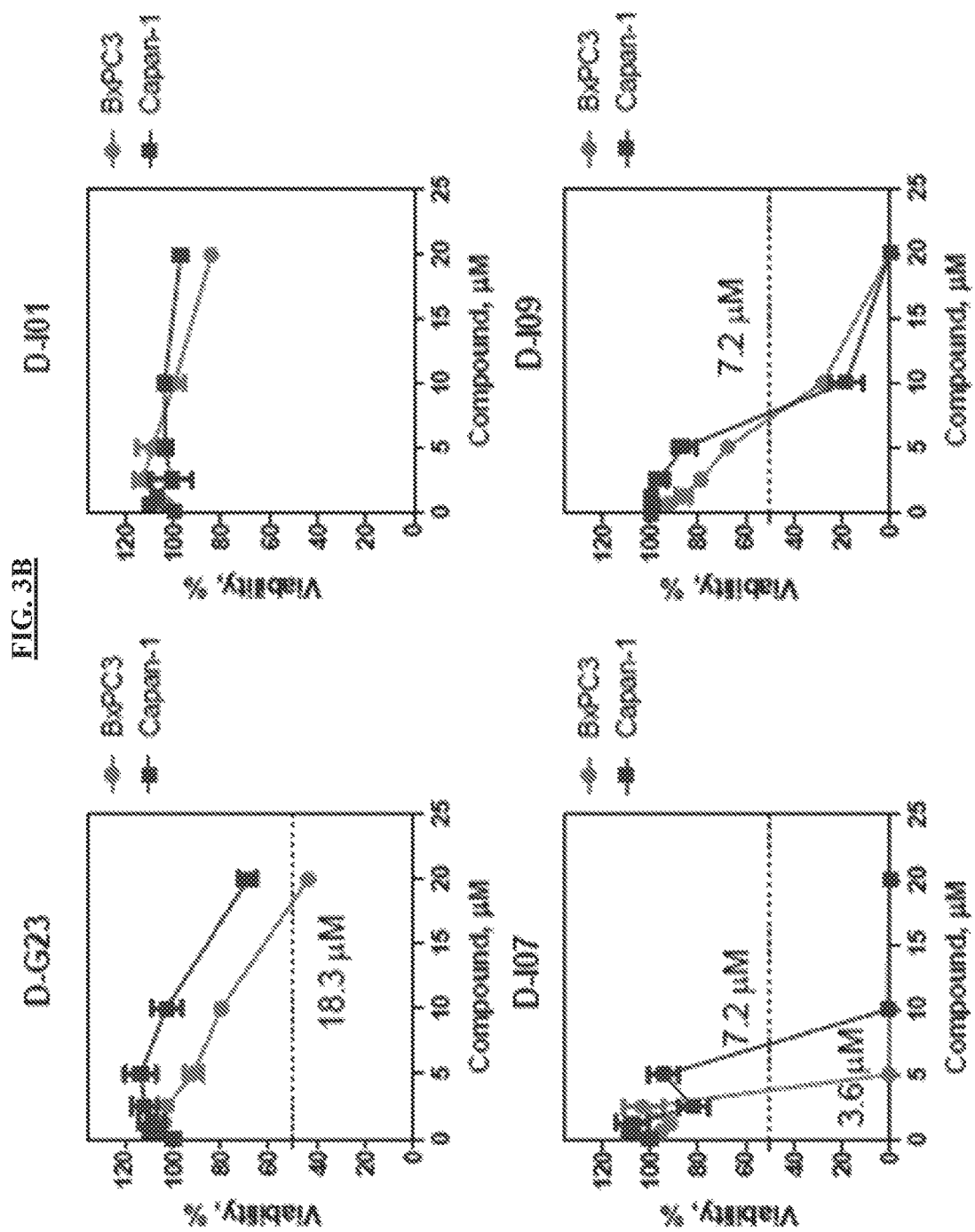
Figure 3C:
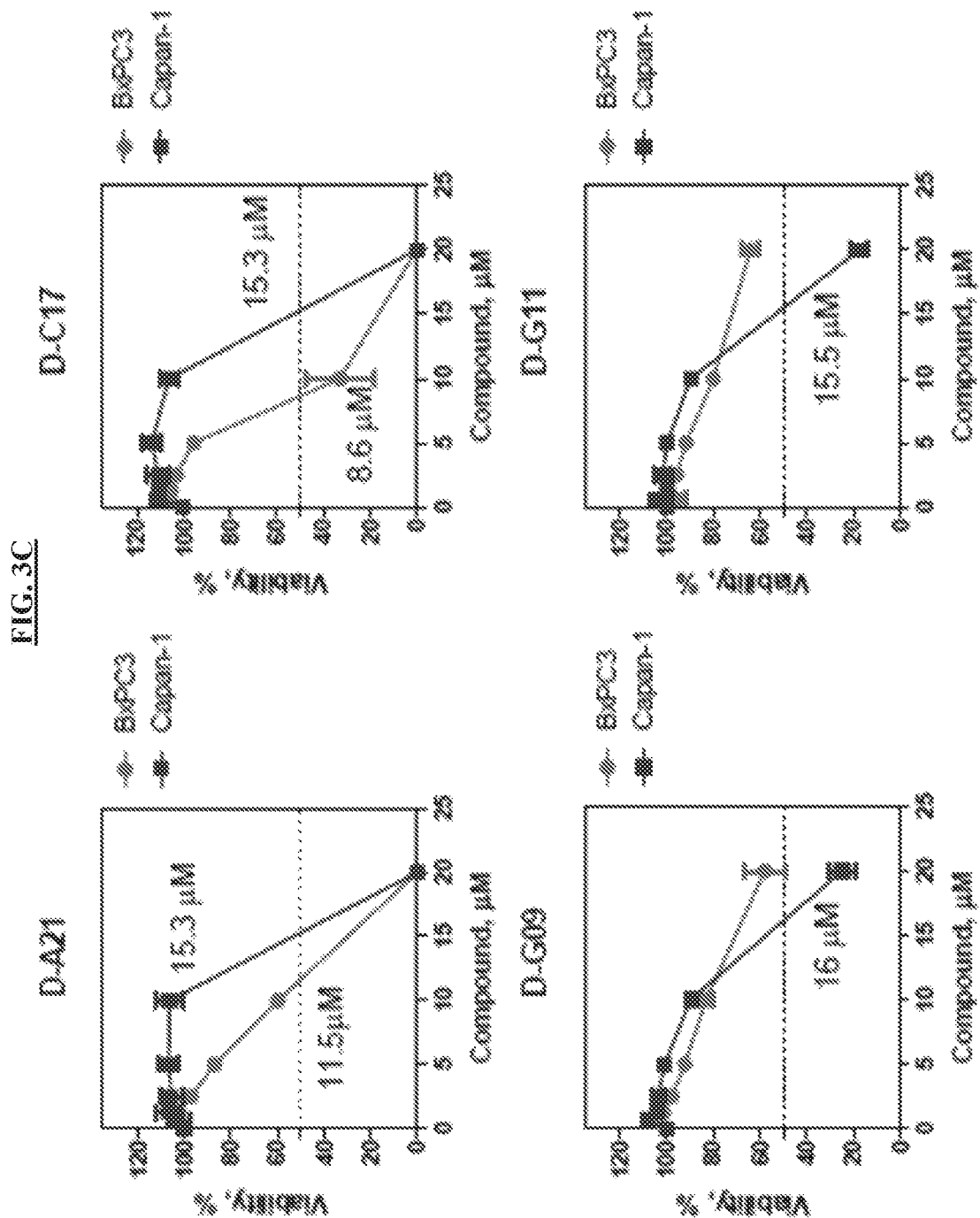
Figure 3D:
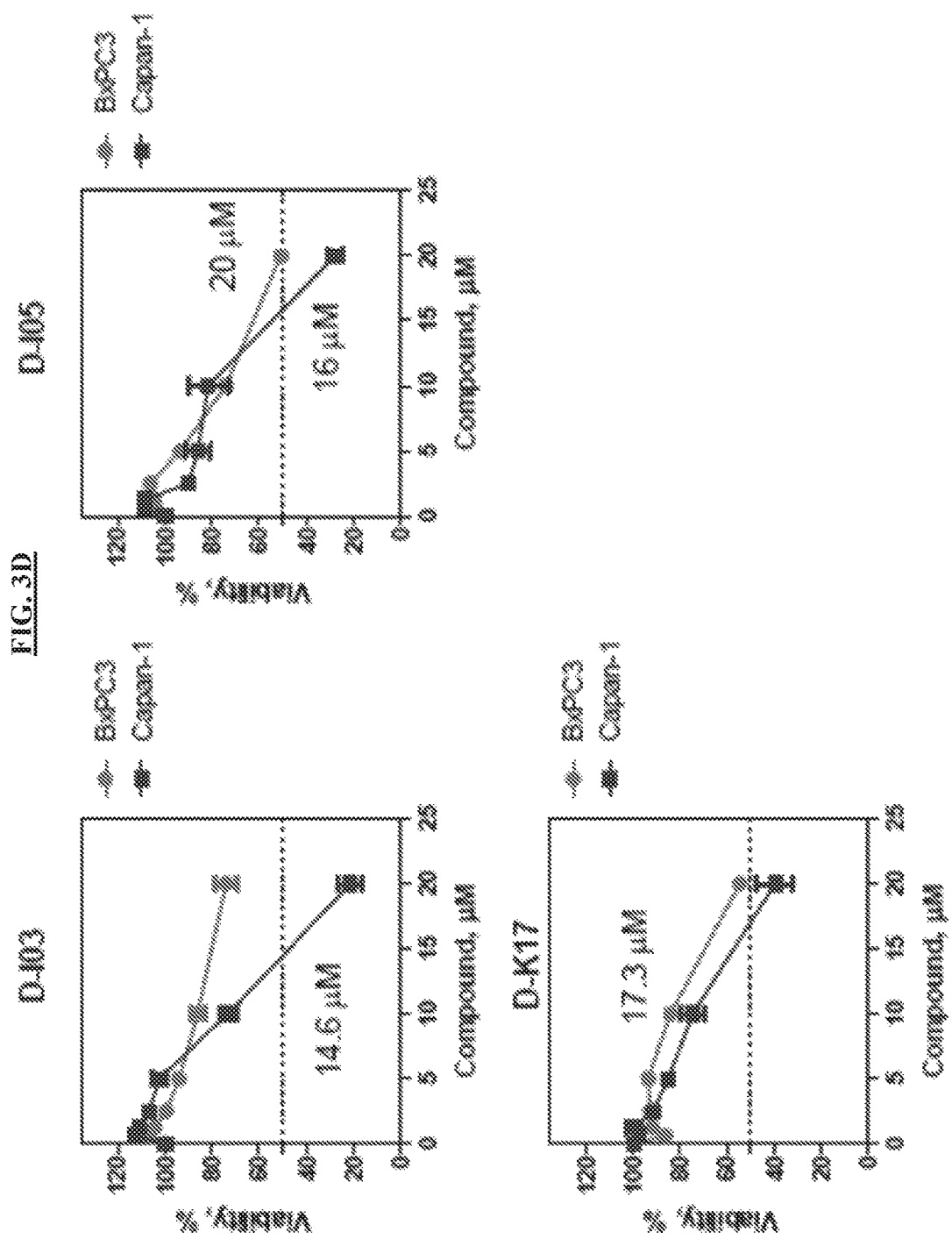
Figure 3E:
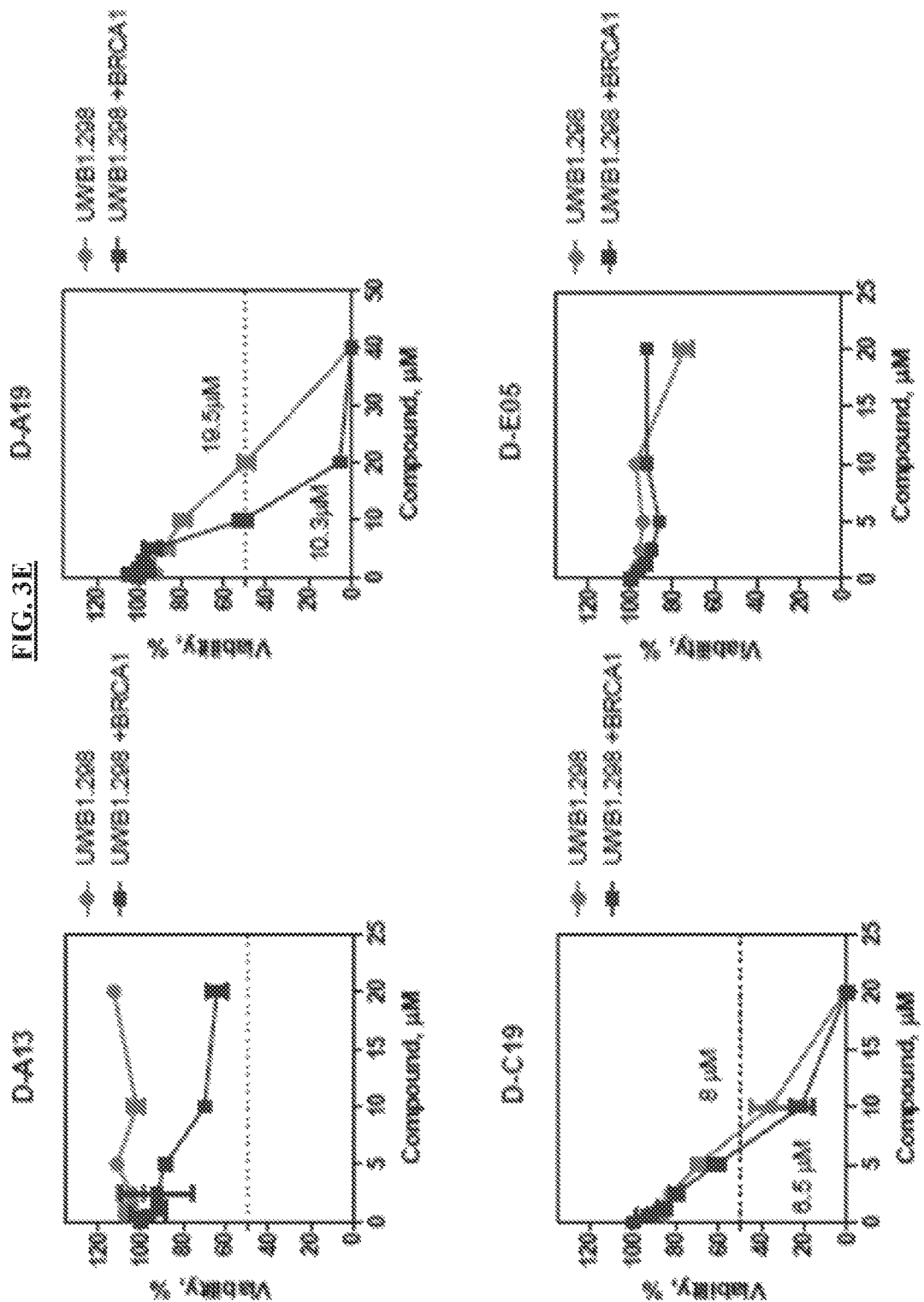
FIGS. 3E-3H illustrate the effects of the RAD52 inhibitors on survival of UWB1.289 (BRCA1$^-$) and [UWB1.289 (+BRCA1)] (BRCA1$^+$) cells. UWB1.289 is denoted by the line of dots; UWB1.289 (+BRCA1) is denoted by the line of squares. The experiments were repeated at least three times. Error bars indicate SD of the mean.
Figure 3F:
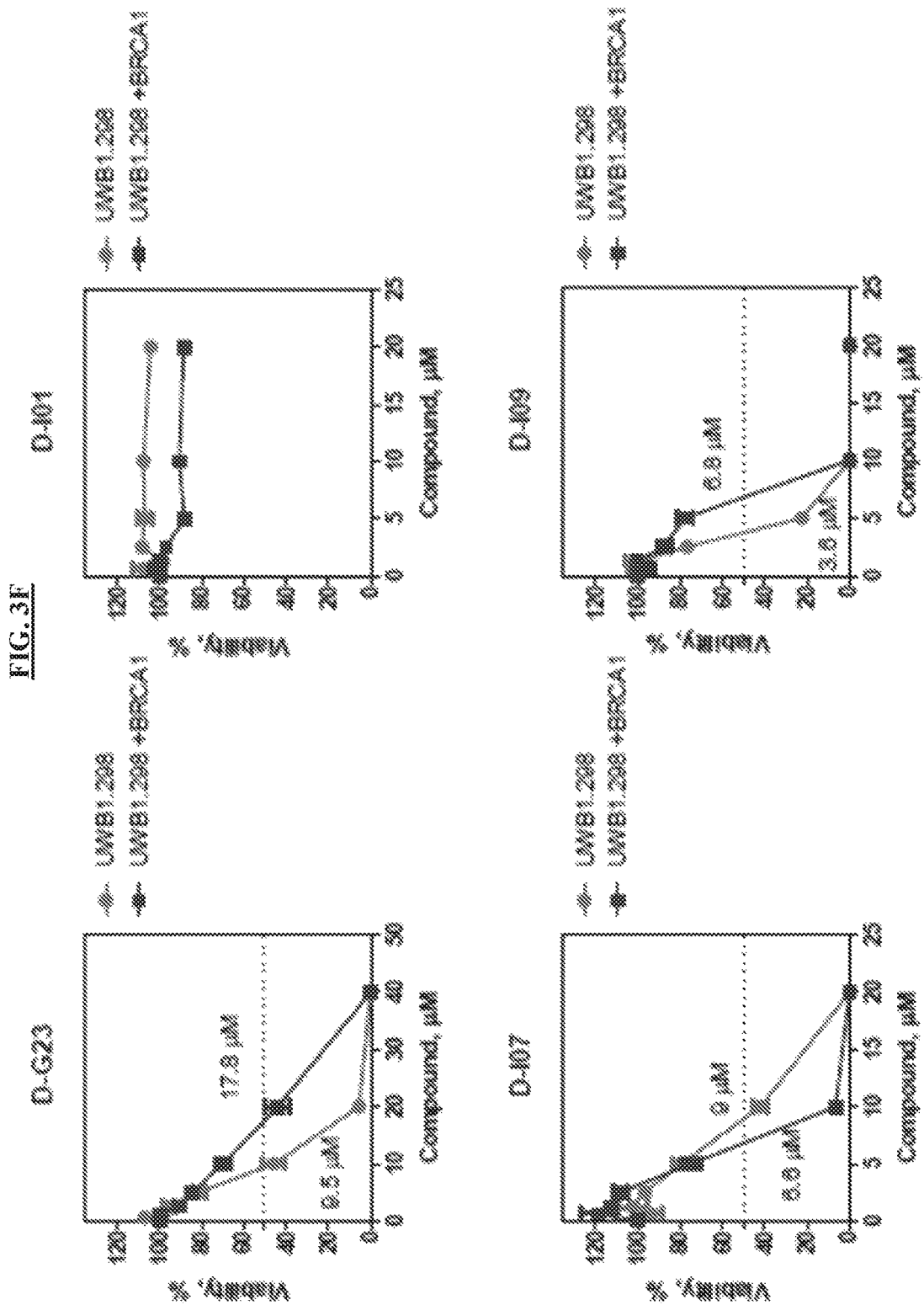
Figure 3G:
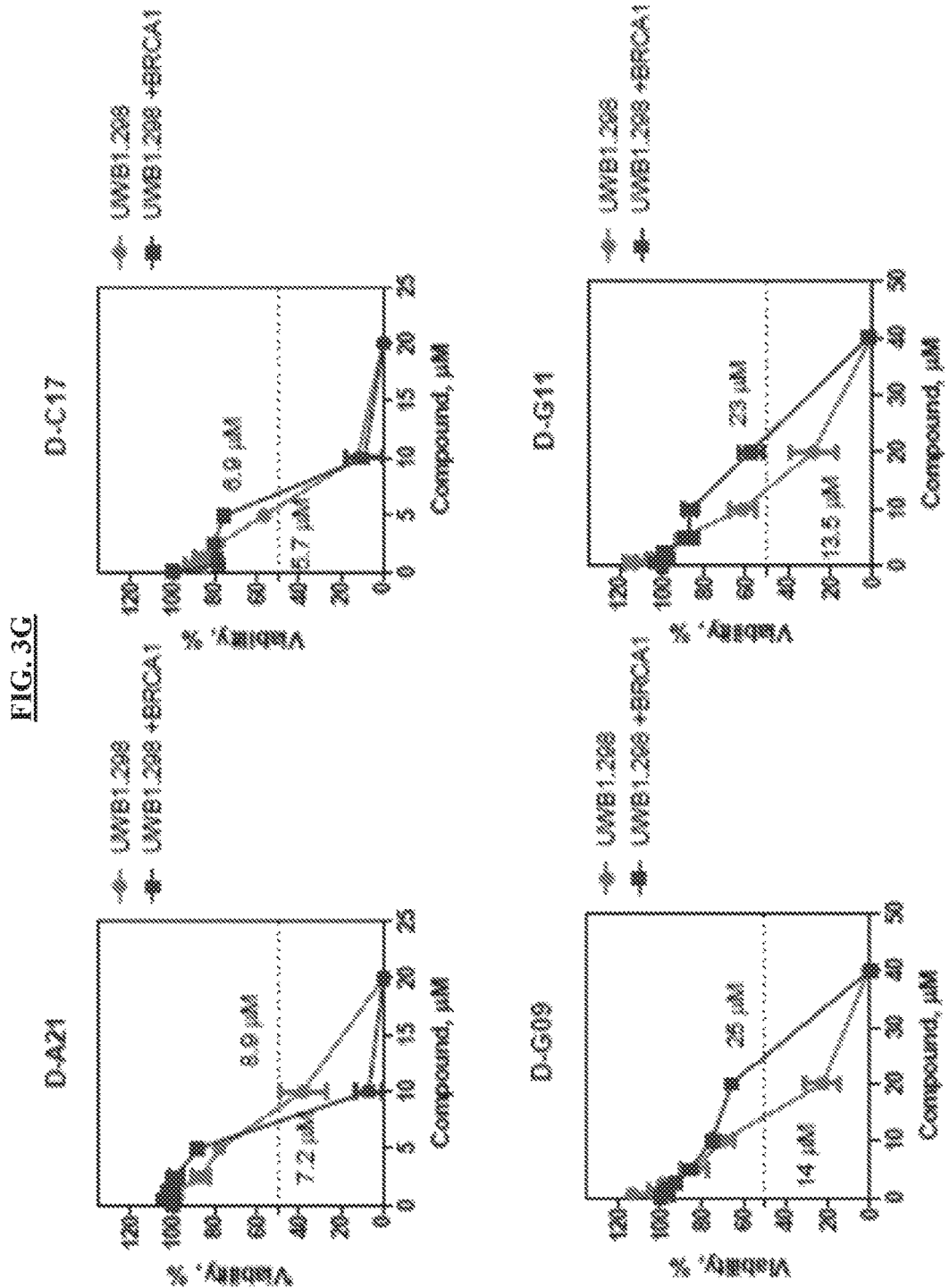
Figure 3H:
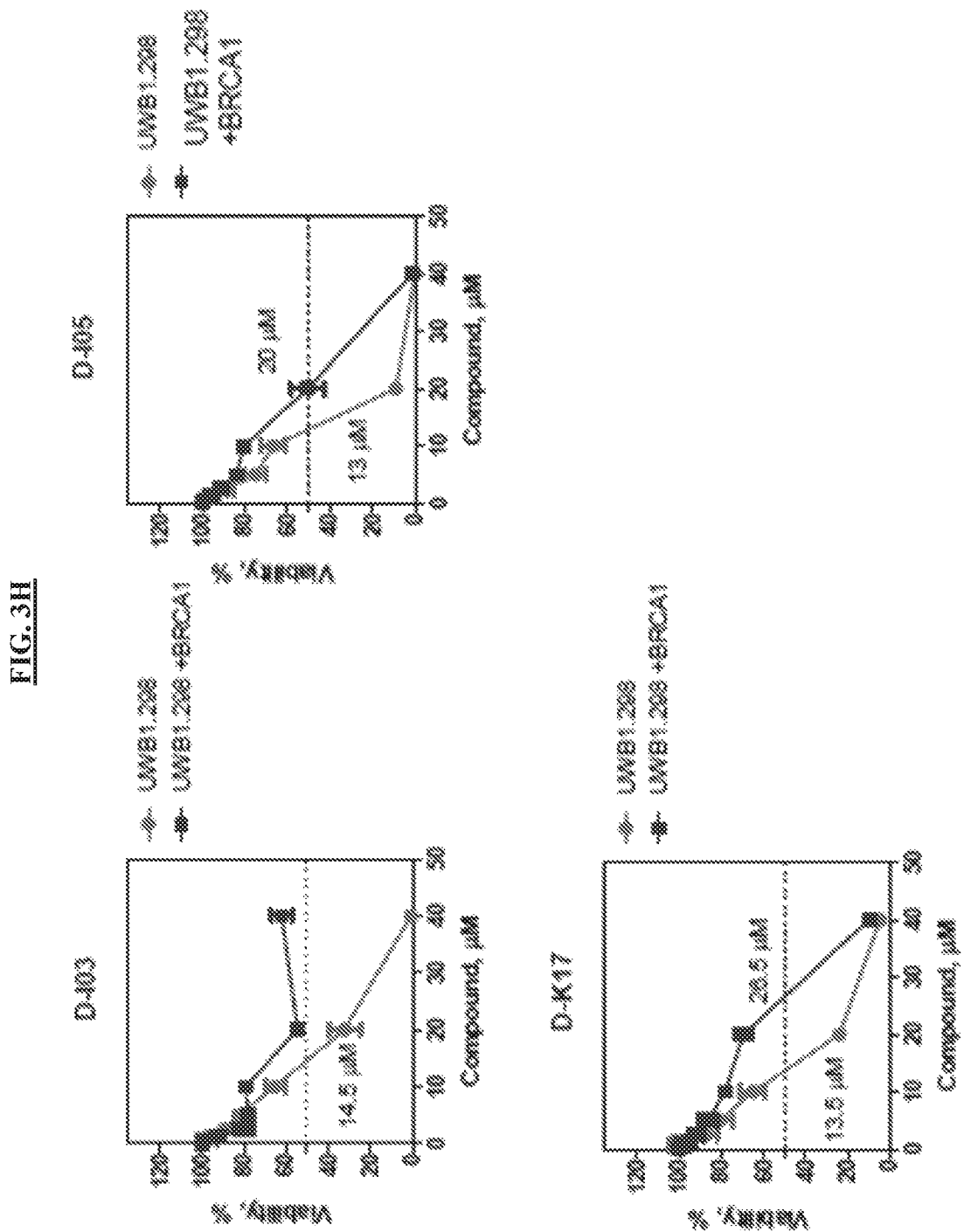

Then, the selectivity of the RAD52 inhibitors were examined using RAD51 as a non-specific target. RAD51 is structurally unrelated to RAD52, but shares DNA pairing activity with RAD52. Using the D-loop assay, at concentrations 10-fold higher than the $IC_{50}$ for RAD52 DNA pairing, only three out of 17 tested compounds showed non-specific inhibition of RAD51 greater than 2-fold relative to the DMSO control (FIG. 2D). Overall, as a result of the HTS and several confirmatory and selectivity assays, 14 specific inhibitors of ssDNA annealing and ssDNA pairing activity of RAD52 in vitro were identified.

Example 2: Analysis of RAD52 Inhibitors in Human BRCA1- and BRCA2-Deficient Cells The effects of 14 RAD52 inhibitors identified in the biochemical assays were tested on the growth of BRCA2-deficient Capan-1 cells and BRCA2-proficient BxPC3 cells. Five of the tested inhibitors preferentially suppressed the growth of Capan-1 cells (FIGS. 3A-3D).

Figure 4A:
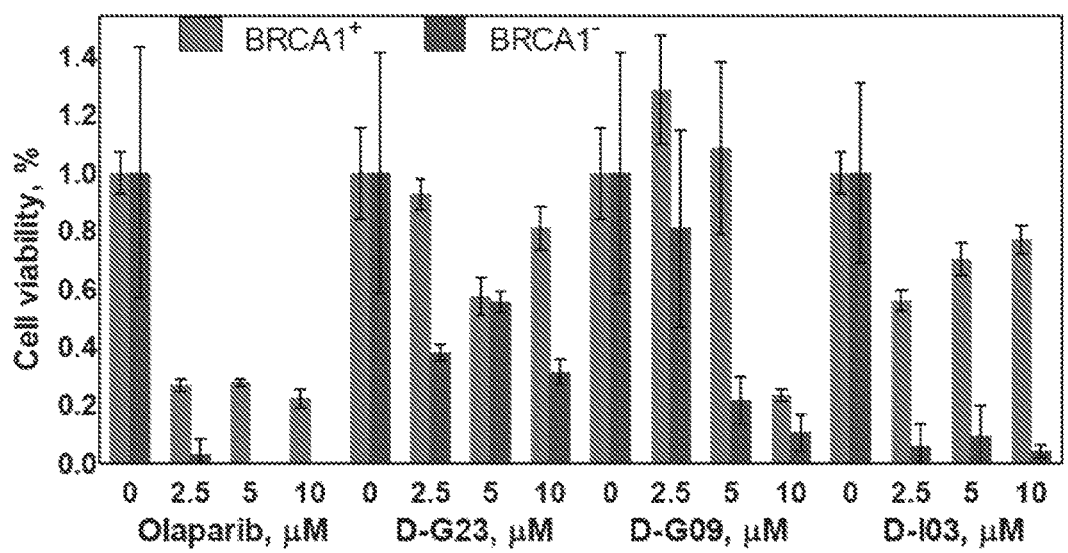
FIG. 4A illustrates the effects of RAD52 inhibitors on survival of MDA-MB-436 (BRCA1$^-$) and [MDA-MB-436 (BRCA1$^+$)] (BRCA1$^+$) cells. The experiments were repeated at least three times. Error bars indicate SD of the mean.
Figure 4B:
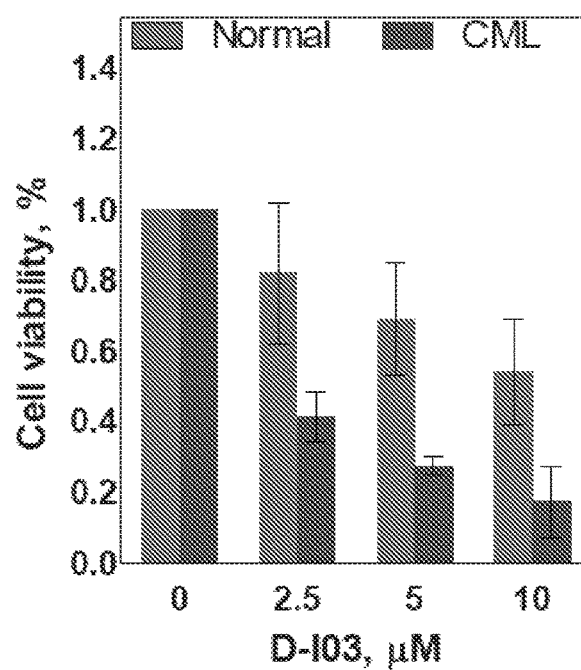
FIG. 4B illustrates the effects of RAD52 inhibitors on survival of BCR-ABL1-positive BRCA1-deficient CML cells and their BRCA1-proficient normal counterparts. The experiments were repeated at least three times. Error bars indicate SD of the mean.

Likewise, the effects of RAD52 inhibitors on the growth of BRCA1-deficient (UWB1.289 BRCA1) and BRCA1-proficient (UWB1.289 BRCA$^+$) cells were tested. 7 out 14 tested RAD52 inhibitors preferentially suppress the growth of BRCA1-deficient cells. Importantly, these 7 compounds included the 5 compounds that inhibited the growth of BRCA2-deficient cells (FIGS. 3E-3H). The effects of the 14 RAD52 inhibitors were tested on the survival of another BRCA1-deficient cells, and MDA-MB-436 cells. Three out 14 compounds, which also inhibited growth of UWB1.289 cells, showed an inhibitory effect on these cells compared with the isogenic MDA-MB-436 (BRCA1$^+$) cells (FIG. 4A). Finally, the effects of D-I03, the strongest inhibitor on BRCA1- and BRCA2-deficient cells, was tested on BCR-ABL1-positive BRCA1-deficient chronic myeloid leukemia (CML) patient cells (Podszywalow-Bartnicka et al., 2014, Cell Cycle 13, 3727-3741). BRCA1-deficiency in these cells is due to constitutive downregulation of this protein. D-I03 selectively diminished the growth potential of BRCA I-deficient CML patient cells in comparison to BRCA1-proficient normal counterparts (FIG. 4B).

Figure 4C:
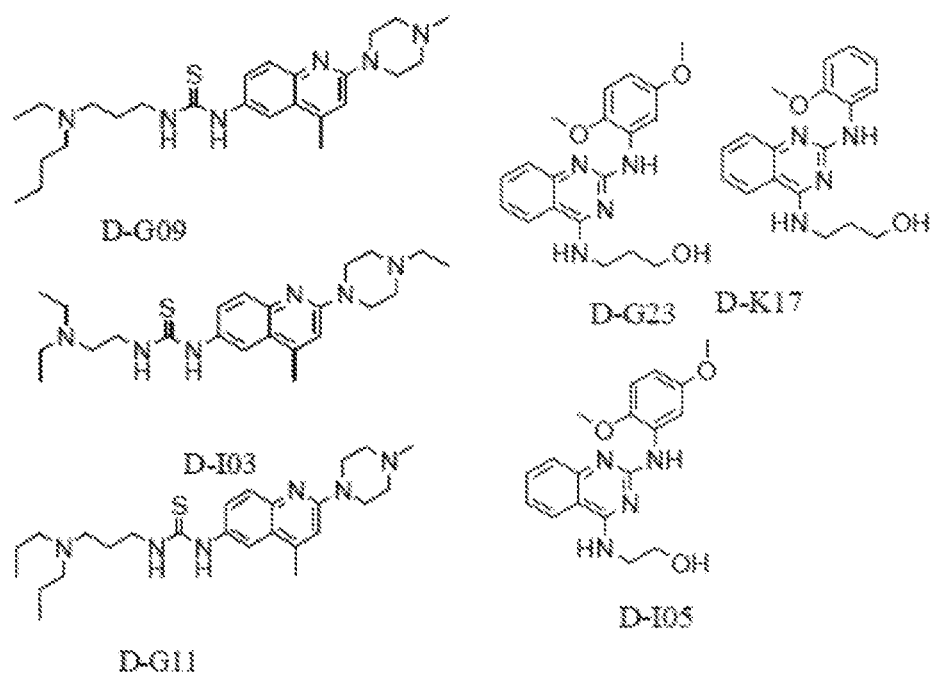
FIG. 4C illustrates the structures of the RAD52 inhibitors that preferentially inhibited growth of BRCA1- or BRCA2-deficient cells.

Overall, two compounds, D-G09 and D-I03, showed an inhibitory effect on all three tested BRCA1- and BRCA2-deficient cell lines. Importantly, these compounds showed significant structural similarity sharing the quinoline core (FIG. 4C). Another member of this structural group, D-GI 1, showed activity on two of the tested cell lines (UWB1.289 and Capan-1). Remarkably, three other compounds, D-G23, D-I05, and D-K17, that preferentially inhibited at least two BRCA1/2-deficient cell lines also share similarity, but belonging to another structural type with the quinazoline core. From all tested compounds, D-I03 showed the strongest and most consistent inhibitory effect on all tested BRCA1$^{-/-}$ and BRCA2$^{-/-}$ cell lines, moreover, it selectively inhibited growth of BRCA1-deficient CML cells from patients. Further. D-I03 and D-G23 have calculated properties within ranges generally considered "drug-like" by the research community and favorable for important parameters such as oral bioavailability (Table 3).

Example 3: Measurement of Inhibitors Binding to RAD52 by SPR

Figure 5A:
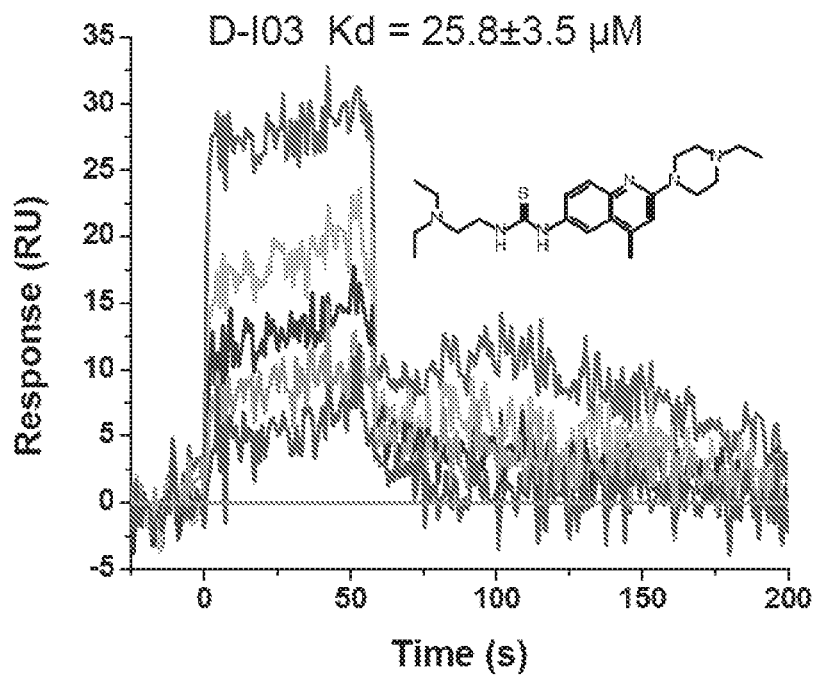
FIG. 5A illustrates the measurement of D-I03 binding to RAD52 at concentrations of (bottom to top) 3.125, 6.25, 12.5, 25, and 50 µM. Colored lines indicate experimental data.
Figure 5B:
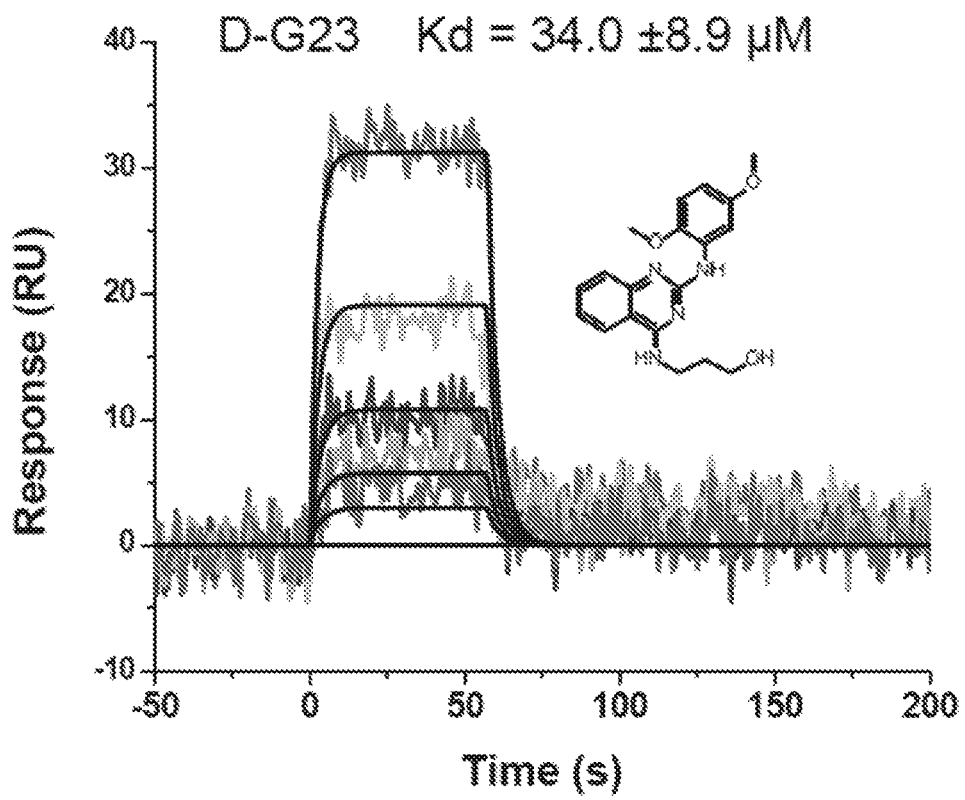
FIG. 5B illustrates the measurement of D-G23 binding to RAD52 at concentrations of (bottom to top) 1.56, 3.125, 6.25, 12.5, and 25. Colored lines indicate experimental data, whereas black lines indicate fitting to the simple 1:1 binding model using the ProteOn Manager Software version 3.0 (Bio-Rad). Kinetic values are as follows: $k_a$=1.15 (±0.44)× 104 M−1 s−1; $k_d$=3.62 (±0.7)×10−1 s−1; $K_d$=34.0±8.9 µM.
Figure 5C:
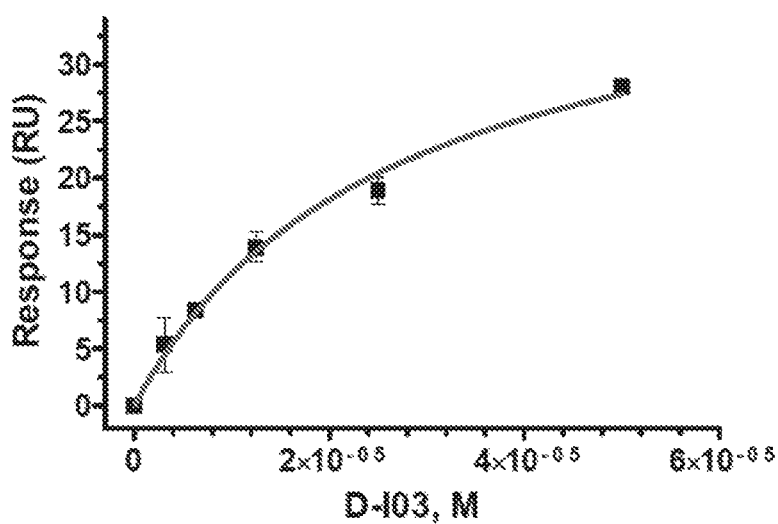
FIG. 5C is a graph illustrating the method of determining $K_d$ of D-I03 binding to RAD52 by plotting the response at equilibrium (Req) versus concentration of D-I03. Experiments were repeated at least three times; errors of mean indicated by SD.

RAD52 inhibitors were tested to show activity in the biochemical and cell-based assays physically interact with RAD52. D-I03 (3.12-50 µM) and D-G23 (3.12-25 µM) have been demonstrated to bind directly to RAD52 (FIG. 5) using the surface plasmon resonance (SPR) method. The anti-HIV mAb 2F5 structurally unrelated to RAD52 was used in control and non-specific binding signal was subtracted from the RAD52 binding signal.

The $K_d$ values for D-I03 and D-G23 are 26.1±4.5 µM and 34.0±8.9 µM, respectively. These values are somewhat higher than one might expect from the $IC_{50}$ values in the biochemical and cell-based assays with these inhibitors. Without wishing to be limited by any theory, because the active form of RAD52 is a hexamer, the apparent differences in the activities of inhibitors may suggest that inhibition of RAD52 requires only partial saturation of the RAD52 hexamer with inhibitors. D-I03 and D-G23 did not bind DNA using the acridine orange displacement assay. Thus, these compounds inhibit DNA annealing and pairing activities of RAD52 through direct binding, not through interaction with DNA substrates.

Figure 6A:
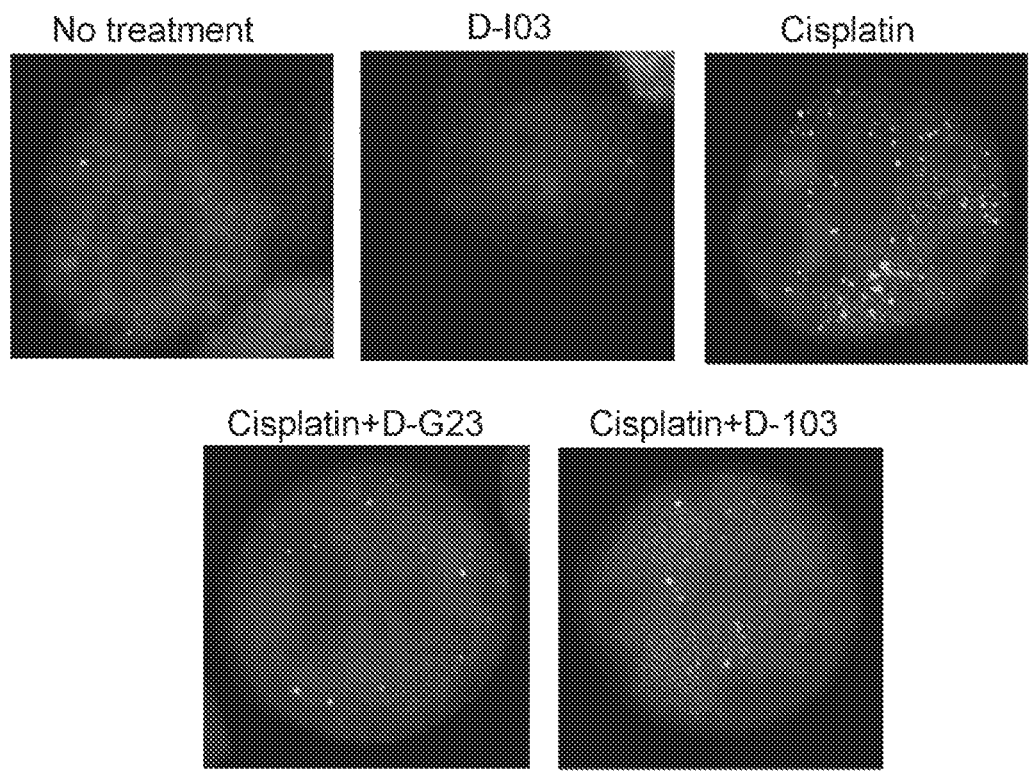
FIG. 6A illustrates the effects of D-G23 and D-I03 (2.5 µM) on GFP-RAD52 foci formation in response to cisplatin (10 µM) treatment. GFP-RAD52 was constitutively expressed in p210BCR-ABL1-positive 32Dcl3 murine hematopoietic cells (BRCA1-deficient).
Figure 6B:
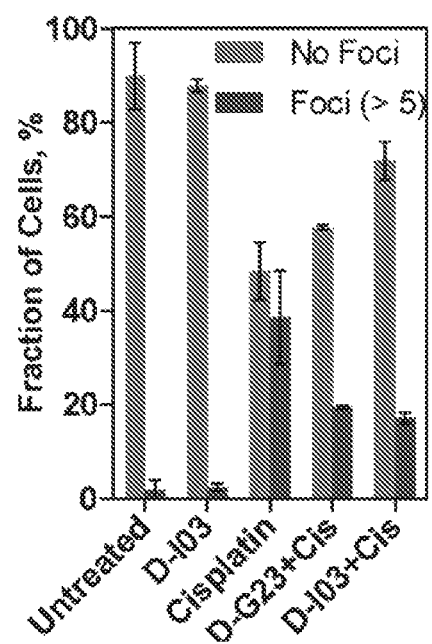
FIG. 6B is a graphical presentation of the data from FIG. 6A.

Example 4: Inhibitors Disrupt the RAD52, but not RAD51, Foci Formation in BRCA1-Deficient Cells D-I03 and D-G23 were tested to determine whether they inhibit RAD52 activities in the cell. In response to DNA damage, RAD52 accumulates in the nucleus forming distinct structures known as foci (Essers et al., 2002. EMBO J. 21, 2030-2037; Liu et al., 2000. EMBO Rep 1, 85-90). The foci represent RAD52 complexes with DNA repair intermediates. Inhibitors of RAD52 may decrease RAD52 foci formation by disrupting its interaction with DNA substrates. Indeed, both D-I03 and D-G23 inhibited RAD52 foci formation induced by cisplatin in BCR-ABL1-positive BRCA1-deficient 32Dcl3 murine hematopoietic cell line that expresses GFP-RAD52 (Cramer-Morales et al., 2013, Blood 122, 1293-1304) (FIG. 6A). In the presence of D-I03 (2.5 μM) and D-G23 (2.5 μM), the fraction of cells with RAD52 foci (25 foci) was decreased approximately 2.0-2.5-fold, from 38.7±10% to 17±1% and 19±0.4%, respectively; at the same time, the fraction of cisplatin-treated cells without foci was increased from 48.4±6.2% to 71.9±4.1% and 57.6±0.5% (FIG. 6B). Thus, compounds of two chemotypes, represented by D-I03 and G-23, inhibited the biochemical activities of RAD52 in vitro, showed preference in suppressing survival of BRCA1- and BRCA2-deficient cells and inhibited formation of damage-induced RAD52 foci formation.

Figure 6C:
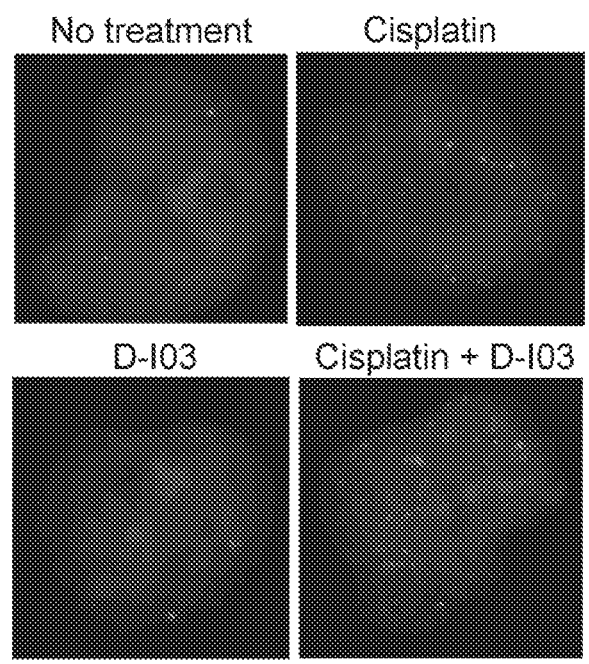
FIG. 6C illustrates the effect of D-I03 (2.5 M) on RAD51 foc formation with and without cisplatin (10 µM) treatment in parental 32Dcl3 cells (BRCA I-proficient).
Figure 6D:
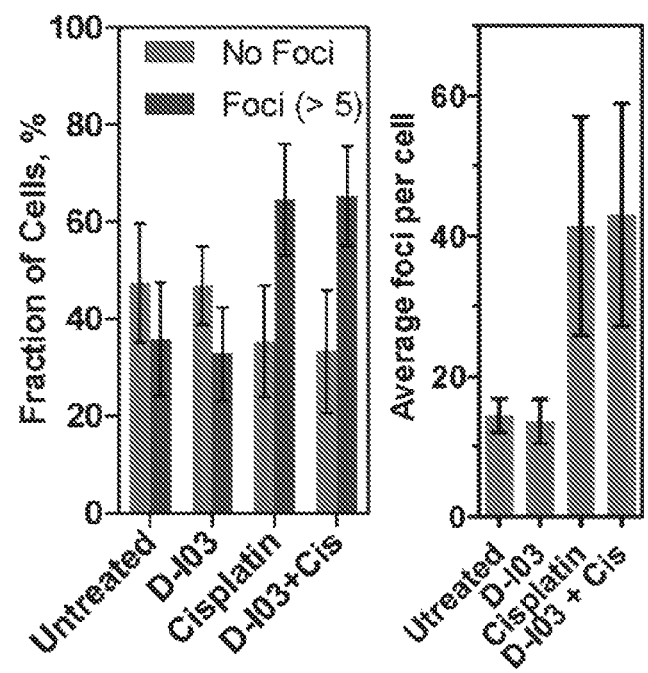
FIG. 6D is a graphical presentation of the data from FIG. 6C.

The non-specific effect of D-I03, the strongest of the RAD52 inhibitors, on RAD51 foci formation was also tested. Using parental 32Dcl3 (BRCA1-proficient) cells, D-I03 was found not to have a significant effect on RAD51 foci induced by cisplatin (FIG. 6C). This result supports the specificity of this compound towards the target RAD52, because it inhibits RAD52-dependent foci formation induced by cisplatin (as described elsewhere herein).

In addition, D-I03 alone induced neither RAD51 foci nor RAD52 foci (in BRCA1-deficient cells; FIG. 6A) indicating low genotoxicity of this compound.

Example 5: D-I03 Inhibition of Single-Strand DNA Annealing and Lack of Inhibition of Gene Conversion in U2OS Cells In both yeast and mammalian cells, RAD52 promotes single-strand DNA annealing (SSA). SSA is a type of HR that is initated at DSBs and mediated by annealing of fortuitous direct repeats flanking DSB ends after exonucleolitic resection. This mechanism leads to end rejoining with concomitant deletion of sequences between direct repeats.

Figure 7A:
Figure 7A:
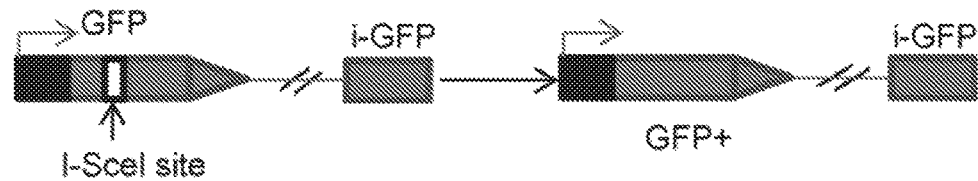
Figure 7A:
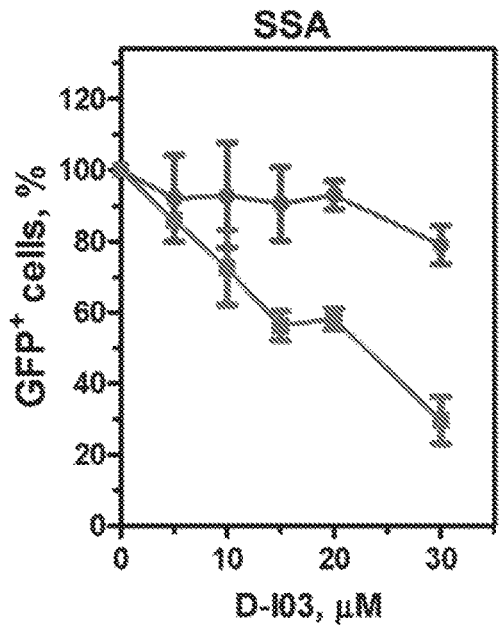
Figure 7A:
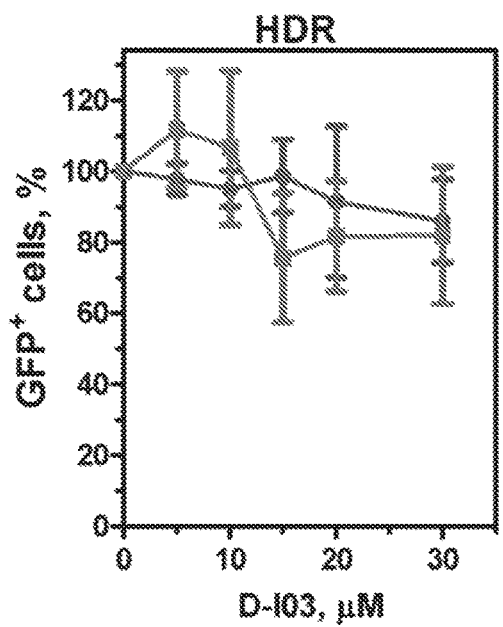

Using SA-GFP construct integrated chromosomal DNA, the effect of RAD52 inhibitor D-I03 on SSA in U2OS cells was examined. The SA-GFP reporter system contains a 5'-fragment of the GFP (5'-GFP) gene, and a 3'-fragment of the GFP (3'-GFP) that contains an 18-bp I-SceI site (FIG. 7A). The GFP fragments are separated by 2.7 kb region and share a 266 bp region of homology. Transfection of cells with I-SceI expressing vector pCBASce induces DSB in the 3'-GFP. Repair of the DSB by SSA leads to formation of GFP+ cells. Thus, each SSA event can be scored by the appearance of a green fluorescent cell.

Figure 8A:
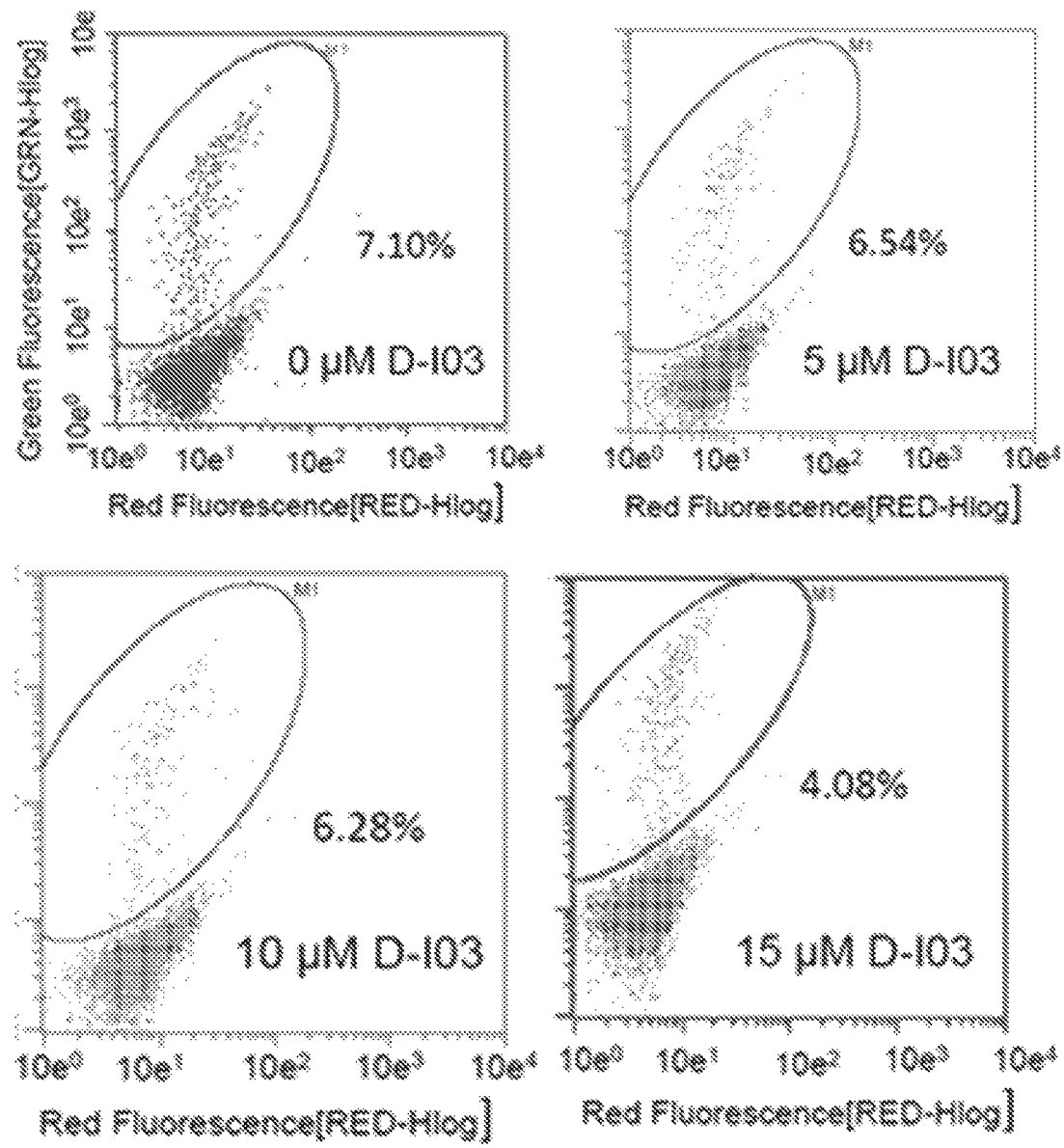
FIGS. 8A-8D are a set of graphs illustrating the effect of E-103 on the repair of the I-SceI-induced DSBs in U2OS cells carrying the SSA-GFP (FIGS. 8A-8B) or HDR-GFP (FIGS. 8C-8D) reporter, as measured by flow cytometry. Green fluorescence is ploted against red fluorescence for each sample of 10.000 cells. The GFP+ population of cells is denoted by the elliptical M1 marker.
Figure 8B:
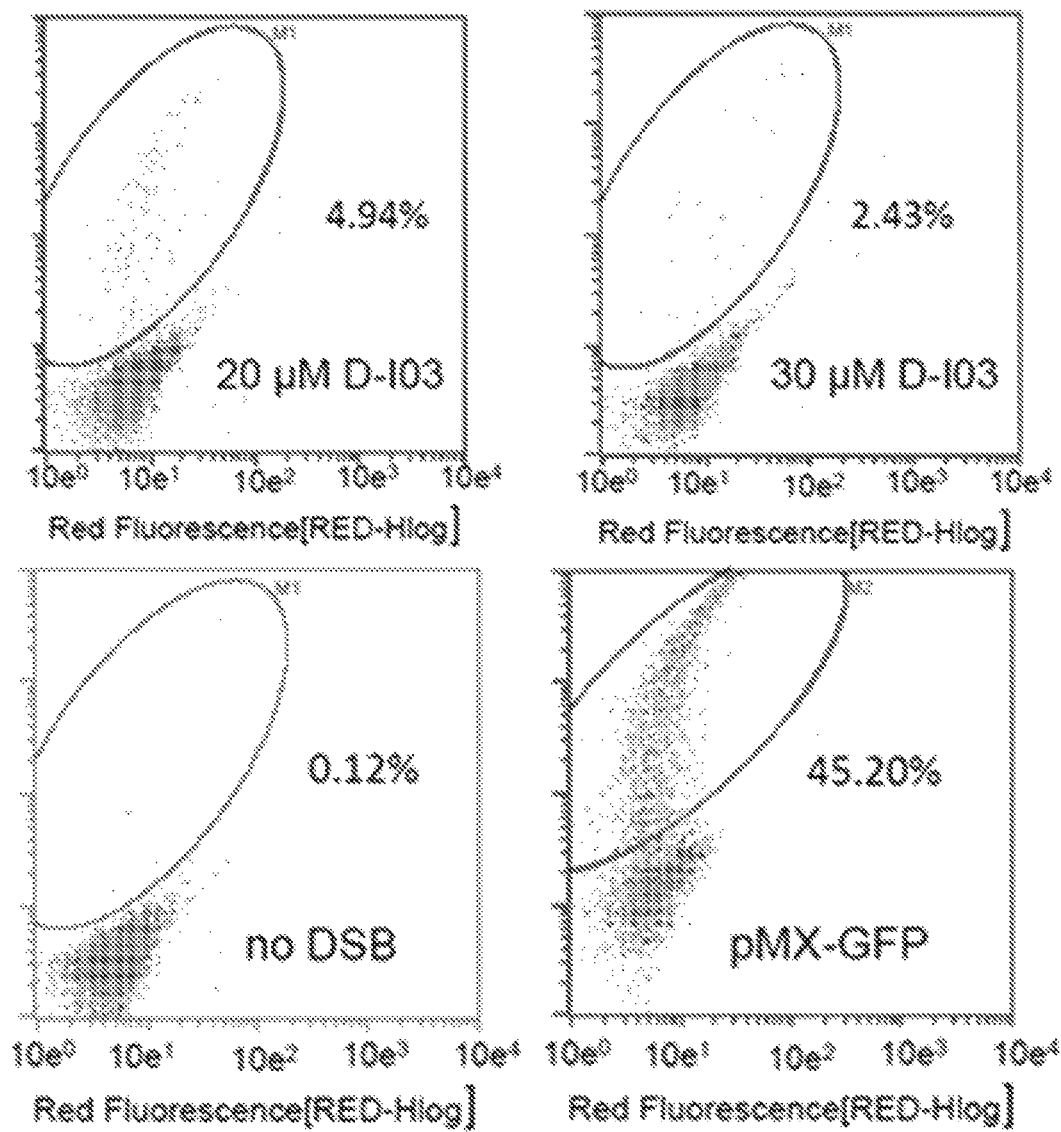

D-I03 reduces formation of GFP+ cells in a concentration dependent manner, at 30 μM D-I03 the yield of GFP+ cells was reduced about 3.4-fold (FIG. 7B, red line; FIGS. 8A-8B). In control, the effect of D-I03 on formation of GFP+ cells when U2OS cells were transfected was measured with pMX-GFP plasmid encoding GFP (FIG. 7B, green line). Up to 30 μM, D-I03 had no significant effect on the recovery of GFP+ cells.

Figure 8C:
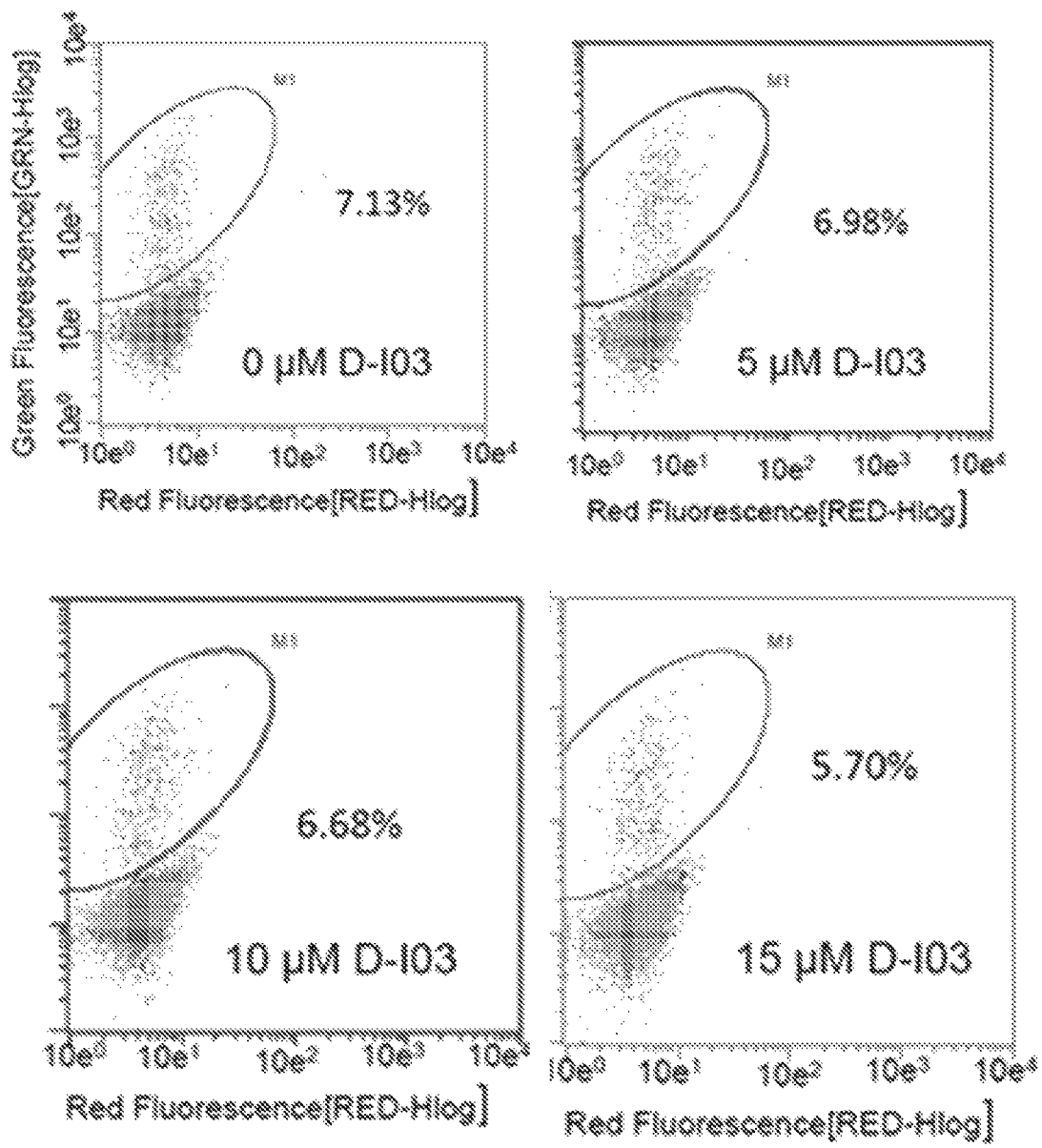
Figure 8D:
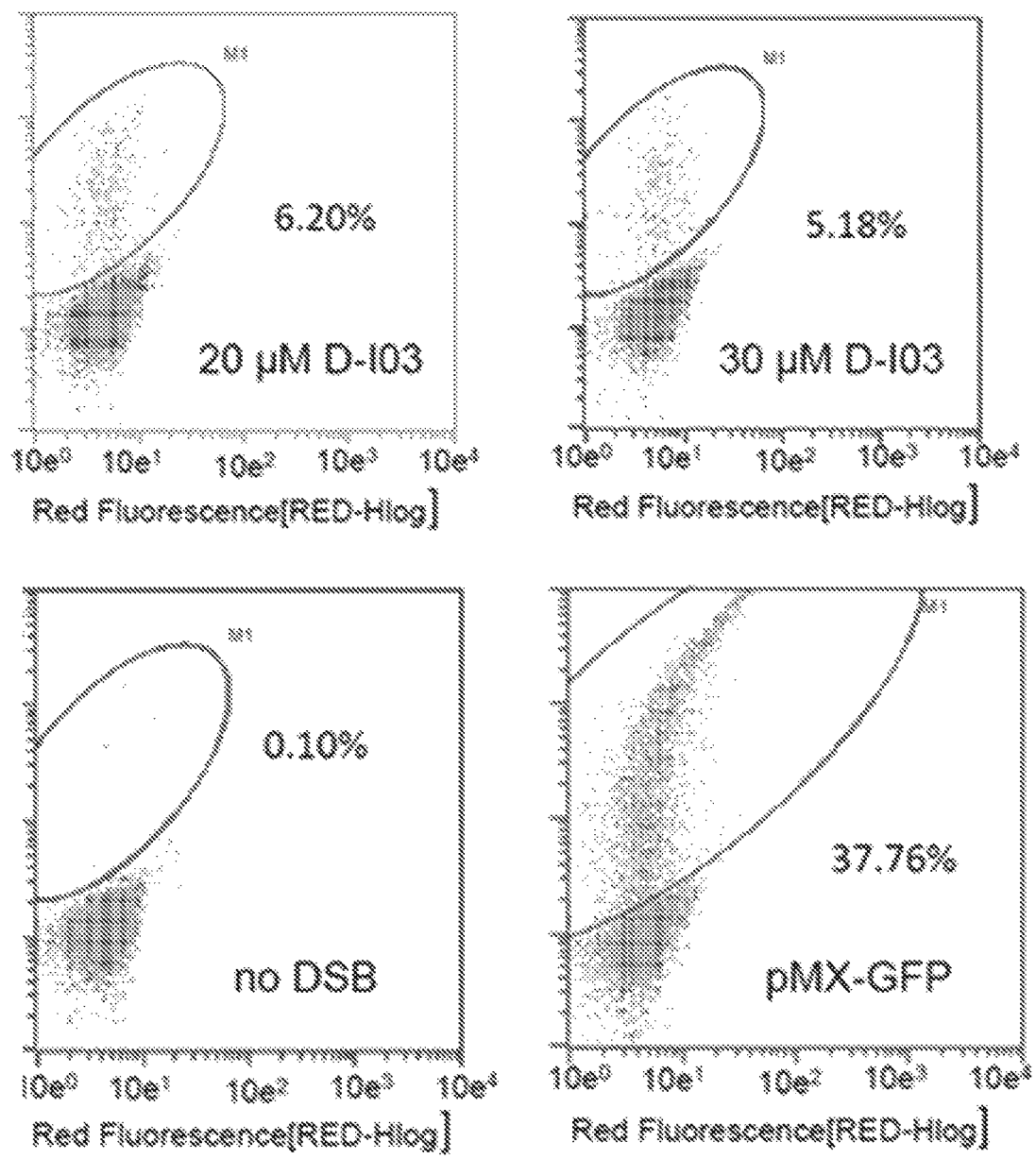
Figure 9:
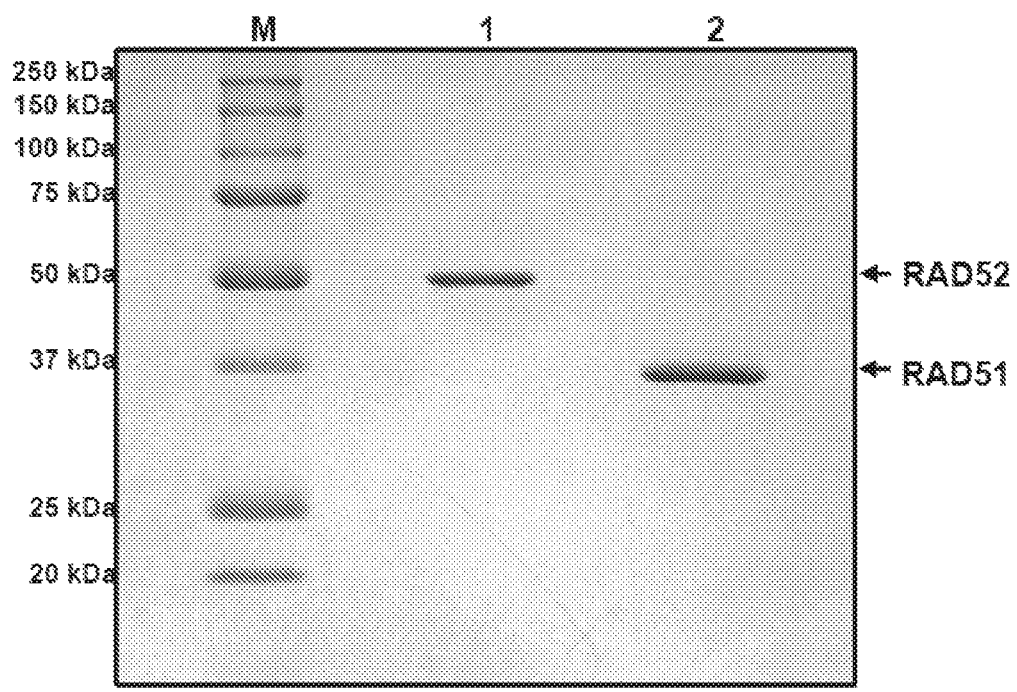
FIG. 9 is an image illustrating analysis of RAD51 and RAD52 proteins in a SDS-polyacrylamide gel. Proteins were stained with Coomassie blue. Lane M, Migration markers; Lane 1. Rad52; Lane 2, RAD51. 1 µg of each protein was loaded on a 12% SDS-polyacrylamide gel.
Figure 10:
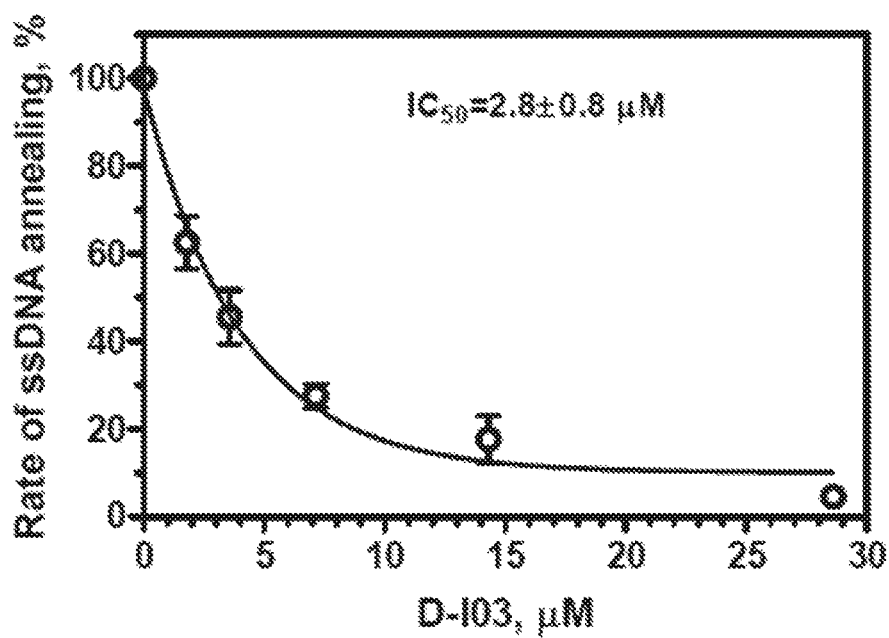
FIG. 10 is a graph illustrating the effect of D-I03 concentration on the initial rate of ssDNA annealing promoted by RAD52. The rates of RAD52-promoted ssDNA annealing were calculated based on the data in FIG. 1C. The data were the mean of 3 independent measurements; error bars represent the SD.

The effect of D-I03 on DSB repair was tested via the canonical homology dependent recombination (HDR; also known as gene conversion) mechanism using the chromosomally integrated DR-GFP construct in U2OS cells. RAD52 has no significant effect on the HDR in mammalian cells (Stark, et al., 2004, Mol. Cell. Biol. 24:9305-9316). The DR-GFP construct consists of two inactive compies of the GFP gene, one that is disabled by insertion of I-SceI recognition site and another (iGFP) is truncated at both ends (FIG. 7A). A unique DSB is generated in this construct after the cells are transfected with pCBASce plasmid. The repair of this DSB by gene conversion using iGFP as a template gives rise to the functional GFP gene. D-I03 does not have a significant effect on formation of GFP-positive cells (FIG. 7C, red line; FIG. 8C-8D). D-I03 also has no effect on GFP expression or on recovery of GFP-positive cells when U2OS cells were transfected with pMX-GFP plasmid encoding GFP (FIG. 7C, green line). Taken together, these results indicate that, consistent with inhibition of RAD52 in human cells, D-I03 reduces the level of DSB-induced SSA, but not HDR (which does not depend on RAD52).

Taken together, the results presented herein demonstrate that D-I03 inhibits RAD52 specifically in human cells.

Example 6: Synthesis of Exemplary Compounds of Formula (II)

Scheme 1: Synthesis of exemplary compounds of Formula (II)

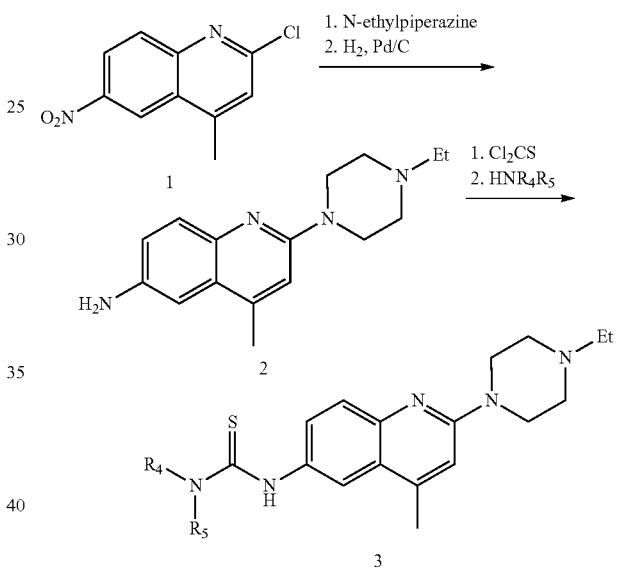

Briefly, as illustrated in Scheme 1, commercially available 2-chloro-4-methyl-6-nitroquinoline (1) is reacted in a SNAr reaction with N-ethylpiperazine, and the resultant intermediate is reduced to afford amine intermediate (2). Amine (2) can be reacted with thiophosgene to afford the corresponding isothiocyanate, which can be reacted with various amines to generate thiourea (3).

Example 7: Synthesis of Exemplary Compounds of Formula (III)

Scheme 2: Synthesis of exemplary compounds of Formula (III)

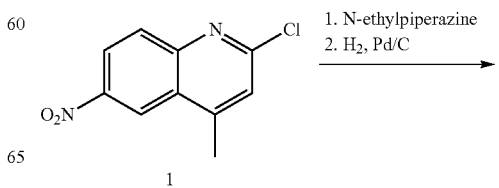

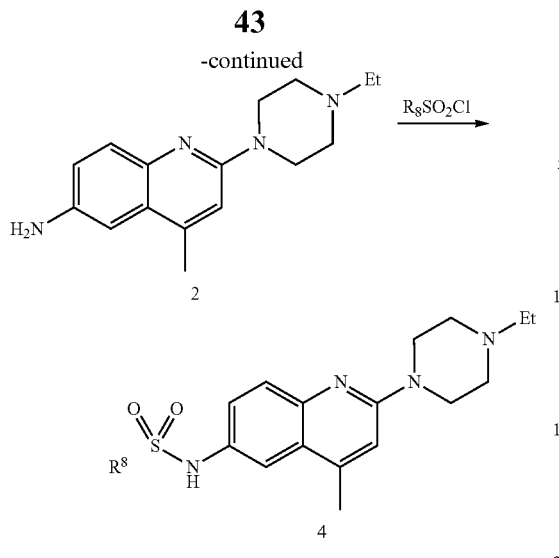

Briefly, as illustrated in Scheme 2, commercially available 2-chloro-4-methyl-6-nitroquinoline (1) is reacted in a SNAr reaction with N-ethylpiperazine, and the resultant intermediate is reduced to afford amine intermediate (2). Amine (2) can be reacted with sulfonyl chloride to afford the corresponding sulfonamide (4).

Example 8: Synthesis of Exemplary Compounds of Formula (IV)

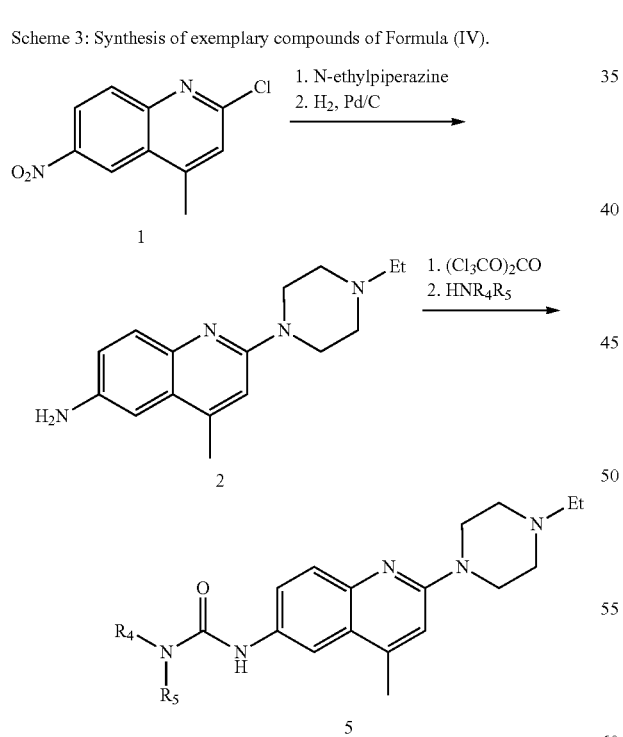

Briefly, as illustrated in Scheme 3, commercially available 2-chloro-4-methyl-6-nitroquinoline (1) is reacted in a SNAr reaction with N-ethylpiperazine, and the resultant intermediate is reduced to afford amine intermediate (2). Amine (2) can be reacted with triphosgene, followed by various amine to afford the corresponding urea (5).

Example 9: Synthesis of Exemplary Compounds of Formula (V)

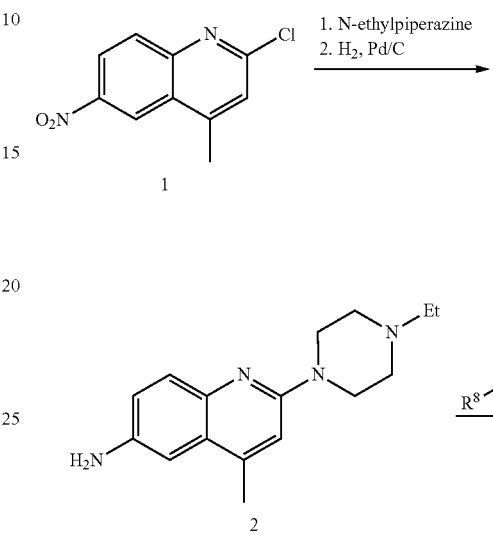

Briefly, as illustrated in Scheme 4, commercially available 2-chloro-4-methyl-6-nitroquinoline (1) is reacted in a SNAr reaction with N-ethylpiperazine, and the resultant intermediate is reduced to afford amine intermediate (2). Amine (2) can be reacted with acid chloride to afford the corresponding amide (6).

Example 10: Synthesis of Exemplary Compounds of Formula (VI)

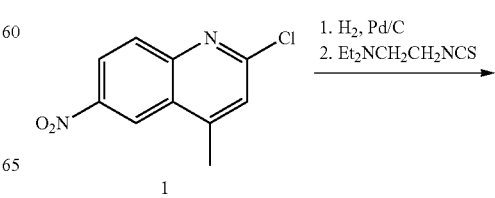

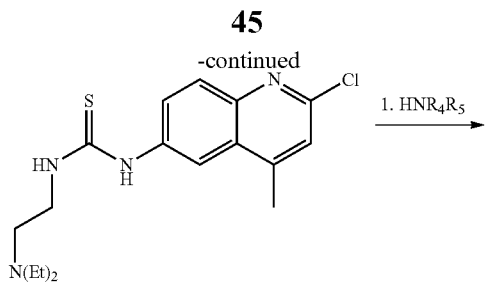

Briefly, as illustrated in Scheme 5, commercially available 2-chloro-4-methyl-6-nitroquinoline (1) is reduced to afford the corresponding amine, using hydrogenation or any alternative reduction method. The amine intermediate can be reacted with commercially available N,N-diethyl-2-isothiocyanatoethan-1-amine to afford the key thiourea intermediate (7). Intermediate 7 is reacted with various amines to afford the compound (8).

Example 11: Synthesis of Exemplary Compounds of Formula (VII)

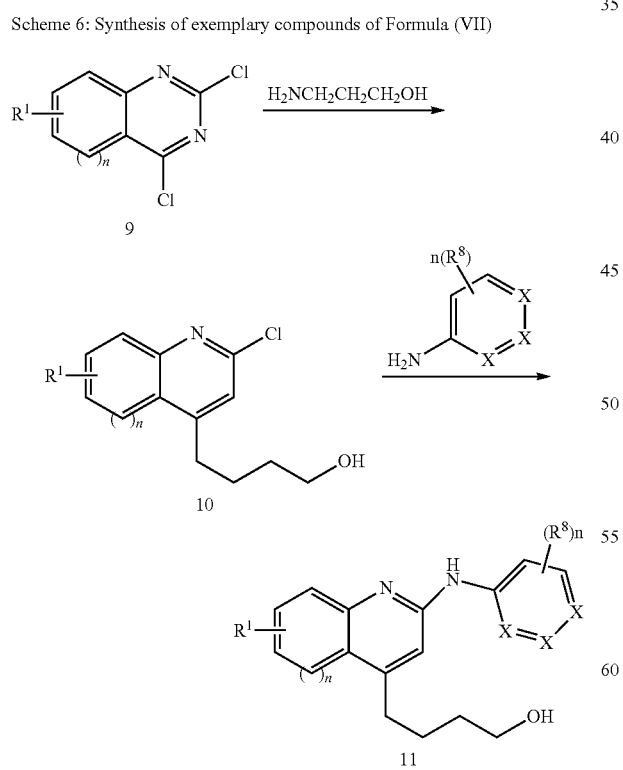

Briefly, as illustrated in Scheme 6, substituted dichloroquinazolines or isosteres (9) (e.g., substituted pyrimidines, thienopyrimidines, pyridopyrimidines, etc) are reacted with 3-aminopropan-1-ol to afford intermediate (10). Intermediate (10) undergoes catalytic coupling reaction to afford the compound (11).

Example 12: Synthesis of Exemplary Compounds of Formula (VIII)

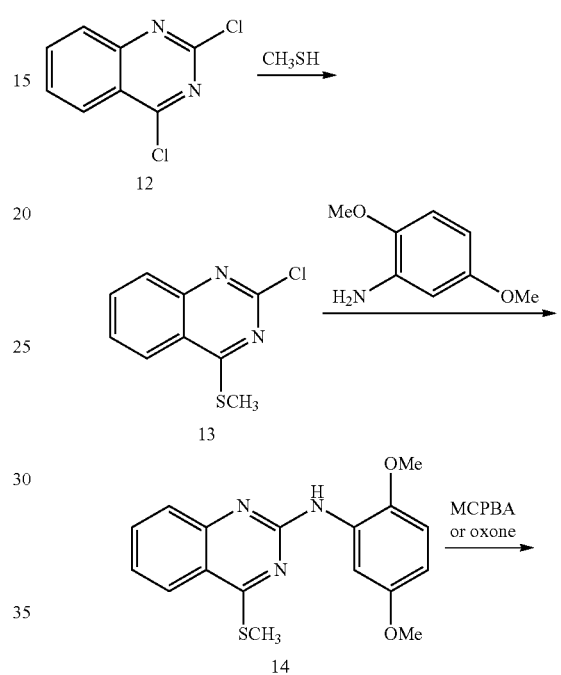

Briefly, as illustrated in Scheme 7, commercially available 2,4-dichloroquinazoline (12) is reacted with methanethiol to yield intermediate (13). Intermediate 13 is reacted with 2,5-dimethoxyaniline to generate intermediate (14). Oxidation of the intermediate (14) affords sulfone (15). Sulfone (15) is reacted with various amines to generate the compound (16).

Example 13: Synthesis of Exemplary Compounds of Formula (VIII)

Scheme 8: Synthesis of exemplary compounds of Formula (IX)

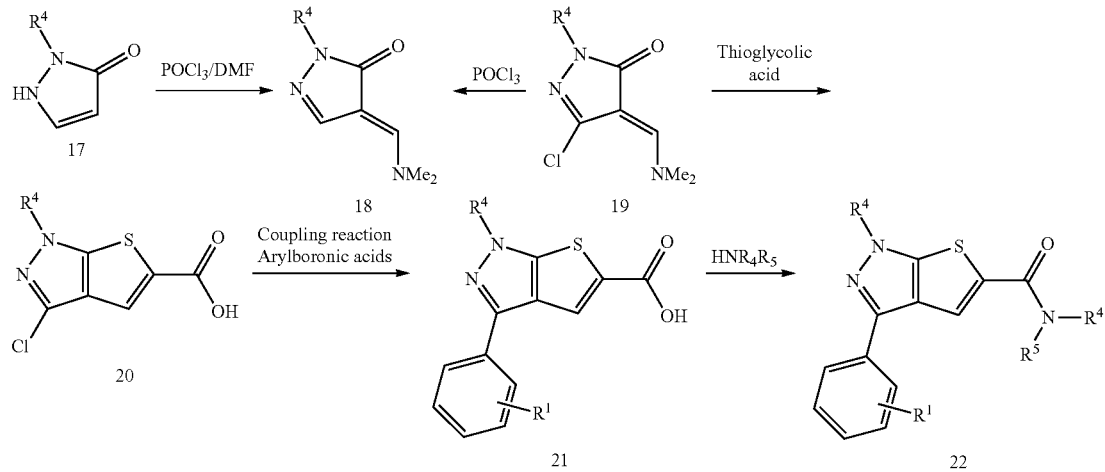

Briefly, as illustrated in Scheme 8, pyrazolinone (17) is reacted with $POCl_3/DMF$, followed by $POCl_3$ to afford intermediate (19) (Koshelev, et al., 1972, Organicheskoi Khimii, 8:1750-1754). Intermediate (19) is reacted with thioglycolic acid to yield pyrazolothiophene (20). Catalytic coupling reaction of pyrazolothiophene (20) affords intermediate (21), which is converted to compound (22) through amide formation.

TABLE 1

Effect of inhibitors on the ssDNA annealing and DNA pairing activities of RAD52 and on the DNA pairing activity of RAD51

| Inhibitors | ssDNA annealing (Fluorescence quenching), $IC_{50}$, μM | Inhibition of DNA pairing (D-loop formation), $IC_{50}$, μM | Inhibition of RAD51 paring (D-loop formation), %* |
|---|---|---|---|
| D-A13 | 5.2 | 13.6 ± 0.64 | 102.5 ± 1.1 |
| D-A19 | 4.8 | 7.2 ± 0.28 | 93.7 ± 2.1 |
| D-A21 | 9.8 | 16.2 ± 0.42 | 97.5 ± 2.5 |
| D-C17 | 6.0 | 17.6 ± 0.78 | 92.5 ± 5.0 |
| D-C19 | 2.0 | 4.3 ± 0.35 | 73.6 ± 2.2 |
| D-E05 | 1.7 | 11.3 ± 0.35 | 110.9 ± 4.3 |

TABLE 1-continued

Effect of inhibitors on the ssDNA annealing and DNA pairing activities of RAD52 and on the DNA pairing activity of RAD51

| Inhibitors | ssDNA annealing (Fluorescence quenching), $IC_{50}$, μM | Inhibition of DNA pairing (D-loop formation), $IC_{50}$, μM | Inhibition of RAD51 paring (D-loop formation), %* |
|---|---|---|---|
| D-G09 | 2.0 | 14.8 ± 2.47 | 108.2 ± 3.1 |
| D-G11 | 6.0 | 8.9 ± 1.6 | 110.7 ± 0.2 |
| D-G23 | 5.6 | 7.2 ± 0.96 | 75.6 ± 7.1 |
| D-I01 | 3.6 | 15.4 ± 0.57 | 112.5 ± 4.2 |
| D-I03 | 5.0 | 8.0 ± 1.7 | 95.5 ± 4.3 |
| D-I05 | 4.3 | 8.8 ± 0.42 | 75.1 ± 4.8 |
| D-I07 | 2.0 | 2.7 ± 0.35 | 38.4 ± 6.4 |
| D-I09 | 6.8 | 10.6 ± 1.4 | 58.6 ± 2.9 |
| D-I11 | 4.1 | 6.7 ± 0.78 | 48.6 ± 2.0 |
| D-I19 | 3.5 | 4.1 ± 0.14 | 35.3 ± 5.8 |
| D-K17 | 2.9 | 4.8 ± 0.85 | 89.7 ± 0.4 |

Note:
*The effect of the inhibitors on RAD51 DNA pairing activity was measured at the concentrations that correspond their 10 × $IC_{50}$ for RAD52 pairing activity. 100% of the D-loop yield correspond to the extent of reaction in the presence of 4% DMSO; the actual extent of D-loops was 44.7 ± 0.2% under these conditions.

TABLE 2

Sequences of the oligonucleotides

| N | Length, nt | Sequences (5'→3') |
|---|---|---|
| 337-FLU SEQ ID NO: 1 | 60 | FLU-CACTGTGATGCACGATGATCGACGACAGTAGTCAGT GCTGGGTCAACATCTGTATGCAGG |
| 1337-BHQ1 SEQ ID NO: 2 | 39 | AGCACTGACTACTGTCGTCGATCATCGTGCATCACAGTG-BHQ1 |
| 265-55 SEQ ID NO: 3 | 55 | ATACAGATGTTGACCCAGCACTGACTACTGTCGTCAATCATCGT GCATCACAGTG |
| 90 SEQ ID NO: 4 | 90 | CGGGTGTCGGGGCTGGCTTAACTATGCGGCATCAGAGCAGATTG TACT GAG AGT GCA CCA TAT GCG GTG TGA AAT ACC GCA CAG ATG CGT |

Note:
"FLU" and "BHQ1" denote Fluorescein and Black Hole Quencher 1, respectively

TABLE 3

Calculated properties of D-I03 and D-G23 compounds*

|  | D-I03 | D-G23 |
|---|---|---|
| molecular weight | 429 | 354 |
| cLogP | 3.65 | 3.29 |
| TPSA | 47 | 89 |
| HBD | 2 | 3 |
| HBA | 5 | 7 |
| rotatable bonds | 7 | 7 |

*calculated using ADRIANA.code
TPSA = topological polar surface area
HBD = hydrogen bond donors
HBA = hydrogen bond acceptors
(www dot molecular-networks.com/files/docs/adrianacode/adrianacode_flyer dot pdf)

TABLE 4

Chemical Structures and IUPAC Names of the Compounds in Table 1.

| Inhibitor | Structure | IUPAC name |
|---|---|---|
| D-A13 | 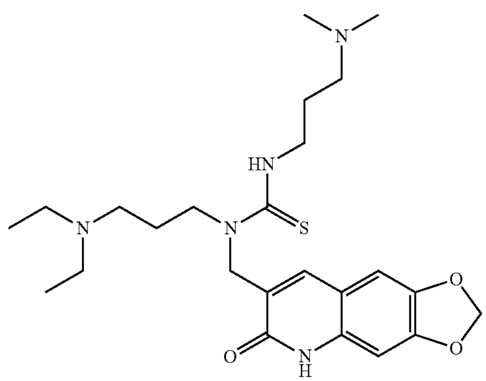 [SMILES: CCN(CC)CCCN(Cc1cc2cc3c(cc2[nH]c1=O)OCO3)C(=S)NCCCN(C)C] | 1-(3-(diethylamino)propyl)-3-(3-(dimethylamino)propyl)-1-((6-oxo-5,6-dihydro-[1,3]dioxolo[4,5-g]quinolin-7-yl)methyl)thiourea |
| D-A19 | 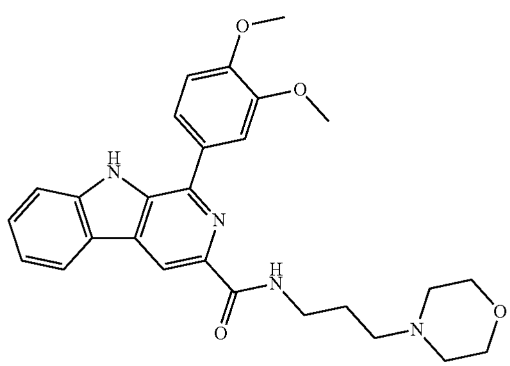 [SMILES: COc1ccc(-c2nc(C(=O)NCCCN3CCOCC3)cc3c2[nH]c2ccccc23)cc1OC] | 1-(3,4-dimethoxyphenyl)-N-(3-morpholinopropyl)-9H-pyrido[3,4-b]indole-3-carboxamide |
| D-A21 | 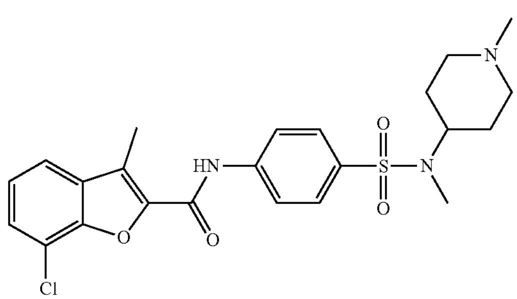 [SMILES: Cc1c(C(=O)Nc2ccc(S(=O)(=O)N(C)C3CCN(C)CC3)cc2)oc2c(Cl)cccc12] | 7-chloro-3-methyl-N-(4-(N-methyl-N-(1-methylpiperidin-4-yl)sulfamoyl)phenyl)benzofuran-2-carboxamide |

TABLE 4-continued

Chemical Structures and IUPAC Names of the Compounds in Table 1.

| Inhibitor | Structure | IUPAC name |
|---|---|---|
| D-C17 | 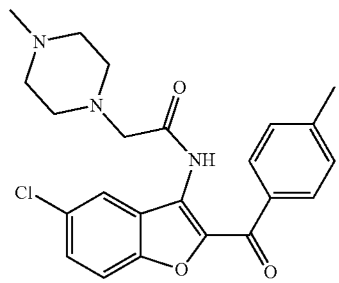 | N-(5-chloro-2-(4-methylbenzoyl)benzofuran-3-yl)-2-(4-methylpiperazin-1-yl)acetamide |
| D-C19 | 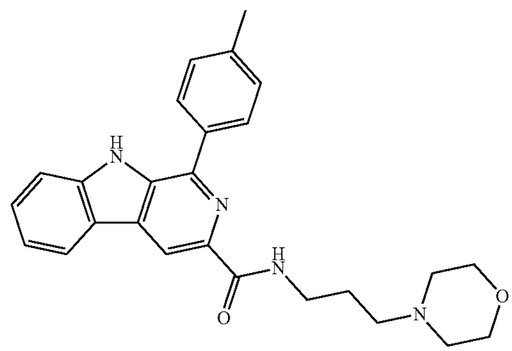 [SMILES: Cc1ccc(-c2nc(C(=O)NCCCN3CCOCC3)cc3c2[nH]c2ccccc23)cc1] | N-(3-morpholinopropyl)-1-(p-tolyl)-9H-pyrido[3,4-b]indole-3-carboxamide |
| D-E05 | 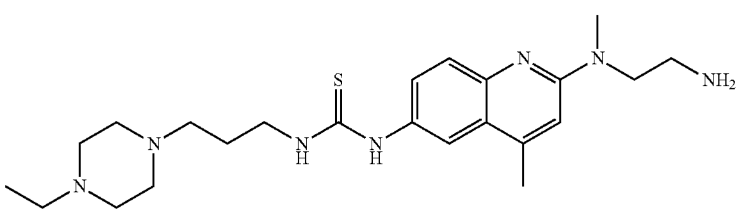 [SMILES: CCN1CCN(CCCNC(=S)Nc2ccc3nc(N(C)CCN)cc(C)c3c2)CC1] | 1-(2-((2-aminoethyl)(methyl)amino)-4-methylquinolin-6-yl)-3-(3-(4-ethylpiperazin-1-yl)propyl)thiourea |
| D-G09 | 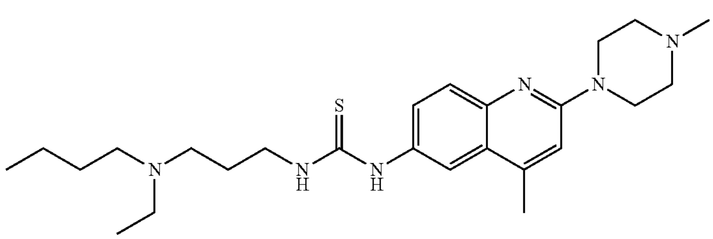 [SMILES: CCCCN(CC)CCCNC(=S)Nc1ccc2nc(N3CCN(C)CC3)cc(C)c2c1] | 1-(3-(butyl(ethyl)amino)propyl)-3-(4-methyl-2-(4-methylpiperazin-1-yl)quinolin-6-yl)thiourea |
| D-G11 | 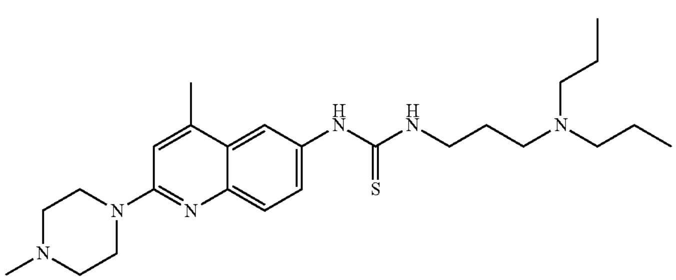 [SMILES: CCCN(CCC)CCCNC(=S)Nc1ccc2nc(N3CCN(C)CC3)cc(C)c2c1] | 1-(3-(dipropylamino)propyl)-3-(4-methyl-2-(4-methylpiperazin-1-yl)quinolin-6-yl)thiourea |

TABLE 4-continued

Chemical Structures and IUPAC Names of the Compounds in Table 1.

| Inhibitor | Structure | IUPAC name |
|---|---|---|
| D-G23 | 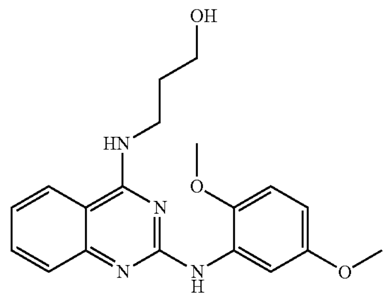 [SMILES: COc1ccc(OC)c(Nc2nc(NCCCO)c3ccccc3n2)c1] | 3-((2-((2,5-dimethoxyphenyl)amino)quinazolin-4-yl)amino)propan-1-ol |
| D-I01 | 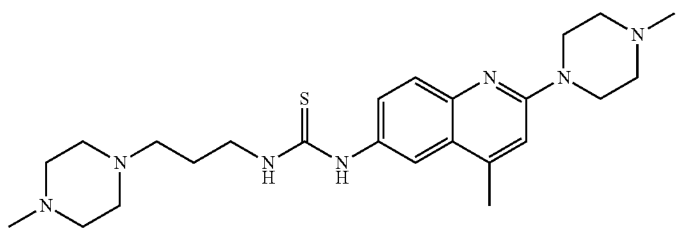 | 1-(4-methyl-2-(4-methylpiperazin-1-yl)quinolin-6-yl)-3-(3-(4-methylpiperazin-1-yl)propyl)thiourea |
| D-I03 | 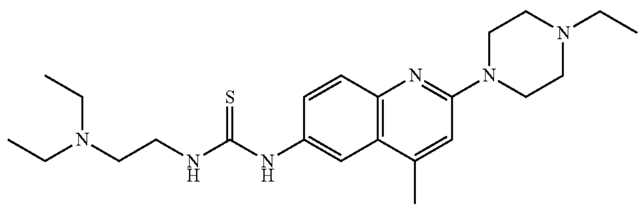 [SMILES: CCN(CC)CCNC(=S)Nc1ccc2nc(N3CCN(CC)CC3)cc(C)c2c1] | 1-(2-(diethylamino)ethyl)-3-(4-methyl-2-(4-ethylpiperazin-1-yl)quinolin-6-yl)thiourea |
| D-I05 | 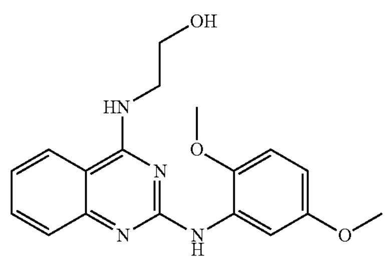 [SMILES: COc1ccc(OC)c(Nc2nc(NCCO)c3ccccc3n2)c1] | 2-((2-((2,5-dimethoxyphenyl)amino)quinazolin-4-yl)amino)ethan-1-ol |
| D-I07 | 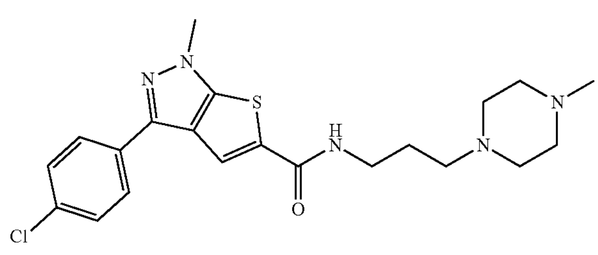 [SMILES: CN1CCN(CCCNC(=O)c2cc3c(-c4ccc(Cl)cc4)nn(C)c3s2)CC1] | 3-(4-chlorophenyl)-1-methyl-N-(3-(4-methylpiperazin-1-yl)propyl)-1H-thieno[2,3-c]pyrazole-5-carboxamide |
| D-I09 | 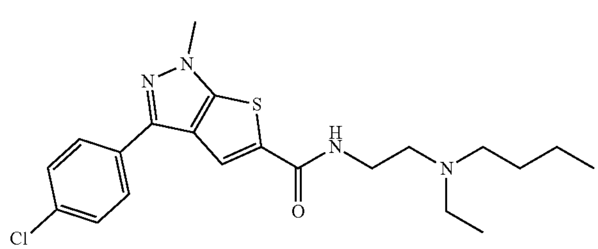 [SMILES: CCCCN(CC)CCNC(=O)c1cc2c(-c3ccc(Cl)cc3)nn(C)c2s1] | N-(2-(butyl(ethyl)amino)ethyl)-3-(4-chlorophenyl)-1-methyl-1H-thieno[2,3-c]pyrazole-5-carboxamide |

TABLE 4-continued

Chemical Structures and IUPAC Names of the Compounds in Table 1.

| Inhibitor | Structure | IUPAC name |
|---|---|---|
| D-I11 | 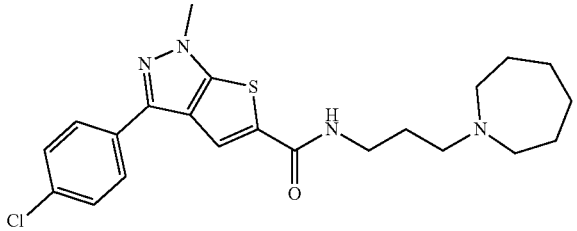 [SMILES: Cn1nc(-c2ccc(Cl)cc2)c2cc(C(=O)NCCCN3CCCCCC3)sc21] | N-(3-(azepan-1-yl)propyl)-3-(4-chlorophenyl)-1-methyl-1H-thieno[2,3-c]pyrazole-5-carboxamide |
| D-I19 | 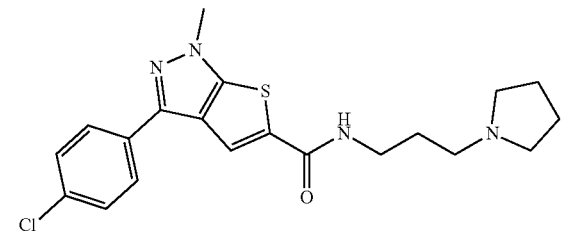 [SMILES: Cn1nc(-c2ccc(Cl)cc2)c2cc(C(=O)NCCCN3CCCC3)sc21] | 3-(4-chlorophenyl)-1-methyl-N-(3-(pyrrolidin-1-yl)propyl)-1H-thieno[2,3-c]pyrazole-5-carboxamide |
| D-K17 | 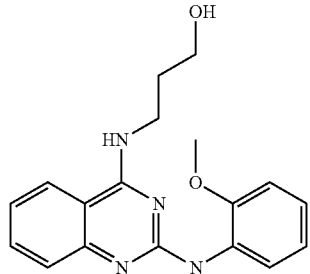 | 3-((2-((2-methoxyphenyl)amino)quinazolin-4-yl)amino)propan-1-ol |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating a cancer in a subject in need thereof, wherein the cancer has at least one BRCA1 or BRCA2 mutation, the method comprising administering to the subject a therapeutically effective amount of a compound of formula (I):

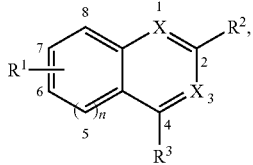

(I)

wherein $R^1$ is selected from the group consisting of:

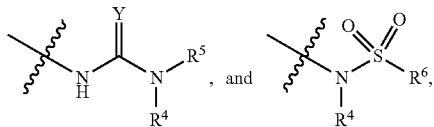

wherein, in $R^1$: $R^4$ is selected from the group consisting of H, —($C_1$-$C_6$)alkyl, —($C_1$-$C_6$)haloalkyl, and —($C_1$-$C_6$)heteroalkyl, and $R^5$ is selected from the group consisting of —($C_1$-$C_6$)alkyl, —($C_1$-$C_6$)haloalkyl, and —($C_1$-$C_6$)heteroalkyl;

$R^2$ is —$NR^4R^5$, wherein in $R^2$ each occurrence of $R^4$ and $R^5$ is independently selected from the group consisting of hydrogen, —($C_1$-$C_6$)alkyl, —($C_1$-$C_6$)haloalkyl, —($C_1$-$C_6$)heteroalkyl, aryl, and heteroaryl, wherein the aryl or heteroaryl group is optionally substituted, or $R^4$ and $R^5$, together with the nitrogen to which $R^4$ and $R^5$ are connected, form —($C_3$-$C_{10}$)heterocyclyl;

$R^3$ is selected from the group consisting of hydrogen, —($C_1$-$C_6$)alkyl, —($C_1$-$C_6$)haloalkyl, —($C_4$-$C_6$)heteroalkyl, —F, —Cl, —Br, —CN, —$NO_2$, —$OR^7$, —$SR^7$, —S(=O)$R^7$, —S(=O)$_2R^7$, —C(=O)$R^7$, —OC(=O)$R^7$, and —$CO_2R^7$;

each occurrence of $R^6$ is independently selected from the group consisting of —($C_1$-$C_6$)alkyl, —($C_1$-$C_6$)heteroalkyl, —($C_2$-$C_{10}$)heterocyclyl, aryl, and heteroaryl, wherein the —($C_3$-$C_{10}$)heterocyclyl, aryl or heteroaryl group is optionally substituted;

each occurrence of $R^7$ is independently selected from the group consisting of H, —($C_1$-$C_6$)alkyl, —($C_1$-$C_6$)heteroalkyl, —($C_3$-$C_6$)cycloalkyl, —($C_4$-$C_{10}$)heterocyclyl, aryl, and —($C_5$-$C_{10}$)heteroaryl, wherein the alkyl, heteroalkyl, cycloalkyl, heterocyclyl, aryl, or heteroaryl group is optionally substituted;

X at 1-position is N and X at 3-position is CH;

Y is O or S;

n is 0 and $R^1$ is connected to the aryl ring at the 6, 7, or 8 position;

a salt, solvate, tautomer, enantiomer, diastereoisomer, or N-oxide thereof; and any combinations thereof.

2. The method of claim 1, wherein the method further comprises administering to the subject at least one additional therapeutic agent that treats cancer.

3. A method of treating a cancer in a subject in need thereof, wherein the cancer has at least one BRCA1 or BRCA2 mutation, the method comprising administering to the subject a therapeutically effective amount of a compound selected from the group consisting of:

1-(3-(diethylamino)propyl)-3-(3-(dimethylamino)propyl)-1-((6-oxo-5,6-dihydro-[1,3]dioxolo[4,5-g]quinolin-7-yl)methyl)thiourea;

1-(2-((2-aminoethyl)(methyl)amino)-4-methylquinolin-6-yl)-3-(3-(4-ethylpiperazin-1-yl)propyl)thiourea;

1-(3-(butyl(ethyl)amino)propyl)-3-(4-methyl-2-(4-methylpiperazin-1-yl)quinolin-6-yl)thiourea;

1-(3-(dipropylamino)propyl)-3-(4-methyl-2-(4-methylpiperazin-1-yl)quinolin-6-yl)thiourea;

1-(4-methyl-2-(4-methylpiperazin-1-yl)quinolin-6-yl)-3-(3-(4-methylpiperazin-1-yl)propyl)thiourea;

1-(2-(diethylamino)ethyl)-3-(4-methyl-2-(4-methylpiperazin-1-yl)quinolin-6-yl)thiourea;

1-(2-(diethylamino)ethyl)-3-(4-methyl-2-(4-ethylpiperazin-1-yl)quinolin-6-yl)thiourea;
a salt, solvate, tautomer, enantiomer, diastereoisomer, or N-oxide thereof, and any combinations thereof.

4. The method of claim 1, wherein the cancer is selected from the group consisting of squamous cell cancer, lung cancer, vulval cancer, thyroid cancer, adenocarcinoma of the lung and squamous carcinoma of the lung, cancer of the peritoneum, hepatocellular cancer, gastric or stomach cancer pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer.

5. The method of claim 1, wherein the cancer is ovarian cancer or breast cancer.

6. A method of treating ovarian or breast cancer in a subject in need thereof, wherein the cancer has at least one BRCA1 or BRCA2 mutation, the method comprising administering to the subject a therapeutically effective amount of a compound of formula (I):

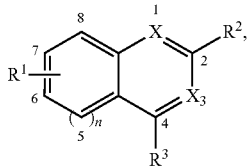

(I)

wherein in (I):
$R^1$ is selected from the group consisting of:

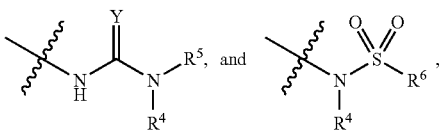

wherein, in $R^1$: $R^4$ is selected from the group consisting of $—(C_1-C_6)$alkyl, $—(C_1-C_6)$haloalkyl, and $—(C_1-C_6)$heteroalkyl, and $R^5$ is selected from the group consisting of $—(C_1-C_6)$alkyl, $—(C_1-C_6)$haloalkyl; and $—(C_1-C_6)$heteroalkyl;

$R^2$ is $—NR^4R^5$, wherein in $R^2$ each occurrence of $R^4$ and $R^5$ is independently selected from the group consisting of hydrogen, $—(C_1-C_6)$alkyl, $—(C_1-C_6)$haloalkyl, $—(C_1-C_6)$heteroalkyl, aryl; and heteroaryl, wherein the aryl or heteroaryl group is optionally substituted, or $R^4$ and $R^5$, together with the nitrogen to which $R^4$ and $R^5$ are connected, form $—(C_3-C_{10})$heterocyclyl;

$R^3$ is selected from the group consisting of hydrogen, $—(C_1-C_6)$alkyl, $—(C_1-C_6)$haloalkyl, $—(C_1-C_6)$heteroalkyl, $—F$, $—Cl$, $—Br$, $—CN$, $—NO_2$, $—OR^7$, $—SR^7$, $—S(=O)R^7$, $—S(=O)_2R^7$, $—C(=O)R^7$, $—OC(=O)R^7$, and $—CO_2R^7$;

each occurrence of $R^6$ is independently selected from the group consisting of $—(C_1-C_6)$alkyl, $—(C_1-C_6)$heteroalkyl, $—OR^7$, $—(C_3-C_{10})$heterocyclyl, aryl, and heteroaryl, wherein the $—(C_3-C_{10})$heterocyclyl, aryl or heteroaryl group is optionally substituted;

each occurrence of $R^7$ is independently selected from the group consisting of H, $—(C_1-C_6)$alkyl, $—(C_1-C_6)$heteroalkyl, $—(C_3-C_6)$cycloalkyl, $—(C_4-C_{10})$heterocyclyl, aryl, and $—(C_5-C_{10})$heteroaryl, wherein the alkyl, heteroalkyl, cycloalkyl, heterocyclyl, aryl, or heteroaryl group is optionally substituted;

X at 1-position is N and X at 3-position is CH;
Y is O or S;
n is 0 and $R^1$ is connected to the aryl ring at the 6, 7, or 8 position;

or a salt; solvate, tautomer, enantiomer, diastereoisomer, or N-oxide thereof, and any combinations thereof.

7. The method of claim 6, the method further comprising administering to the subject at least one additional therapeutic agent that treats cancer.

8. A method of treating ovarian or breast cancer—in a subject in need thereof, wherein the cancer has at least one BRCA1 or BRCA2 mutation, the method comprising administering to the subject a therapeutically effective amount of a compound selected from the group consisting of:

1-(3-(diethylamino)propyl)-3-(3-(dimethylamino)propyl)-1-((6-oxo-5,6-dihydro-[1,3]dioxolo[4,5-g]quinolin-7-yl)methyl)thiourea;
1-(2-((2-aminoethyl)(methyl)amino)-4-methylquinolin-6-yl)-3-(3-(4-ethylpiperazin-1-yl)propyl)thiourea;
1-(3-(butyl(ethyl)amino)propyl)-3-(4-methyl-2-(4-methylpiperazin-1-yl)quinolin-6-yl)thiourea;
1-(3-(dipropylamino)propyl)-3-(4-methyl-2-(4-methylpiperazin-1-yl)quinolin-6-yl)thiourea;
1-(4-methyl-2-(4-methyl piperazin-1-yl)quinolin-6-yl)-3-(3-(4-methylpiperazin-1-yl)propyl)thiourea;
1-(2-(diethylamino)ethyl)-3-(4-methyl-2-(4-methylpiperazin-1-yl)quinolin-6-yl)thiourea;
1-(2-(diethylamino)ethyl)-3-(4-methyl-2-(4-ethylpiperazin-1-yl)quinolin-6-yl)thiourea;
a salt, solvate, tautomer, enantiomer, diastereoisomer, or N-oxide thereof, and any combinations thereof.

9. The method of claim 3, wherein the cancer is selected from the group consisting of squamous cell cancer, lung cancer, vulval cancer, thyroid cancer, adenocarcinoma of the lung and squamous carcinoma of the lung, cancer of the peritoneum, hepatocellular cancer, gastric or stomach cancer pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, hepatic carcinoma, anal carcinoma, penile carcinoma, and head and neck cancer.

10. The method of claim 3, wherein the cancer is ovarian cancer or breast cancer.

* * * * *

SEQUENCE LISTING

```
<160> NUMBER OF SEQ ID NOS: 4

<210> SEQ ID NO 1
<211> LENGTH: 60
<212> TYPE: DNA
<213> ORGANISM: Artificial Sequence
<220> FEATURE:
<223> OTHER INFORMATION: 337-FLU: synthetic ssDNA, bound to FLU

<400> SEQUENCE: 1
cactgtgatg cacgatgatc gacgacagta gtcagtgctg ggtcaacatc tgtatgcagg      60

<210> SEQ ID NO 2
<211> LENGTH: 39
<212> TYPE: DNA
<213> ORGANISM: Artificial Sequence
<220> FEATURE:
<223> OTHER INFORMATION: 1337-BHQ1: synthetic ssDNA, bound to FLU and
      BHQ1

<400> SEQUENCE: 2
```

```
<210> SEQ ID NO 3
<211> LENGTH: 55
<212> TYPE: DNA
<213> ORGANISM: Artificial Sequence
<220> FEATURE:
<223> OTHER INFORMATION: 265-55: synthetic ssDNA

<400> SEQUENCE: 3
atacagatgt tgacccagca ctgactactg tcgtcaatca tcgtgcatca cagtg      55

<210> SEQ ID NO 4
<211> LENGTH: 90
<212> TYPE: DNA
<213> ORGANISM: Artificial Sequence
<220> FEATURE:
<223> OTHER INFORMATION: 90: synthetic ssDNA

<400> SEQUENCE: 4
cgggtgtcgg ggctggctta actatgcggc atcagagcag attgtactga gagtgcacca   60
tatgcggtgt gaaataccgc acagatgcgt                                    90
```